United States Patent
Kozhemyakin et al.

(10) Patent No.: US 7,371,411 B2
(45) Date of Patent: *May 13, 2008

(54) METHODS FOR PRODUCTION OF THE OXIDIZED GLUTATHIONE COMPOSITE WITH CIS-DIAMMINEDICHLOROPLATINUM AND PHARMACEUTICAL COMPOSITIONS BASED THEREOF REGULATING METABOLISM, PROLIFERATION, DIFFERENTIATION AND APOPTOTIC MECHANISMS FOR NORMAL AND TRANSFORMED CELLS

(75) Inventors: Leonid A. Kozhemyakin, St. Petersburg (RU); Mark B. Balasovski, St. Petersburg (RU)

(73) Assignee: Novelos Therapeutics, Inc., Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/646,128

(22) Filed: Dec. 27, 2006

(65) Prior Publication Data

US 2007/0123450 A1  May 31, 2007

Related U.S. Application Data

(63) Continuation of application No. 10/747,855, filed on Dec. 29, 2003, now Pat. No. 7,169,412, which is a continuation of application No. 10/404,914, filed on Apr. 1, 2003, now abandoned, which is a continuation of application No. 09/842,104, filed on Apr. 30, 2001, now abandoned, which is a continuation of application No. 09/241,232, filed on Feb. 1, 1999, now Pat. No. 6,312,734, which is a continuation-in-part of application No. 09/237,801, filed on Jan. 27, 1999, now abandoned.

(30) Foreign Application Priority Data

Nov. 23, 1998 (RU) ................... 98120753

(51) Int. Cl.
*A61K 33/24* (2006.01)
*A61K 38/08* (2006.01)

(52) U.S. Cl. .......... 424/617; 424/649; 514/6; 514/21

(58) Field of Classification Search ............ None
See application file for complete search history.

(56) References Cited

U.S. PATENT DOCUMENTS

| | | | |
|---|---|---|---|
| 4,550,022 A | 10/1985 | Garabedian et al. |
| 4,761,399 A | 8/1988 | Pilotto et al. |
| 4,871,528 A | 10/1989 | Tognella et al. |
| 4,927,808 A | 5/1990 | Kitahara et al. |
| 4,968,671 A | 11/1990 | Asano et al. |
| 5,104,852 A | 4/1992 | Kralick et al. |
| 5,206,220 A | 4/1993 | Hilton |
| 5,208,249 A | 5/1993 | Rowe et al. |
| 5,223,488 A | 6/1993 | Ogata et al. |
| 5,248,697 A | 9/1993 | Wilmore |
| 5,316,767 A | 5/1994 | Hera et al. |
| 5,352,771 A | 10/1994 | Kostic et al. |
| 5,789,000 A | 8/1998 | Hausheer et al. |
| 5,916,878 A | 6/1999 | Kolobov et al. |
| 5,977,073 A | 11/1999 | Khaled |
| 6,013,632 A | 1/2000 | Jones et al. |
| 6,159,500 A | 12/2000 | Demopoulos et al. |
| 6,165,979 A | 12/2000 | Kozhemyakin et al. |
| 6,251,857 B1 | 6/2001 | Kozhemyakin et al. |
| 6,312,734 B1 | 11/2001 | Kozhemyakin et al. |
| 6,410,516 B1 | 6/2002 | Baltimore et al. |
| 6,492,329 B1 | 12/2002 | Kozhemyakin et al. |
| 7,169,412 B2 | 1/2007 | Kozhemyakin et al. |

FOREIGN PATENT DOCUMENTS

| | | |
|---|---|---|
| EP | 0 265 719 A1 | 5/1988 |
| EP | 0502313 | 9/1992 |
| EP | 616803 | 9/1994 |
| EP | 764442 | 9/1997 |
| JP | 62-221698 | 9/1987 |
| JP | 10-59839 | 3/1989 |
| JP | 02-045420 A | 2/1990 |

| | | |
|---|---|---|
| JP | 02-193931 | 7/1990 |
| JP | 4-9336 | 1/1992 |
| JP | 04-009336 A | 1/1992 |
| JP | 04-230698 | 8/1992 |
| JP | 05-301811 | 11/1993 |
| JP | 07-82167 | 3/1995 |
| JP | 08-56655 A | 3/1996 |
| WO | WO 92/21368 | 12/1992 |
| WO | WO 94/00141 | 1/1994 |
| WO | WO 96/40205 | 12/1996 |
| WO | WO 97/21443 | 6/1997 |
| WO | WO 97/21444 | 6/1997 |
| WO | WO 00/31120 | 6/2000 |
| WO | WO 2004/024062 | 3/2004 |

OTHER PUBLICATIONS

"Glutathione," Unknown Dictionary (Russian) and translation, p. 979, 1961.

A. Szent-Györgyi, "Charge Transfer and Electronic Mobility," Biochemistry, vol. 58, pp. 2012-2014, 1967.

Ahmed, K.A., et al., "Nonenzymic Reactivation of Reduced Bovine Pancreatic Ribonuclease by Air Oxidation and by Glutathione Oxidoreduction Buffers," The Journal of Biological Chemistry, vol. 250, No. 21, pp. 8477-8482 (1975).

Araie, M., et al., "Effect of Oxidized Glutathione on the Barrier Function of the Corneal Endothelium," Investigative Ophthalmology & Visual Science, vol. 29, pp. 1884-1887 (1988).

Aukrust, P., et al., "Increased Levels of Oxidized Glutathione in CD4+ Lymphocytes Associated With Disturbed Intracellular Redox Balance in Human Immunodeficiency Virus Type I Infection," Blood, vol. 86, No. 1, pp. 258-267 (1995).

Barbato, G., et al., Inhibitor binding induces active site stabilization of the HCV NS3 protein serine protease domain, The EMBO Journal, vol. 19, No. 6, pp. 1195-1206 (2000).

Barot-Ciorbaru, R., et al., "Immunomodulators from Nocardia opaca," Forum on immunomodulators, pp. 63-77 (1995).

Beckett, G. J., et al., "Glutathione S-Transferases: Biomedical Applications," Advances in Clinical Chemistry, vol. 30, pp. 281-381 (1993).

Beutler. E., "Nutritional and Metabolic Aspects of Glutathione," Annu. Rev. Nutr., vol. 9, pp. 287-302 (1989).

Blight, K.J., et al., "Molecular virology of hepatitis C virus: an update with respect to potential antiviral targets," Antiviral Therapy, vol. 3, pp. 71-81 (1998).

Bloy, C., et al., "RU 41740 (Biostim), an immunomodulating agent from bacterial origin," Forum on immunomodulators, pp. 85-100 (1995).

Bouffard, P., et al., "An in Vitro Assay for Hepatitis C Virus NS3 Serine Proteinase," Virology, vol. 209, pp. 52-59 (1995).

Butkiewicz, N, et al., "Virus-Specific Cofactor Requirement and Chimeric Hepatitis C Virus/GB Virus B Nonstructural Protein 3," Journal of Virology, vol. 74, No. 9, pp. 4291-4301 (2000).

Butkiewicz, N. J., et al., "Hepatitis C NS3 Protease: Restoration of NS4A Cofactor Activity by N-Biotinylation of Mutated NS4A Using Synthetic Peptides," Biochemical and Biophysical Research Communications, vol. 267, pp. 278-282 (2000).

C.D. Gregory, "Apoptosis: a role in neoplasia?", Cell Proliferation in Cancer Regulatory Mechanisms of Neoplastic Cell Growth, L. Pusztai & C.E. Lewis editors, Oxford University Press, Chapter 13, pp. 342-359, 1996.

Calabrese, F., et al., "Liver cell Apoptosis in Chronic Hepatitis C Correlates With Historical But Not Biochemical Activity or Serum HCV-RNA Levels," Hepatology, vol. 31, No. 5, pp. 1153-1159 (2000).

Carreno, V., et al., "A phase I/II study of recombinant human interleukin-12 in patients with chronic hepatitis B*," Journal of Hepatology, vol. 32, pp. 317-324 (2000).

Cerretani, M., et al., "A High-Throughput Radiometric Assay for Hepatitis C Virus NS3 Protease," Analytical Biochemistry, vol. 226, pp. 192-197 (1999).

Chen, M., et al., "Human Murine Antibody Recognition is Focused on the ATPase/Helicase, But Not the Protease Domain of the Hepatitis C Virus Nonstructural 3 Protein," Hepatology, vol. 28, pp. 219-224 (1998).

Cirelli, R., et al., "Interferons in human papillomavirus infections," Antiviral Research, vol. 24, pp. 191-204 (1994).

Cohen, G., "Enzymatic/Nonenzymatic Sources of Oxyradicals and Regulation of Antioxidant Defenses," Annals New York Academy of Sciences, pp. 8-14. (not dated).

D.L. Vaux & A. Strasser, "The molecular biology of apoptosis," Proceedings of the National Academy of Sciences, Proc. Natl. Acad. Sci. USA, vol. 93, pp. 2239-2244, Mar. 1996.

De Flora, S., et al., "Antioxidant Activity and Other Mechanisms of Thiols Involved in Chemoprevention of Mutation and Cancer," The American Journal of Medicine, vol. 91, pp. 122-130 (1991).

Devlin, et al., "Gluathione, Amino Acid Metabolism II: Metabolism of the Individual Amino Acids," Textbook of Biochemistry with Clinical Correlations, $3^{rd}$Edition, pp. 522-528 (1992).

Dienstag, J. L., et al., "Lamivudine as Initial Treatment for Chronic Hepatitis B in the Untied States," The New England Journal of Medicine, vol. 341, No. 17, pp. 1256-1263 (1999).

Dillman, R. O., "The Clinical Experience with Interleukin-2 in Cancer Therapy," Cancer Biotherapy, vol. 9, No. 3, pp. 183-209 (1994).

Droge, W., et al., "Functions of glutathione and glutathione disulfide in immunology and immunopathology," The FASEB Journal, vol. 8, pp. 1132-1138 (1994).

Estrela, J.M., et al., "Regulation of glutathione metabolism in Ehrilch ascites tumour cells," Biochem. J., vol. 286, pp. 257-262 (1992).

Fabris, P., et al., "TTV infection in patients with acute hepatitis of defined aetiology and in acute non-A-E hepatitis," Journal of Hepatology, vol. 32, pp. 661-665 (2000).

Fan, X.G., et al., "Circulating Th1 and Th2 cytokines in patients with hepatitis C virus infection," Mediators of Inflammation, vol. 7, pp. 295-297 (1998).

Forman, A., "Neurologic Complications of Cytokine Therapy," Oncology, vol. 8, No. 4, pp. 105-117 (1994).

Gallinari, P., et al., "Multiple Enzymatic Activities Associated with Recombinant NS3 Protein of Hepatitis C Viris," J. Virol, vol. 72, No. 8, pp. 6758-6769 (1998).

Galter, D., et al., "Distinct effects of glutathione disulphide on the nuclear transcription factors κB and the activator protein-1," Eur. J. Biochem., vol. 221, pp. 639-348 (1994).

Garaci, E., et al., "Combination therapy with BRMs in cancer and infectious diseases," Mechanisms of Ageing and Development, vol. 96, pp. 103-116 (1997).

Gillan, E., et al., "Colony-Stimulating Factors in the Modulation of Sepsis," New Horizons, vol. 1, No. 1, pp. 96-109 (1993).

Gillis, D., et al., "Active versus passive immunization against hepatitis A in the Israel defence forces: a cost-benefit analysis," Vaccine, vol. 18, pp. 3005-3010 (2000).

Giugliano, D., et al., "Diabetes Mellitus, Hypertension and Cardiovascular Disease: Which Role for Oxidative Stress?," Metabolism, vol 44, No. 3, pp. 363-368 (1995).

Gregory, C.D., "Apoptosis: a role in neoplasia?," Cell Proliferation, Ch. 13, pp. 342. (not dated).

Gruner, N.H., et al., "Association of Hepatitis C Virus-Specific CD8+ T Cells with Viral Clearance in Acute Hepatitis C," The Journal of Infectious Diseases, vol. 181, pp. 1528-1536 (2000).

Gwack, Y., et al., "Characterization of RNA Binding Activity and RNA Helicase Activity of the Hepatitis C Virus NS3 Protein," Biochemical and Biophysical Research Communications, vol. 225, pp. 654-659 (1996).

Hack, C.E., et al., "C1-inhibitor substitution therapy in septic shock and in the vascular leak syndrome induced by high doses of interleukin-2," Intensive Care Med., vol. 19, pp. S19-S28 (1993).

Hansson, M., et al., "The Colony Stimulating Factors," Med. Oncol. & Tumor Pharmacother, vol. 10, No. 1/2, pp. 5-12 (1993).

Hargrove, M.E., "Regulation by Glutathione of the Activation and Differentiation of IL-4-Dependent Activated Killer Cells," Cellular Immunology, vol. 149, pp. 433-443 (1993).

Hayashi, J., et al., "A Relationship between the Evolution of Hepatitis C and Variants, Liver Damage, and Hepatocellular Carcinoma in Patients with Hepatitis C Viremia," *The Journal of Infectious Diseases*, vol. 181, pp. 1523-1527 (2000).
Hieber, U., et al., "Tumor Necrosis Factor for the Treatment of Malignancies," *Oncology*, vol. 51, pp. 142-153 (1994).
Hockenbery, D.M., "Bcl-2 Functions in an Antioxidant Pathway to Prevent Apoptosis," *Cell*, vol. 75, pp. 241-251 (1993).
Holmlund, J. T., "Cytokines," *Cancer Chemotherapy and Biological Response Modifiers Annual*, vol. 14, pp. 150-206 (1993).
Hope, D. B., et al., "A Highly Potent Analogue of Oxytocin, Desamino-oxytocin," *The Journal of Biological Chemistry*, vol. 237, No. 5, pp. 1563-1566 (1962).
Hou-Jun, Y., et al., "N-S phosphoryl migration in phosphoryl glutathion," *Int. J. Peptide Res.*, vol. 42, pp. 39-43 (1993).
Hultgren, C., et al., "The anitviral compound ribavirin modulates the T helper (Th) 1/Th2 subset balance in hepatitis B and C virus-specific immune responses," *Journal of General Virology*, vol. 79, pp. 2381-2391 (1998).
International Search Report dated Jan. 27, 1997, PCT/RU96/00226.
International Search Report dated May 27, 1997, PCT/RU96/00340.
Jones, R.J., et al., "Undetectable serum caeruloplasmin in a woman with chronic hepatitis C infection," *J. Hepatol*, vol. 4, pp. 703-704 (2000).
Kamber, B., et al., "The Synthesis of Cystine Peptides by Iodine Oxidation of S-Trityl-cysteine and S-Acetamidomethyl-cystein Peptides," *Helvetic Chimica Acta*, vol. 63, pp. 899-915 (1980).
Kato, E., et al., "Conversion of Thiols into Disulfides with Diethyl Bromomalonate," *Chem. Pharm. Bull*, Vo. 34, pp. 486-495 (1986).
Kehrer, J. P., et al., "Cellular Reducing Equivalents and Oxidative Stress," *Free Radical Biology & Medicine*, vol. 17, No. 1, pp. 65-75 (1994).
Keusch, G. T., "Antioxidants in Infection," *J. Nutr. Sci. Vitaminol.*, vol. 39, pp. S23-S33 (1993).
Knodell Histological Activity Index (web page) last accessed Mar. 6, 2001.
Kozhemyakin, L.A., et al., "Glutoxim, a disulfide-containing hexapeptide, ensures a favorable survival outcome and better tolerability of chemotherapy in patients with Stage III-IV non-small-cell lung cancer," *Novelos Power Point Presentation*, 4th Annual International Lung Cancer Conference, Greece, Apr. 27, 2001.
Krieter, H., et al., "Infusion of Oxidized Glutathione Enhances Postischemic segment-shortening in dog hearts," *Cardioscience*, vol. 5, No. 2, pp. 115-126 (1994).
Kyono, K., et al., "Detection of Hepatitis C Virus Helicase Activity Using the Scintillation Proximity Assay System," *Analytical Biochemistry*, vol. 257, pp. 120-126 (1998).
Lau, D., et al., "Hepatitis G Virus and Human Immunodeficiency Virus Coinfection: Response to Interferon-α Therapy," *Journal of Infectious Diseases*, vol. 180, pp. 1334-1337 (1999).
Lee, J.H., et al., "Antiviral Effect of Human Recombinant Interleukin-12 in Patients Infected with Hepatitis C Virus," *Journal of Medical Virology*, vol. 60, pp. 264-268 (2000).
Lempers, et al., Reactions of [P+CL (dien)] with Glutathione . . . , Inorg. Chim. Acta. vol. 152, pp. 201-207, 1988.
Li, C., et al., "Complete Regression of Well-established Tumors Using a Novel Water-Soluble Poly(L-Glutamic Acid)-Paclitaxel Conjugate," *Cancer Research*, vol. 58, pp. 2404-2409 (1998).
Lyttle, M.H., et al., "Isozyme-Specific Glutathione-S-Transferase Inhibitors: Design and Synthesis," *J. of Medicinal Chemistry*, vol. 37, pp. 189-194 (1994).
Lyttle., M.H., et al., "Giutathione-S-transferase Activates Novel Alkylating Agents," *J. Med. Chem*, vol. 37, pp. 1501-1507 (1994).
Malik, A.H., et al, "Chronic Hepatitis B Virus Infection: Treatment Strategies for the Next Millennium," *Annals of Internal Medicine*, vol. 132, No. 9 (2000).
Malnick, S.D., et al., "Treatment of Chronic Hepatitis C Virus Infection," *The Annuals of Pharmacotherapy*, vol. 34, pp. 1156-1164 (2000).
McHutchinson, J.G., et al., "A Pilot Study of Daily Subcutaneous Interleukin-10 in Patients with Chronic Hepatitis C Infection," *Journal of Interferon and Cytokine Research*, vol. 19, 1265-1270 (1999).
Meister, A., et al., "Glutathione," *Ann. Rev. Biochem.*, vol. 52, pp. 711-760 (1983).
Meyer, M., et al., "$H_2O_2$ and antioxidants have opposite effects on activation of NF-xB and AP-1 in intact cells: AP-1 as secondary antioxidant-responsive factor," *The EMBO Journal*, vol. 12, No. 5, pp. 2005-2015 (1993).
Michiels, C., et al., "Importance of SE-Glutathione Peroxidase, Catalase, and CU/ZN-SOD for Cell Survival Against Oxidative Stress," *Free Radical Biology & Medicine*, vol. 17, No. 3, pp. 235-248 (1994).
Missale, G., et al., "Mediatori citochinici nel'infiammazione acuta e nei fenomeni di cronicizzazione delle epatiti virali," *Ann. Ital. Med. Int.*, vol. 10, pp. 14-18 (1995).
Mittelman, M., et al., "Clinical Application of Recombinant Erythropoietin in Myelodyspliasia," *Hematology/Oncology Clinics of North America*, vol. 8, No. 5, pp. 993-1009 (1994).
Morstyn, G., et al., "Hematopoietic growth factors in cancer chemotherapy," *Cancer Chemotherapy and Biological Response Modifiers Annual*, vol. 14, pp. 353-370 (1993).
Murray, H. W., "Interferon-Gamma and Host Antimicrobial Defense: Current and Future Clinical Applications," *The American Journal of Medicine*, vol. 97, pp. 459-467 (1994).
Neidhart, J. A., "Hematopoietic Cytokines," *Cancer*, vol. 72, No. 11, pp. 3381-3386 (1993).
Nelson, D. R., et al., "Interleukin 10 Treatment Reduces Fibrosis in Patients with Chronic Hepatitis C: A Pilot Trial of Interferon Nonresponders," *Gastroenterology*, vol. 118, pp. 655-660 (2000).
Nelson, S., "Role of Granulocyte Colony-Stimulating Factor in the Immune Response to Acute Bacterial Infection in the Non-neutropenic Host: An Overview," *Clinical Infectious Diseases*, vol. 18, pp. 197-204 (1994).
Nemunaitis, J., "User of hematopoietic growth factors in marrow transplantation," *Current Opinion in Oncology*, vol. 6, pp. 139-145 (1994).
Nishida, T., et al., "The Network Structure of Corneal Fibroblasts in the Rat as Revealed by Scanning Electron Microscopy," *Investigative Ophthalmology & Visual Science*, vol. 29, pp. 1887-1890 (1988).
Offenstadt, G., et al., "Cytokines et etats infectieux graves," *Path Biol.*, vol. 41, pp. 820-831 (1993).
Ohta, et al., Reaction of oxidized glutathione . . . , Int. J. Pharmaceutics vol. 161, pp. 15-21, 1998.
Pol, S., et al., "Combination of Ribavirin and Interferon-Alfa Surpasses High Doses of Interferon-Alfa Alone in Patients with Genotype-1b-Related Chronic Hepatitis C," *Hepatology*, vol. 31, No. 6, pp. 1338-1344 (2000).
Polyak, S.J., et al., "The molecular basis for responsiveness to anti-viral therapy in hepatitis C," *Forum Trends in Experimental and Clinical Medicine*, No. 10.1, pp. 46-58 (2000).
Raggi, M.A., "Spectrophotometric determination of thiols in human lymphocytes," *Pharmazie*, vol. 53, pp. 239-242 (1998).
Raggi, M.A., "Studio della cinetica di reazione tra Pd (II) e glutatione ossidato," *Bio. Chim. Parmaccurieo*, vol. 131, No. 8, pp. 318-319 (1992).
Renard, D. C., et al., "Oxidized glutathione causes sensitization of calcium release to inositol 1,4,5-trisphosphate in permeabilized hepactocytes," *Biochem J.*, vol. 284, pp. 507-512 (1992).
Rizzetto, M., et al., "Response of Pre-Core Mutant Chronic Hepatitis B Infection to Lamivudine," *Journal of Medical Virology*, vol 61, pp. 398-402 (2000).
Ryu, C. J., et al., "An 80-Kilodalton Protein That Binds to the Pre-S1 Domain of Hepatitis B Virus," *Journal of Virology*, vol. 74, No. 1, pp. 110-116 (2000).
Saito, M., "OK-432, a killed streptococcal preparation, in the treatment of animal and human cancer and its mechanisms of action," *Forum on immunomodulators*, pp. 13-30, (1995).
Sardesai, V.M., "Role of Antioxidants in Health Maintenance," *Nutrition in Clinical Practice*, vol. 10, pp. 19-25 (1995).
Schiff, E.R., "Lamivudine for Hepatitis B in Clincal Practice," *Journal of Medical Virology*, vol. 61, pp. 386-391 (2000).
Sher, A., "Regulation of immunity to Parasites by T cells and T cell-derived cytokines," *Annu. Rev. Immunol.*, vol. 10, pp. 385-409 (1992).

Sokolovsky, M., et al., "On the Synthesis of Cysteine Peptides," *J. Am. Chem. Soc.*, vol. 86, pp. 1202-1206 (1963).

Staal, F., et al., "Intracellular thiols regulate activation of nuclear factor κb and transcription of human immunodeficiency virus," *Proc. Natl. Acad. Sci. USA*, vol. 87, pp. 9943-9947, (1990).

Suthanthiran, M., et al., "Glutathione regulates activation-dependent DNA synthesis in highly purified normal human T lymphocytes stimulated via the CD2 and CD3 antigens," *Proc. Natl. Acad. Sci.*, vol. 87, pp. 3343-3347 (1990).

Szent-Gyorgyi, A., "Charge Transfer and Electronic Mobility," *Biochemistry*, vol. 58, pp. 2012-2014 (1967).

Takikawa, S., et al., "Cell Fusion Activity of Hepatitis C Virus Envelope Proteins," *Journal of Virology*, vol. 74, No. 11, pp. 5066-5074 (2000).

Tam, J. P., "Synthesis of biologically active transforming growth factor alpha," *Int. J. Peptide Protein Res.*, vol. 29, pp. 421-432 (1987).

Terradez, P., et al., "Depletion of tumour glutathione in vivo by buthionine sulphoximine: modulation by the rate of cellular proliferation and inhibition of cancer growth," *Biochem. J.*, vol. 292, pp. 447-483 (1993).

Tew, K. D., "Glutathione-associated Enzymes in Anticancer Drug Resistance," *Cancer Research*, vol. 54, pp. 4313-4320 (1994).

Thomas, D. L., et al., "Determinants of the Quantity of Hepatitis C Virus RNA," *Journal of Infectious Diseases*, vol. 181, pp. 844-851 (2000).

Toyoda, H., et al., "Comparison of Characteristics Between Patients with GB Virus C/Hepatitis G Virus (GBV-C/HGV) RNA and those with GBV-C/HGV E2-Antibody in Patients with Hempohilia," *Journal of Medical Virology*, vol. 60, pp. 34-38 (2000).

Trankmann, P., et al., "Einfluβ der Substitution von Selen und Vitamin E auf Herzinsuffizienz and ventrikuläre Herzrhythumusstörugen bei Patienten mit akutem Myokardinfarkt," *Medizinische Klinik*, vol. 94, Suppl. III pp. 78-80 (1999).

Westendorp, M. O. et al., "HIV-1 Tat potentiates TNF-induced NF-kB activation and cytotoxicity by altering the cellular redox state," *The EMBO Journal*, vol. 14, No. 3, pp. 546-554 (1995).

Whittington, R., et al., "Interleukin-2; A Review of its Pharmacological Properties and Therapeutic Use in Patients with Cancer," *Drugs*, vol. 46, No. 3, pp. 446-514 (1993).

Yang, S.H., et al., "Internal Cleavage of Hepatitis C Virus NS3 Protein is Dependent on the Activity of NS34A Protease," Virology, vol. 268, pp. 132-140 (2000).

Yao, N., et al., "Helicase, a target for novel inhibitors of hepatitis C virus," *Antiviral Therapy*, vol. 3, pp. 93-97 (1998).

Fakih, Sarah, et al., "Novel Adducts of the Anticancer Drug Oxaliplatin with Glutathione and Redox Reactions with Glutathione Disulfide," *Eur. J. Inorg. Chem.*, (2003), pp. 1206-1214.

Bishop, et al. "A Pilot Study of the Effect of Inhaled Buffered Reduced Glutathione on the Clinical Status of Patients With Cystic Fibrosis," *Amer. College of Chest Physicians.*, (2005), vol. 127, pp. 308-317.

Johnson, "Similarities in the Suppression of the Immune Response by Interferon and by a Thiol-Oxidizing Agent," *Proc. Soc. Exp. Biol. Med.*, 1980, 164:380-385.

Mihm, "Modulation of Transcription Factor NFχB Activity by Intracellular Glutathione Levels and by Variations of the Extracellular Cysteine Supply," *FEBS J.*, 1995, 9:246-252.

Sato, "Thiol-Mediated Redox Regulation of Apoptosis," *J. Immunol.* 1995, 154:3194-3203.

*Primary Examiner*—Jeffrey Edwin Russel
(74) *Attorney, Agent, or Firm*—Wolf, Greenfield & Sacks, P.C.

(57) ABSTRACT

The present invention relates to a composite for the treatment of a variety of medical conditions, the composite comprising an oxidized glutathione-based compound, which has a disulfide bond, and a metal material, in particular where the metal is either platinum or palladium. The oxidized glutathione-based compound and metal material can be present in a ratio of 3000 to 1 and preferably 1000 to 1. The oxidized glutathione-based compound can be oxidized glutathione itself or salts or derivatives. A feature of the invention is that the composite has a more stabilized disulfide bond than the oxidized glutathione-based compound itself. Methods for preparing the composite are provided, such methods being beneficial in that the composite is provided in high yields and at high purity. Methods for treating various medical conditions with the composites of the present invention are also disclosed.

20 Claims, 26 Drawing Sheets

GSSG pharmacokinetic curve for intravenous introduction

GSSG·Pt pharmacokinetic curve for intravenous introduction

Chart 2: Drug Activates Immune System to Fight Cancers and Disease

STEM CELLS

Drug stimulates the immune system to release blood growth factors which causes new blood cells to form in the body

Platelets (Thrombocytes)
Promote blood clotting

White Blood Cells
Major Cells of the Immune System (Leukocytes)

Immune system cells that defend against invaders: germs, micro-organisms and cancer cells, Strategy: to recognize enemy, mobilize forces and mount attack

Cytokines
Proteins secreted by immune system cells

Drug stimulates release of cytokines from white blood cells that send messages to white blood cells to proliferate and attack invaders or suppress attack

Red Blood Cells (Erythrocytes)
Carry oxygen from lungs to organs and carbon dioxide from organs to lungs

Erythropoietins
Promote formation of new erythrocytes

Drug stimulates production of hormone erythropoietin that stimulates the bone marrow to produce new red blood cells

T-Lymphocytes
Fight viral infections and can detect and destroy cancer cells with killer cells

Neutrophils
Ingest antigens and other substances and protect the body against infections

Monocytes
Ingest dead or damaged cells and defend against infective organisms in the blood

Macrophages
Ingest and destroy microbes, antigens and cancer cells in tissue

Natural Killer Cells
Kill microbes and cancer cells

B-Lymphocytes
Produce antibodies

Fig. 26

Chart 3: Cytokines Stimulated by Drug | Cytokines Stimulated by drug

| Interleukin-1 (IL-1) | Interleukin-2 (IL-2) | Interleukin-4 (IL-4) | Interleukin-6 (IL-6) | Interleukin-8 (IL-8) | Interleukin-10 (IL-10) | Interleukin-12 (IL-12) | Interferon alpha and gamma | TNF-alpha | GM-CSF |
|---|---|---|---|---|---|---|---|---|---|
| Is produced by monocytes, macrophages and dendritic cells. | Is produced by lymphocytes. It is a T-cell growth factor | Is released by T helper cells of the TH2 subtype and is particularly active | Is secreted by monocytes, macrophages and bone marrow cells. It | Is a powerful chemotactic factor for neutrophils. Macrophages and | suppresses cytokine production from T cells and macrophages it exerts complex | Is secreted by B cells and macrophages and acts in synergy with IL-2 to activate | activates cells effective in treating several forms of hepatitis, genital | destroys cancer cells, but does not hurt healthy cells. Tumors injected | stimulates the production of neutrophils and is given to patients |
| It activates lymphocytes and there by regulates | and stimulates lymphocytes that have already been activated | on resting and active B cells. On resting B cells and on macrophages | acts on proliferating B cells to promote differentiation into plasma cells and it | endothelial cells secrete IL-8 in order to attract neutrophils and allow them to | regulatory effects on CD8+ T cells, Natural Killer cells, vascular endothelial | cytotoxic T cells. Natural Killer cells and TH1 cells are also stimulated to | warts, Kaposi's sarcoma, hairy cell leukemia and malignant melanoma. | with TNF-alpha hemorrhage, soften and turn black. Macrophages begin | who have low numbers of neutrophils due to chemotherapy. |
| Immune responses usually associated with non-specific Immune response | by cancer antigens so only those lymphocytes that recognize cancer | IL-4 increases MHC II expression. On activated B cells, proliferation and | stimulates antibody secretion. Myeloid stem cells are helped to differentiate | adhere to vascular endothelial cells. This helps neutrophils marginate and enter | cells and B lymphocytes. IL-10 plays an important inhibitory | proliferate by IL-12. | In 1996, Biogen received FDA approval to market AVONEX for multiple sclerosis. | to pump-out huge amounts of TNF when they are recruited to the scene | |
| of infection and inflammation, and fever. | cells would receive IL-2's chemical message to expand. For example, | differentiation is stimulated and an antibody class switch is induced | by IL-6. It also strongly stimulates hepatocytes to make acute phase proteins | the tissue where they are needed, especially during inflammation and | role and acts on macrophages to inhibit cytokine production to downregulate | | | of injury or infection. | |
| | T-lymphocytes exposed to malignant melanoma | A B cell stimulated with IL-4 alone becomes a plasma cell secreting IgE | in response to inflammation. This cytokine is always found in increased | infection. Neutrophils are the first line of defense against invading bacteria | TH1 type of T helper cells. It is released by TH2 helper cells and also | | | | |
| | or kidney cancer have been retrieved from the body and exposed in the lab | and other allergy-related antibodies. IL-4 acts with IL-10 in an immuno- | levels in sites of inflammation and is likely very important in a | and are found in all areas of infection. | downregulates MHC II expression on antigen presenting cells. It interacts with IL-4 | | | | |
| | to IL-2 to create lymphocyte-activated killer cells which are re-injected into | regulatory manner to decrease the activity of activated macrophages. | number of undescribed ways in inflammatory regulation. | | to decrease macrophage inflammatory activity. | | | | |
| | the body, then killer cells will attack the cancer and destroy it. | | | | | | | | |

Fig. 27

METHODS FOR PRODUCTION OF THE OXIDIZED GLUTATHIONE COMPOSITE WITH CIS-DIAMMINEDICHLOROPLATINUM AND PHARMACEUTICAL COMPOSITIONS BASED THEREOF REGULATING METABOLISM, PROLIFERATION, DIFFERENTIATION AND APOPTOTIC MECHANISMS FOR NORMAL AND TRANSFORMED CELLS

RELATED APPLICATIONS

This application is a continuation of U.S. application Ser. No. 10/747,855, filed Dec. 29, 2003 (now U.S. Pat. No. 7,169,412 B1), which is a continuation of U.S. application Ser. No. 10/404,914, filed Apr. 1, 2003 (now abandoned), which is a continuation of U.S. application Ser. No. 09/842,104, filed Apr. 30, 2001 (now abandoned), which is a continuation of U.S. application Ser. No. 09/241,232, filed Feb. 1, 1999 (now U.S. Pat. No. 6,312,734 B1), which is a continuation-in-part of U.S. application Ser. No. 09/237,801, filed Jan. 27, 1999 (now abandoned), which claims priority to RU 98-120753, filed Nov. 23, 1998. Each of these applications is incorporated herein by reference.

FIELD OF THE INVENTION

The present invention relates to medicine and, more particularly, to pharmacology, i.e., to methods for producing medicinal agents based on a composite comprising an oxidized glutathione composite and a platinum material, in particular cis-platin, that are intended to be used for preventing and treating various pathologic syndromes and diseases by way of differentiated influence on processes of metabolism, proliferation, differentiation and apoptosis of normal and transformed cells.

BACKGROUND OF THE INVENTION

Certain issues in modern pharmacological industry involve counteracting two medical-biological problems:
forming a resistance (tolerance and pharmacological efficacy decrease) to medicinal agents including cases due to activation of the MDR-genes system; and
forming of undesirable resorptive effects manifested, first of all, by alteration of the immunocompetent cell system and hemopoiesis; cardio-, hepato-, nephro- and neurotoxicity.

A typical cause for these problems is a wide administration of chemotherapeutic agents that can be quite effective, according to their physical-chemical properties, but can also be foreign to an organism at their very nature. Even genetic-engineering medicines, in spite of human genes (DNA) application as a matrix for multiplication, use single-celled organisms (Escherichia coli, yeast cells) that bring in their own, and therefore, xenobiotic contribution into obtained drugs.

Theoretical and practical medicinal research are now paying greater attention to natural key metabolites, i.e., key factors (low molecular biochemical substances) that are naturally determined to trigger chain reactions for endogenous production and modification of many biologically active products for physiologically important and adequate processes. In some cases these biochemical substances function as "biochemical gyroscopes" assigned to restoring the balance of altered equilibrium of basic metabolic processes, for example, anabolism and catabolism or proliferation and differentiation. Alteration of the balance of these vital mechanisms can lead to cell destruction (cytolytic syndrome) or their transformation into malignant ones, i.e., cancer. As a rule, the key regulatory metabolites, i.e., "cellular hormones", are peptide origin factors (usually not larger than 3-20 amino acids). Obtaining synthetic analogues (biochemical substances) and, therefore, drugs with predetermined properties is a desired goal because these drugs are optimal as metabolic therapy instruments and, in fact, are not foreign to the organism.

Ideal peptide structures that can function as these synthetic analogues include sulphur-containing peptides and derivatives thereof, due to the presence of a thiol group. In particular, biological effects of the tripeptide "reduced glutathione" (γ-glutamyl-cysteinyl-glycine; hereinafter—GSH) are known to be researched extensively. The glutathione tripeptide dimer, oxidized glutathione (γ-glutamyl-cysteinyl-glycine; hereinafter—GSSG), where two molecules of the tripeptide with the aforementioned formula are linked via a covalent bond between cysteine residues, is also well known.

Administration of the exogenous synthetic GSSG analogue is known to induce cytokine and hemopoietic factor synthesis during in vitro experiments, and to provide the setting of the cytokine profile to normal values in conditions of cyclophosphamide and radiation immunodepression models (in vivo experiments) along with the immunity and hemopoietic system restoration (International application WO 97/21444, MKI A61к 38/02, published 19 Jun. 1997).

In their turn, the exogenous GSSG drug forms applied to severe immunodeficient conditions and suppressed bone marrow hemopoiesis containing chemical examples relating to clinical Examples in the International Application on AIDS patients, patients with oncopathology, aplastic anemia, and other conditions at treatment courses of different durations, can provide a curative effect in restoring the organism immune status (including antitumor immunity indices), immunogenesis and hemopoietic functional activity (International application WO 97/21444, MKI A61к 38/02, published 19 Jun. 1997).

Previously, the thiol class of biologically active substance had applications aimed to provide GSH at increased levels, i.e., to obtain antioxidant effects. In addition, pharmacological activity was observed, namely, for the pro-oxidant effect gaining and forming of a new intracellular redox-balance by introduction of GSSG that possesses pro-oxidant potential into an organism. This is the only known case of triggered redox-sensitive mechanisms for immunologically significant genes, activation of the cellular thiol metabolism, and therefore, beneficial pharmacological properties were provided including systemic cell-protective effects and immunity state regulation depending on initial cell status: immunodeficiency, i.e., hyporeactivity, immunoautoaggression, i.e., hyperreactivity.

International Application WO 97/21444,MKI A61к 38/02, published 19 Jun. 1997, is directed to gain a set of technical and pharmaceutically acceptable solutions effective for the prevention of the GSSG reduction into GSH and, thus, for extending the lifetime of GSSG as the oxidized form in biological media. Attainment of the biological-pharmacological effects of the glutathione oxidized form is proven by the biomedical investigation results obtained in the course of the complex and extensive preclinical and clinical studies program on synthetic GSSG analog effectiveness. A strategy for extending the lifetime of oxidized GSSG includes providing: salts thereof, composite drugs including GSSG combinations with substances that prolong or enhance the effect of GSSG or salts thereof, or derivatives as a new composite, i.e., a mixture of oxidized GSSG and other materials. The pharmaceutically acceptable GSSG derivative in the form of the salts thereof, or combinations with extenders of the GSSG existence in the oxidized form, or GSSG combinations with enhancers/modifiers, i.e., all technical solutions stabilizing in the varying degree the GSSG molecule disulfide form were first demonstrated to be significantly more effective in inducing the cytokine and hemopoietic factor production in normal conditions and to a greater degree in pathologic ones.

GSSG derivative drug forms are characterized with a larger fraction of the GSSG stabilized in the disulfide form, with maximal pharmacokinetics in biological media. These forms manifested the following features:

a) Inducting production of a wider range of cytokine and hemopoietic factors that can determine the presence of largely modulating effects rather than only stimulating ones.

b) Reproduction of particular cytokine effects, for instance, IL-2.

The events developing in cells (tissues and, therefore, organs) after interaction with cytokines is well known. These events are conditioned by the universal cytokine influence on the main signal-transducing systems and, through the latter, on the cell genome determining regulating cytokine effects on proliferation, differentiation, and apoptosis.

Methods for obtaining the oxidized GSSG form from the reduced GSH precursor are well known. The labile mercapto-SH-groups of cysteine in GSH can be oxidized with such soft oxidizers as air oxygen (R. Douson, D. Elliot, W. Elliot, K. Jones. Biochemist's manual, Moscow, "Mir", 1991; Tam J. P. et al., Int. J. Pept. Prot. Res., Vol. 29, p. 421-431, 1987; Ahmed A. K. et al., J. Biol. Chem. 250, p. 8477-8482, 1975). However, the reaction rate is rather low in this case and desired quantitative yields require very long periods of time (many days). Catalysis by heavy metals ions and, especially, by copper can be toxic, and can create significant problems for obtaining pure pharmaceutical medicines.

Another oxidation method involves more potent oxidizers such as, hydrogen peroxide, iodine, potassium ferrocyanide, etc. (Kamber B. et al., Helv. Chim. Acta., Vol. 63, p. 899-915, 1980; Hope D. B. et al., J. Biol. Chem., Vol. 237, p. 1563-1566, 1962). These reactions generally proceed much faster (dozens of minutes to several hours). A disadvantage, however, is a difficulty in controlling reaction conditions that can result in significant contamination of the product with oxidation products, e.g., derivatives of the corresponding acids. It is sometimes necessary to add additional, sometimes rather labor-consuming purification procedures, that can sharply appreciate the process.

Yet another oxidation method involves the use of gaseous substances (nitrogen oxides), sulfoxides and other compounds as oxidizers. These oxidizers, however, can be toxic. (William A. Kato et al., Chem. Pharm. Bull., vol. 34 (2), p. 486-495, 1986; A. Meister et al., Ann. Rev. Biochem., p. 711-718, 1983.)

All these methods do not necessarily improve the quantitative yield of the desired product compared to older methods, and at the same time, can provide additional problems regarding toxicity and safety, as in case of nitrogen oxides, or more difficult accessibility of the reagents and their high cost.

Another previously known method involves the use of hydrogen peroxide as an oxidizer (Amber B. et al., Helv. Chim. Acta., Vol. 63, p. 899-915, 1980). The process is performed in the water solution with pH about 8.0-8.5 using the hydrogen peroxide equivalent at the room temperature. The reaction time is about 1 hour and the product yield is 90%. The main impurities (up to 10%) are other oxidation products, which can be removed only by means of an expensive preparative HPLC separation that can sharply increase the drug cost.

SUMMARY OF THE INVENTION

The present invention involves the creation of new pharmaceutically acceptable compounds with predetermined properties based on GSSG, i.e., an oxidized glutathione-based compound having a stabilized disulfide bond. The present invention also provides a new method for obtaining the oxidized glutathione as a composite with the stabilized disulfide bond during the product synthesis. The method involves the production of the composite having the formula: bis-(γ-L-glutamyl)-L-cysteinyl-bis-glycine disodium salt with a platinum material such as cis-platin, i.e., cis-diamminedichloroplatinum, preferably in the mole ratio 3000:1, more preferably in a mole ratio of 1000:1.

According to the invention the composite is characterized as having a stabilized disulfide bond. Upon introduction into biological media, consequently, a longer drug half-life time is provided in the biological media in the disulfide form.

The general procedure of the present method for the composite production involves using the reduced glutathione for the oxidation reaction as a hydrogen peroxide oxidizer combined with a platinum material, in particular, cis-diamminedichloroplatinum, as a catalyst. The method allows using lesser amounts of hydrogen peroxide (for example, 0.9 of an equivalent), resulting in an elimination of the superoxidation products along with very high yield for GSSG (more than 98% by the HPLC data). Thus, the product obtained has high purity and does not require additional purification.

One aspect of the present invention provides a composite comprising an oxidized glutathione-based compound and a metal material in a ratio between about 3000:1 to about 1:1. The metal material comprises a metal selected from the group consisting of platinum and palladium.

Another aspect of the invention provides a method for stabilizing a disulfide bond of an oxidized glutathione-based compound. The method comprises interacting the oxidized glutathione-based compound with a metal material. The metal material comprises a metal selected from the group consisting of platinum and palladium.

Another aspect of the present invention provides a method of stimulating endogenous production of cytokines and hemopoietic factors. The method comprises the steps of introducing to a mammalian body, in need of stimulation of cytokines or hemopoietic factors or both, an effective amount of a composite. The composite comprises an oxidized glutathione-based compound and a metal material in a ratio of between about 3000:1 to about 1:1. The metal material comprises a metal selected from the group consisting of platinum and palladium. The method is carried out for a period of time to stimulate the endogenous production to obtain a therapeutic effect.

Another aspect of the present invention provides a method for enhancing and prolonging the ability of an oxidized glutathione-based compound to stimulate endogenous production of cytokine and hemopoietic factors. The method involves the steps of interacting the oxidized glutathione-based compound with a metal material in a ratio of between about 3000:1 to about 1:1. The metal material comprises a metal selected from the group consisting of platinum and palladium.

Another aspect of the present invention provides a method for treating a subject having a disease. The method comprises administering to the subject in need of such treatment a composite comprising an oxidized glutathione-based compound and a metal material in a ratio of between about 3000:1 to about 1:1 in an amount effective to stimulate endogenous production of cytokines and/or hemopoietic factors or both to obtain the therapeutic effect. The metal compound has a metal selected from the group consisting of platinum and palladium.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 26 shows a chart of drug activation of immune systems to fight cancers and diseases; and FIG. 27 shows a chart of cytokines stimulated by drug-type.

DETAILED DESCRIPTION

Figure 1:
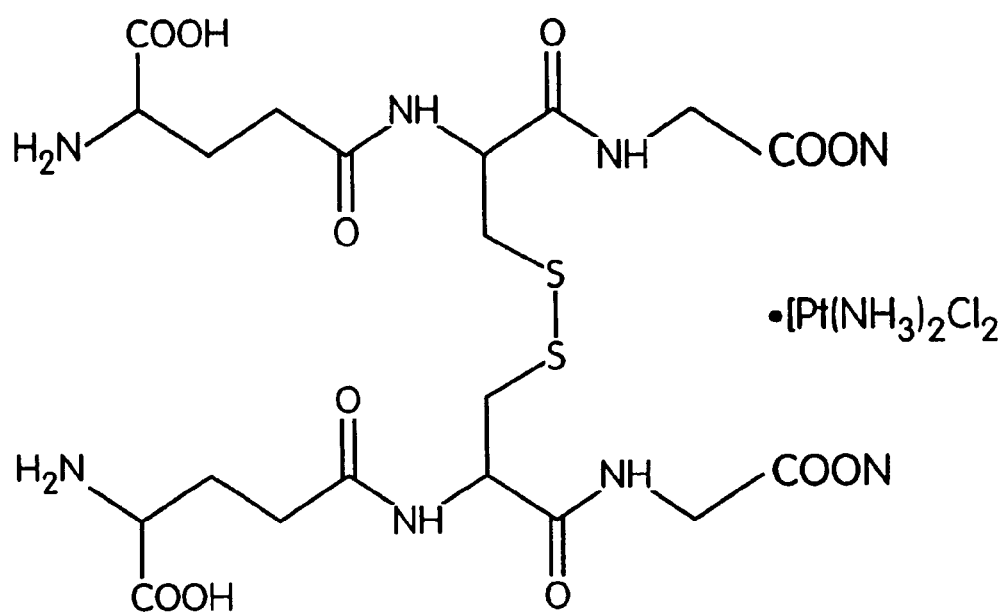
FIG. 1 shows the structure of bis-(γ-L-glutamyl)-L-cysteinyl-bis-glycine disodium salt with cis-diamminedichloroplatinum.

The present invention discloses a number of oxidized glutathione-based compounds having a stabilized disulfide bond and in particular, a composite comprising the compound of this invention with a metal material. Methods for the preparation of a composite and for using the composite to treat a variety of diseases are also disclosed.

One aspect of the present invention provides a composite comprising an oxidized glutathione-based compound and a metal material. Generally, a "composite" can refer to a mixture of different chemical species. The "mixture" can be a physical mixture or a chemical mixture, i.e., having a chemical interaction involving either a chemical bond or an electrostatic interaction. In one embodiment, the mixture can be prepared by dissolving and/or suspending the different chemical species in a solution and precipitating out or filtering out a resulting solid. In another embodiment, the mixture can be a homogeneous solution comprising the different chemical species.

An "oxidized glutathione-based compound" refers to any compound having a basic dimer structure where each unit of the dimer comprises a glutamic acid group or salt or derivative bonded to a cysteine group or salt or derivative bonded to a glycine group or salt or derivative, and each unit is correspondingly bonded to each other by the cysteine sulfur atoms to form a sulfur-sulfur bond (disulfide bond). A "derivative" can be prepared by reacting at least one reactive group of the oxidized glutathione-based compound or precursor with another chemical species. An example of an oxidized glutathione-based compound is GSSG itself. Other examples are provided below.

In one embodiment, the oxidized glutathione-based compound has the general formula:

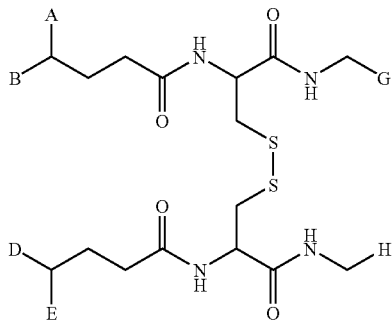

A, B, D, E, G and H can each be selected from the group consisting of an organic unit and salts of the organic unit. Preferably, the "organic unit" allows the glutathione-based compound to remain soluble in biological media and in addition, the organic unit should not impart toxicity to the oxidized glutathione-based compound in an applied dosage. It is understood that A, B, D, E, G and H can be the same or different. Preferably, groups A-H can each include a unit selected from the group consisting of amine groups, carboxyl groups, and amides. For example, A-H can represent amino acids or derivatives bonded via an amide bond. Alternatively, any two of A-H can be linked to each other by at least one covalent bond. Thus, A-H can be part of a cyclic structure.

In one embodiment, the composite comprises a large excess of the oxidized glutathione-based compound relative to the metal material, preferably in a ratio of between about 3000:1 and 1:1, more preferably in a ratio of between about 1000:1 and 1:1, more preferably in a ratio of between about 1000:1 and 10:1, even more preferably in a ratio of between about 1000:1 and 100:1. In another embodiment, the composite comprises equal amounts of the oxidized glutathione-based compound and the metal material, i.e., a ratio of about 1:1.

Figure 3:
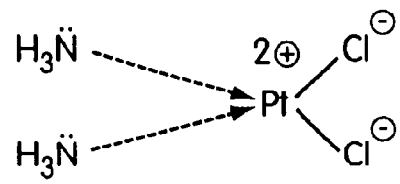
FIG. 3 shows the donor-acceptor bond among platinum atom and two $NH_3$ groups due to the lone-pair electrons of nitrogen atoms.

In one embodiment, the metal material comprises a metal selected from the group consisting of platinum and palladium. Preferably, the metal is platinum. Ideally, the metal material, in combination with the oxidized glutathione-based compound, renders the composite soluble in biological media. Small portions of the metal material can be insoluble, as long as the insoluble portion does not result in any toxic or hazardous effects to the biological system. A platinum material can be selected from the group consisting of a platinum salt, a coordination compound and an organometallic compound. Preferably, the platinum material is a platinum coordination compound such as cis-platin (cis-Pt $(NH_3)_2Cl_2$ or cis-diamminedichloroplatinum—FIG. 3).

In one embodiment, the oxidized glutathione-based compound is oxidized glutathione itself (GSSG) and salts thereof, where both A and E are —$CO_2H$, both B and D are —$NH_2$ and both G and H are —$CO_2M$, M being a counterion. The counterion can be a proton, an organic-based ion such as tetralkyl-amononium, an alkaline metal, an alkaline earth metal, or a transition metal. It is understood that in aqueous media, any of A-H can comprise an ionized group, e.g., A and E can be —$CO_2^-$, and B and D can be —$NH_2^+$ and the ionized groups are neutralized by an appropriate counterion.

In a preferred embodiment, the present invention relates to the production of a new biologically active compound, i.e., a composite comprising an oxidized glutathione-based compound and cis-diamminedichloroplatinum. A convenient short-form notation will be used herein. For example, a composite comprising GSSG itself and cis-platin will be denoted as GSSG.Pt. Derivatives will be denoted by the newly appended chemical group, e.g., bis-[histidyl]-GSSG. While not wishing to be bound by any theory, a proposed structural formula can be found in FIG. 1. (Gross-formula: $C_{20}H_{30}N_6O_{12}Na_2S_2 \cdot [Pt(NH_3)_2Cl_2]$; molecular weight: 656.59 on $C_{20}H_{30}N_6O_{12}Na_2S_2$ with Pt content 0.022-0.042%.)

The composite can be prepared by various methods. For example, the composite can result from the addition of a metal material to glutathione in the presence of an oxidant. Alternatively, the composite can result by the addition of a metal material to the oxidized glutathione-based compound.

Thus, another aspect of the invention provides a method for stabilizing a disulfide bond of an oxidized glutathione-based compound. "Stabilizing a disulfide bond" refers to a process for maintaining a bond between two sulfur atoms and preventing facile reversion of the oxidized glutathione-based compound (e.g., GSSG) back to the reduced form (e.g., GSH). Alternatively, stabilizing the disulfide bond can result in an increased lifetime of the oxidized glutathione-based compound. In the presence of reductants, the disulfide bond can cleave resulting in formation of the reduced form of the glutathione-based compound, which is an undesired reaction. By maintaining the glutathione-based compound in an oxidized form for a greater amount of time, the compound can be pharmaceutically effective for a correspondingly longer period of time in biological media.

In one embodiment, the disulfide bond can be stabilized by interacting the oxidized glutathione-based compound with a metal material. As discussed previously, the metal material is preferably a platinum or palladium material, such as cis-platin. In one embodiment, the platinum material is present in an amount of between about 0.0003 equivalent to about 1 equivalent relevant to the oxidized glutathione-based compound, preferably in a ratio of between about 0.001 equivalent to about 1 equivalent relevant to the oxidized glutathione-based compound.

In one embodiment, "interacting the oxidized glutathione-based compound with a metal material" comprises providing a glutathione-based compound and reacting this compound with an oxidant and a platinum material. A "glutathione-based compound" refers to any compound having a structure comprising a glutamic acid/salt/derivative bonded to a cysteine/salt/derivative bonded to a glycine/salt/derivative. Examples of glutathione-based compound include glutathione itself or any derivative, where a derivative can be prepared by reacting a reactive group with another chemical species. The resulting product will be an oxidized glutathione-based compound having a stabilized disulfide bond. Thus, in this embodiment, a glutathione-based compound is in a reduced form, such as GSH, and the reaction with a oxidant involves oxidizing the glutathione-based compound to produce a sulfur-sulfur bond. The oxidant can be any species which can cleave a S—H bond of a glutathione-based compound to produce a hydrogen atom and a compound having a sulfur-based radical which ultimately can react with another sulfur-based radical to provide the sulfur-sulfur bond. Various oxidants that can perform this S—H bond cleavage are well known in the art. In a preferred embodiment, the oxidant is selected from the group consisting of oxygen and hydrogen peroxide.

In this method, reacting a glutathione-based compound with an oxidant and the platinum material comprises an oxidation reaction. Relative amounts of the reactants are preferably about 1 equivalent of the glutathione-based compound with less than about 1 equivalent of the oxidant such as hydrogen peroxide, and more preferably, with about 0.9 equivalent of the hydrogen peroxide. In another embodiment, the oxidation reaction comprises reacting about 1 equivalent of the glutathione-based compound with between about 0.0003 equivalent and about 1 equivalent of the platinum material, preferably between about 0.001 equivalent and about 1 equivalent of platinum material, more preferably between about 0.001 equivalent and about 0.1 equivalent, and even more preferably between about 0.001 equivalent and 0.01 equivalent, in the presence of less than 1 equivalent of the oxidant. In another embodiment, about 1 equivalent of the glutathione-based compound is reacted with about 1 equivalent of the platinum material in the presence of less than 1 equivalent of the oxidant.

In one embodiment, the method involves oxidizing the glutathione-based compound with about 0.9 equivalent of hydrogen peroxide and about 0.001 equivalent of cis-platin. One advantageous feature of this method is an increased rate of oxidation of the glutathione-based compound. Another advantageous feature of this method is that the yield of the resulting composite is increased to an amount greater than about 98% and this increased yield is accompanied by an increased purity. The purification of this composite is simplified to a significant degree in that liquid chromatography can be performed to obtain a purity of the composite of greater than 99%, which complies with pharmaceutical standards. Prior art methods have achieved a purity of only 75-93% of oxidized glutathione, depending on the method.

In a preferred embodiment, the composite is synthesized in one step by oxidizing the reduced glutathione in the presence of cis-diamminedichloroplatinum, which may function as an oxidation reaction catalyst. The reaction conditions can be regulated accurately by using less than 1 equivalent of hydrogen peroxide. Consequently, formation of superoxidation products can be reduced, resulting in a near quantitative yield of the product. Thus, the one-step composite synthesis provides significant technological simplification and production of the composite GSSG.Pt with the stabilized disulfide bond.

In a preferred embodiment, the reaction is performed in a solution involving reduced glutathione as a monosodium salt and adding about 0.9 equivalent of the hydrogen peroxide and about 0.001 equivalent of cis-diamminedichloroplatinum at room temperature with stirring. The oxidation reaction typically proceeds in about 1.5-2 hours. Control for the completeness of the oxidation process can be conducted by an HPLC assay. The process is completed by the reaction solution lyophilic drying to produce the composite consisting of oxidized glutathione and cis-diamminedichloroplatinum in a mole ratio of 1000:1 (confirmed by spectral analysis on platinum and sodium). The peptide constituent of the obtained composite according to the data of an amino acid assay, a NMR ($^1$H) spectrum, retention time by HPLC corresponds to GSSG. The admixtures content do not exceed 2%, and the product yield as a disodium salt is 96-98% calculating for the dry composite.

Figure 2:
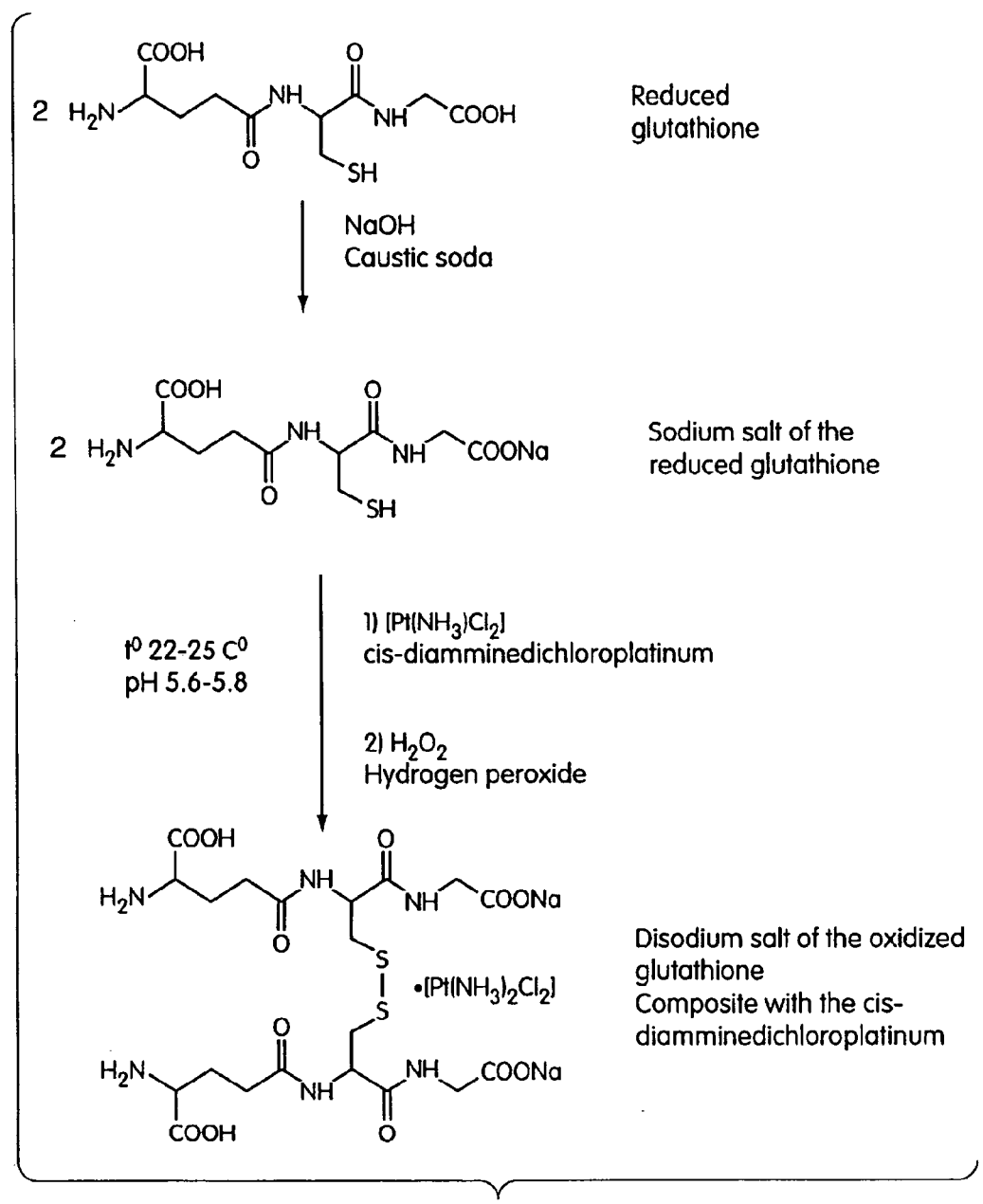
FIG. 2 shows the synthesis scheme of the composite of the oxidized glutathione disodium salt with cis-diamminedichloroplatinum.

A composite synthesis scheme can be found on FIG. 2.

Figure 4:
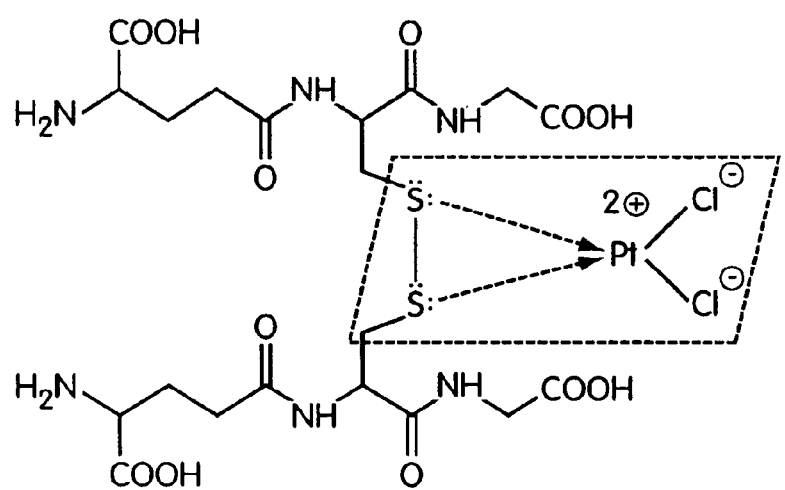
FIG. 4 shows proposed mechanisms for the GSSG molecule disulfide bond stabilization due to the ligand exchange—$NH_3$-groups on disulfide bonds—and through forming of the donor-acceptor bond among platinum atom and two sulfur atoms due to lone-pair electrons of sulfur atoms.

While not wishing to be bound by any theory, the increased stabilization of the disulfide bond can be the result of an interaction of the sulfur atoms with the platinum material (see also FIG. 4).

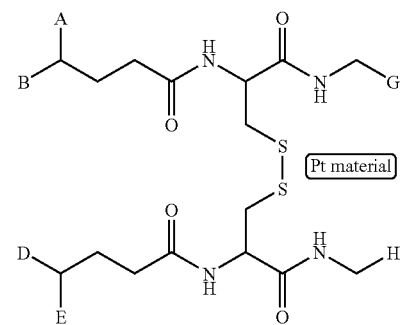

Figure 5:
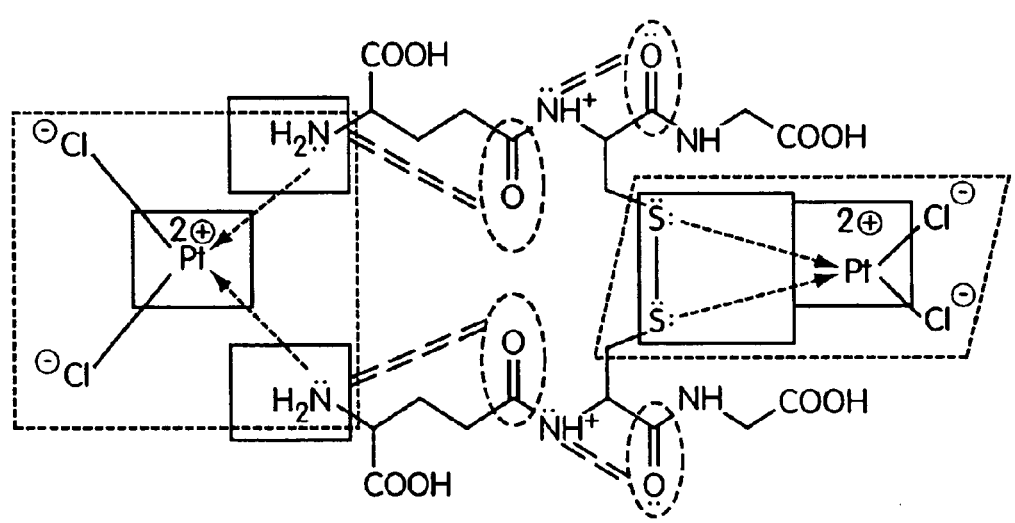
FIG. 5 shows proposed mechanisms of the general GSSG molecule stabilization through the mechanism given at FIG. 4 as well as through exchange of the $NH_3$ ligands on $NH_2$ groups of the glutathione (the $NH_2$ group convergence and the GS fragments, correspondingly) forming new "biophysics" of the GSSG.Pt composite, with squares (□) denoting donor sites and circles (○) denoting acceptor sites.

In an interaction between the platinum material and the oxidized glutathione (GSSG) molecule there is a possibility for ligand exchange, i.e., instead of the NH$_3$ groups, two sulphur atoms possessing two pairs of the lone-pair electrons can be involved in donor/acceptor bonds with the platinum atom. One can also consider the possibility for the addition in regard to the aforesaid stabilization of the disulfide bond due to the convergence of the NH$_2$ groups of the oxidized glutathione-based compound and stabilization of the general GSSG conformation (FIG. 5).

It is an advantageous feature of the present invention that obtaining derivatives of GSSG can produce a compound having different biological/chemical properties and/or activity. Thus, depending on the desired use of a drug comprising a composite including the oxidized glutathione-based compound, it is possible to obtain a particular drug for treatment of a particular disease. In addition, new chemical modifications of the oxidized glutathione-based compound, such as aminogroup acylation (for instance, bis-phenylalanyl-glutathione, and etc.), can result in a significant decrease in the risk of secondary reactions due to disulfide bond destruction. Reactions such as S-alkylation, oxidation to the corresponding acids, etc., can cause particular hardships in the working process and, in the case given, can be minimized or excluded.

The synthetic method of the present invention and physical-chemical modifications thereof directly in the course of the synthesis (the disulfide bond and general molecular conformation stabilization; the new reactive functional sites appearance) can result in obtaining the biologically active composite, such as the platinum material and GSSG, having new biophysical, chemical and biochemical parameters as dictated by the various structural-functional properties.

Figure 15A:
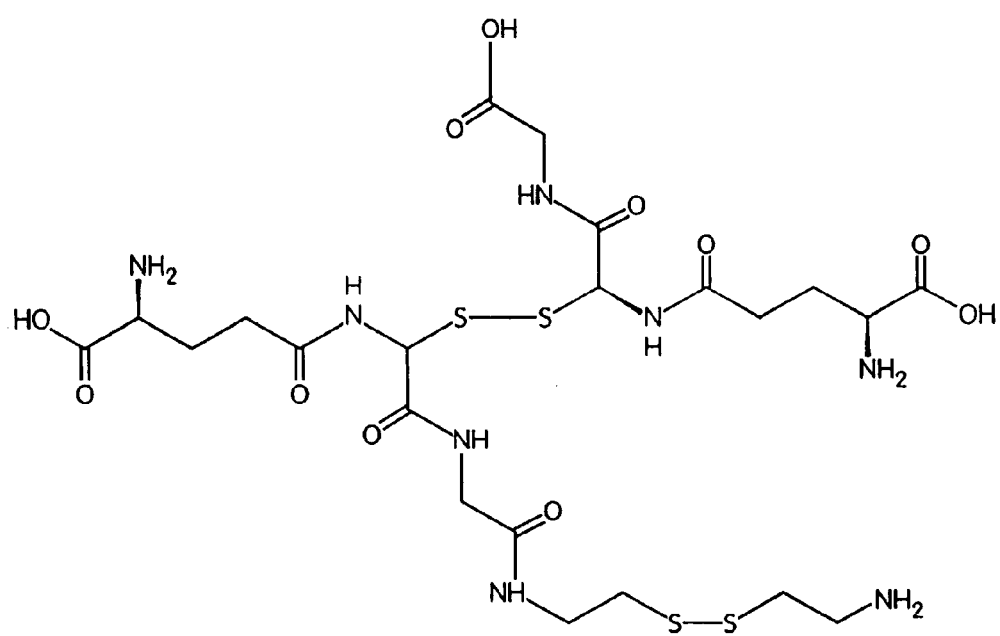
FIG. 15(a) shows the structure of S-thioethylamine.glutathione disulfide.
Figure 15B:
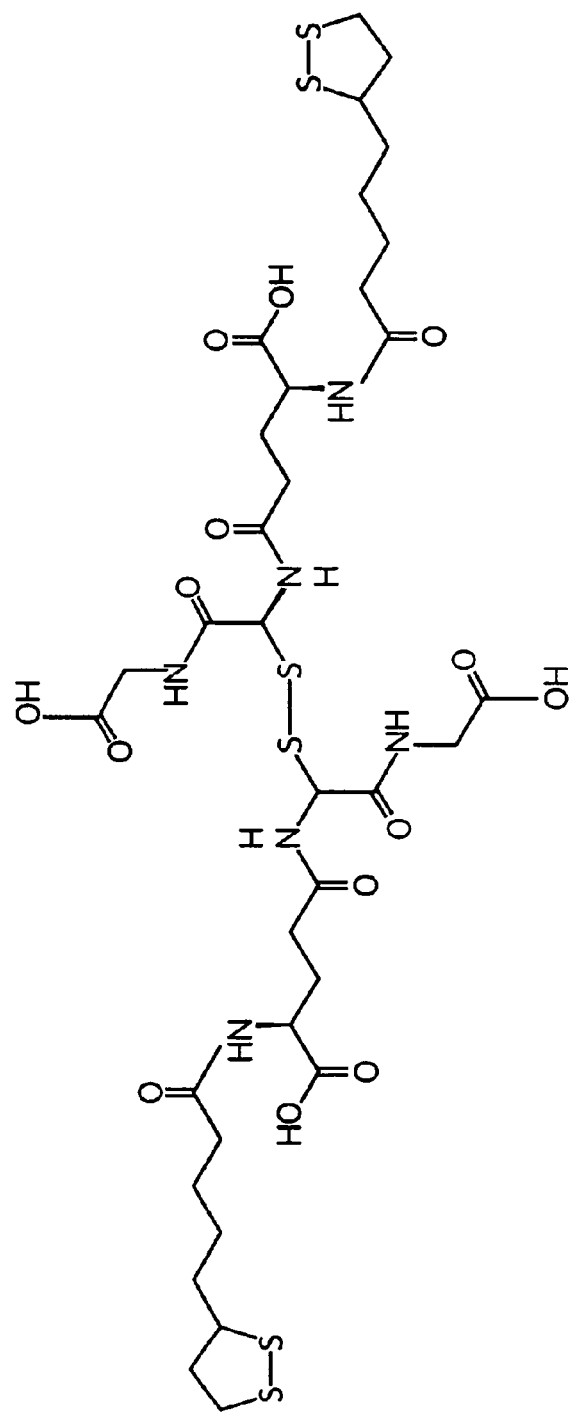
FIG. 15(b) shows the structure of bis-[DL-6,8-thioetic acid].glutathione disulfide.
Figure 15C:
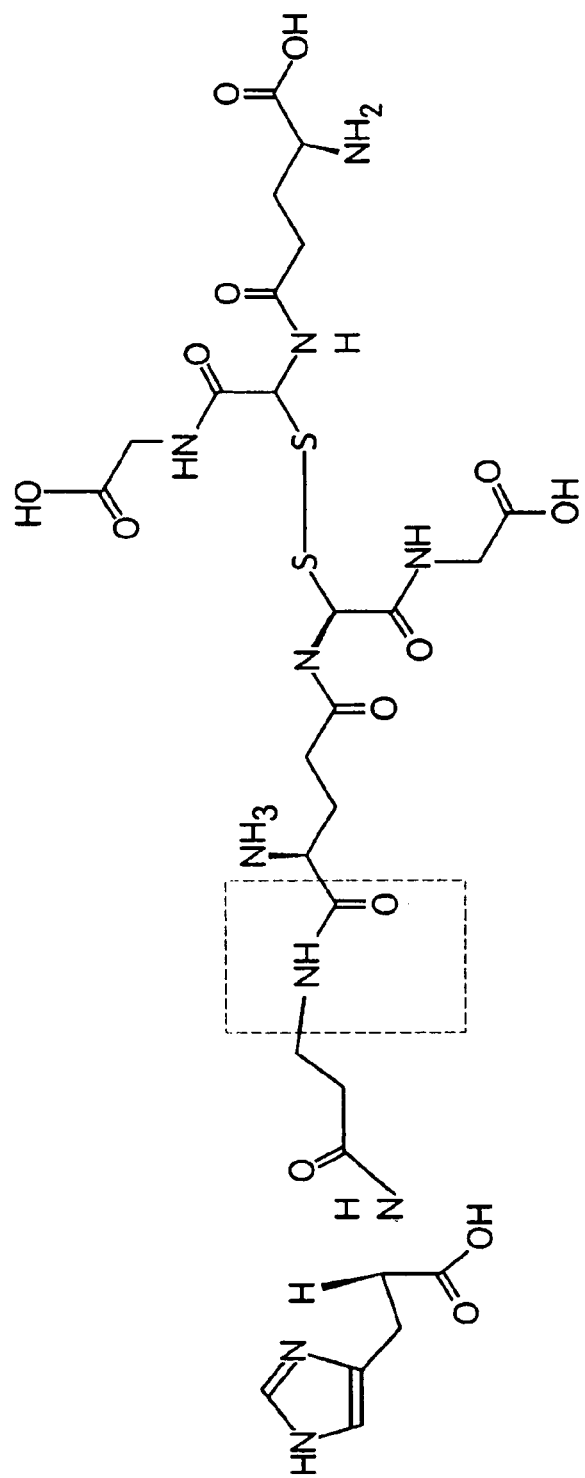
FIG. 15(c) shows the structure of [β-alanyl-L-histidyl].glutathione disulfide.
Figure 15D:
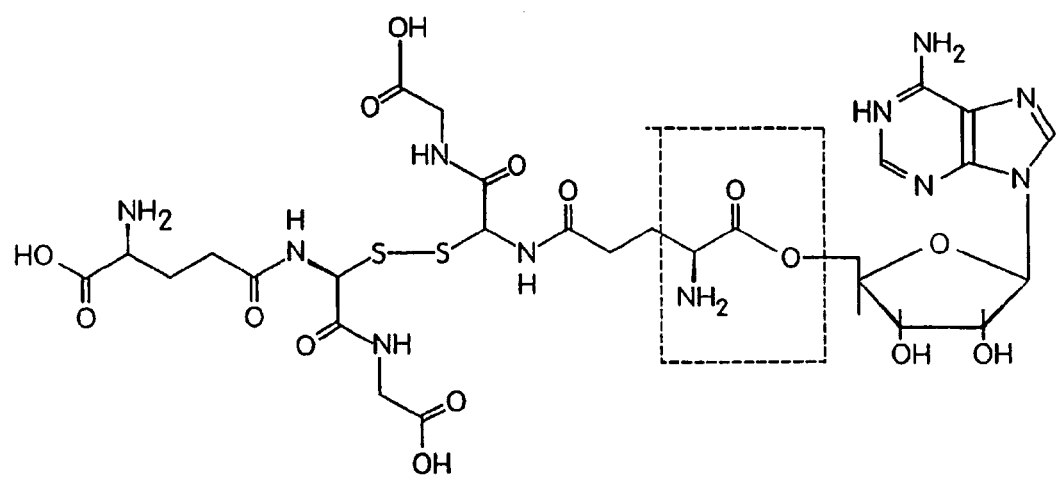
FIG. 15(d) shows the structure of [9-β-D-ribofuranosyladenyl].glutathione disulfide.
Figure 15E:
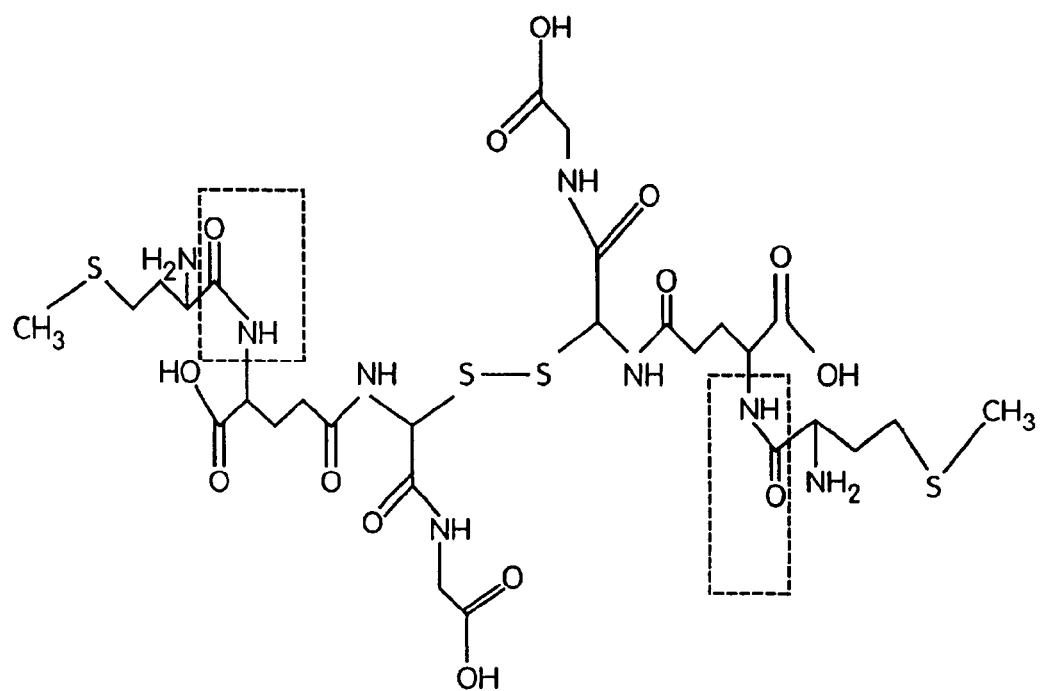
FIG. 15(e) shows the structure of bis-[L-2-amino-4-[methylthio]butanoic acid].glutathione disulfide.

In one embodiment, the oxidized glutathione-based compound can be a derivative of glutathione. The glutathione can be derivatized after preparation of the composite, or it can be derivatized prior to preparation of the composite, i.e., the GSH can be derivatized prior to oxidation. FIG. 15 depict various examples of derivatives of glutathione-based compounds, i.e., oxidized glutathione-based compound. FIG. 15a shows the structure of S-thioethylamine.glutathione disulfide. FIG. 15b shows a structure of bis-[DL-6,8-thioetic acid].glutathione disulfide. FIG. 15c shows a structure of [β-alanyl-L-histidyl].glutathione disulfide. FIG. 15d shows a structure of [9-β-D-ribofuranosyladenyl].glutathione disulfide. FIG. 15e shows a structure of bis-[L-2-amino-4-[methylthio]butanoic acid].glutathione disulfide.

Figure 16A:
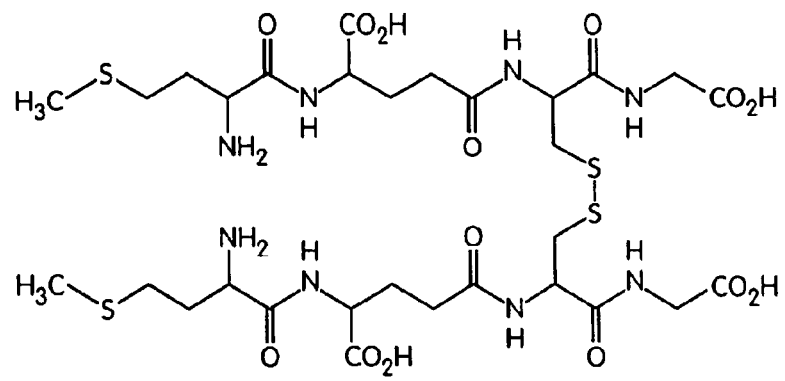
FIG. 16(a) shows the structure of bis-[methionyl].glutathione disulfide.
Figure 16B:
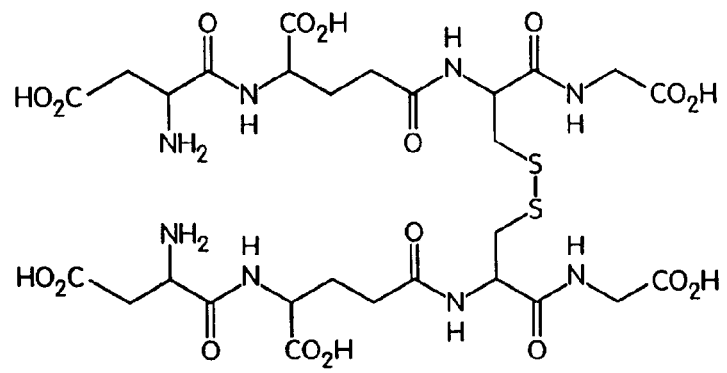
FIG. 16(b) shows the structure of bis-[aspartyl].glutathione disulfide.
Figure 16C:
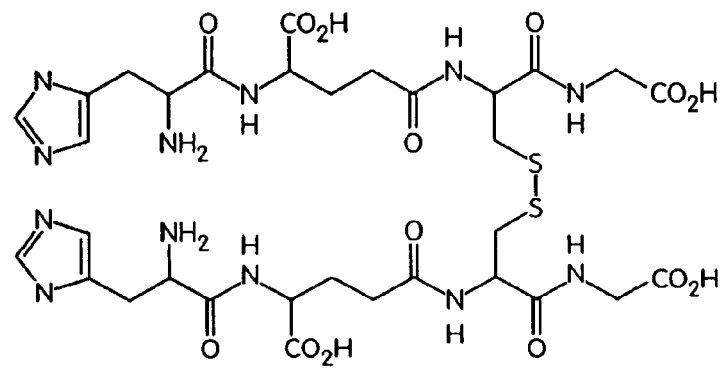
FIG. 16(c) shows the structure of bis-[histidyl].glutathione disulfide.
Figure 16D:
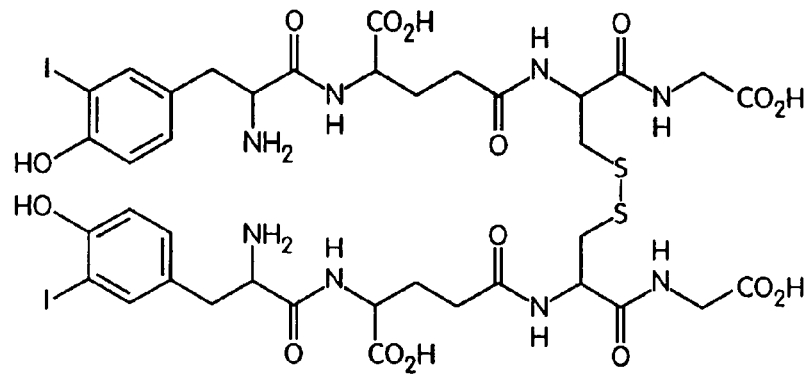
FIG. 16(d) shows the structure of bis-[3-iodine-tyrosyl].glutathione disulfide.
Figure 16E:
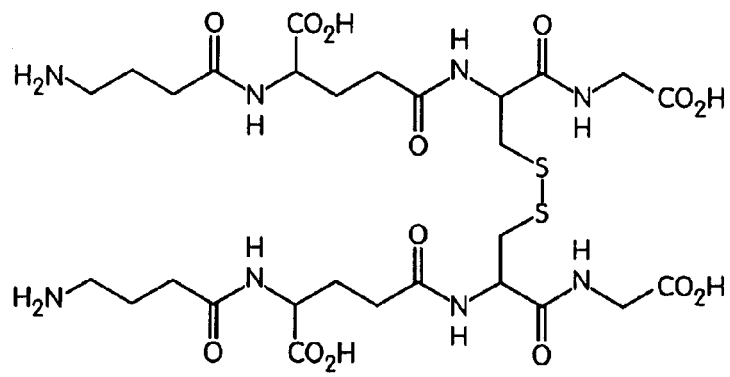
FIG. 16(e) shows the structure of [γ-aminobutanoyl].glutathione disulfide.
Figure 16F:
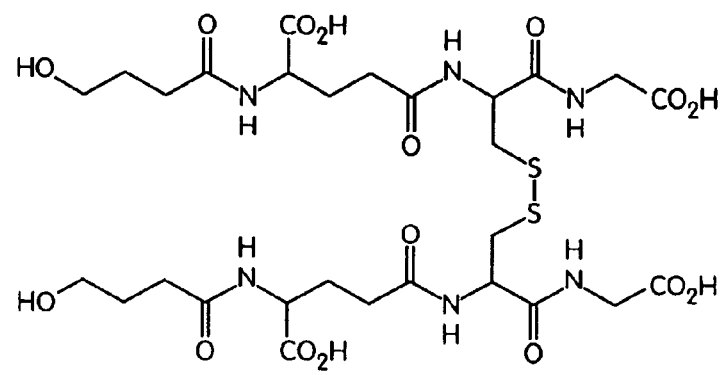
FIG. 16(f) shows the structure of bis-[γ-hydroxybutanoyl].glutathione disulfide.
Figure 16G:
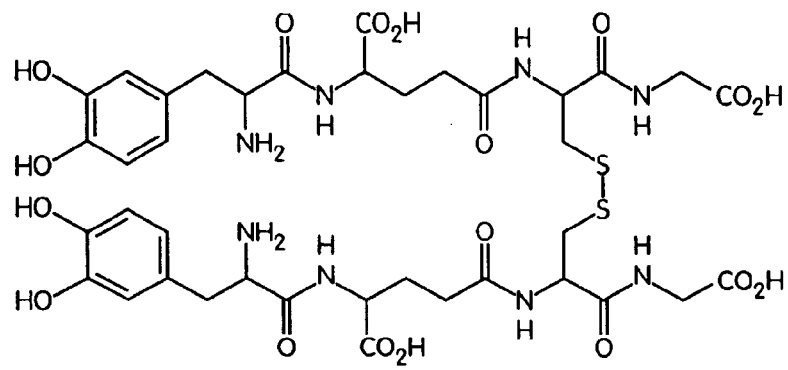
FIG. 16(g) shows the structure of bis-[3,4-dihydroxyphenylalaninyl].glutathione disulfide.

In one embodiment, the oxidized glutathione-based compound has an acylated primary glutamic acid amino group. This variant is most suitable for acylation by N-protected activated aminoacid derivatives, where after the stage of temporary protection of the cysteine mercapto-groups followed by condensation (activated ester method), and removal of the N- and S-protective groups and oxidation by the hydrogen peroxide with addition of cis-diamminedichloroplatinum results in the GSSG.Pt composite modified by amino-acids at the glutamic acid aminogroups. In this embodiment the oxidized glutathione-based compound can be selected from the group consisting of bis-[methionyl].glutathione disulfide (FIG. 16a), bis-[aspartyl].glutathione disulfide (FIG. 16b), bis-[histidyl].glutathione disulfide (FIG. 16c), bis-[3-iodine-tyrosyl].glutathione disulfide (FIG. 16d), [γ-aminobutanoyl].glutathione disulfide (FIG. 16e), bis-[γ-hydroxybutanoyl].glutathione disulfide (FIG. 16f), bis-[DL-6,8-thioetic acid].glutathione disulfide (FIG. 15b), and bis-[3,4-dihydroxyphenylalaninyl].glutathione disulfide (FIG. 16g).

Figure 7:
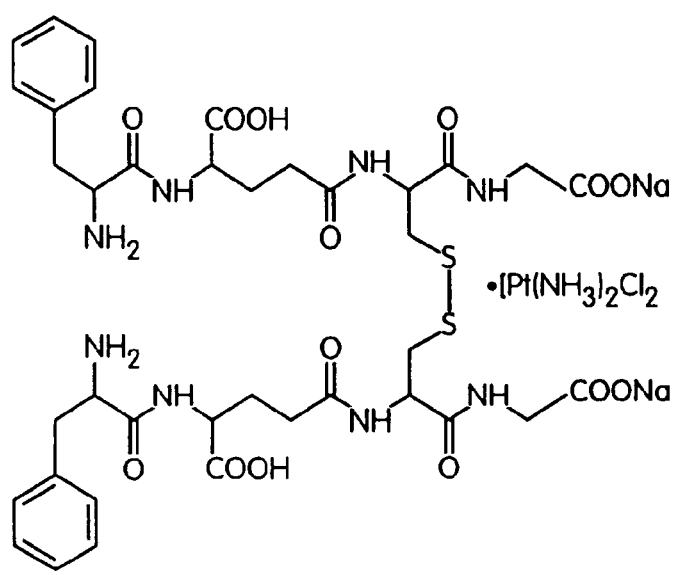
FIG. 7 shows the structure of bis-phenylalanyl-GSSG.Pt.
Figure 8:
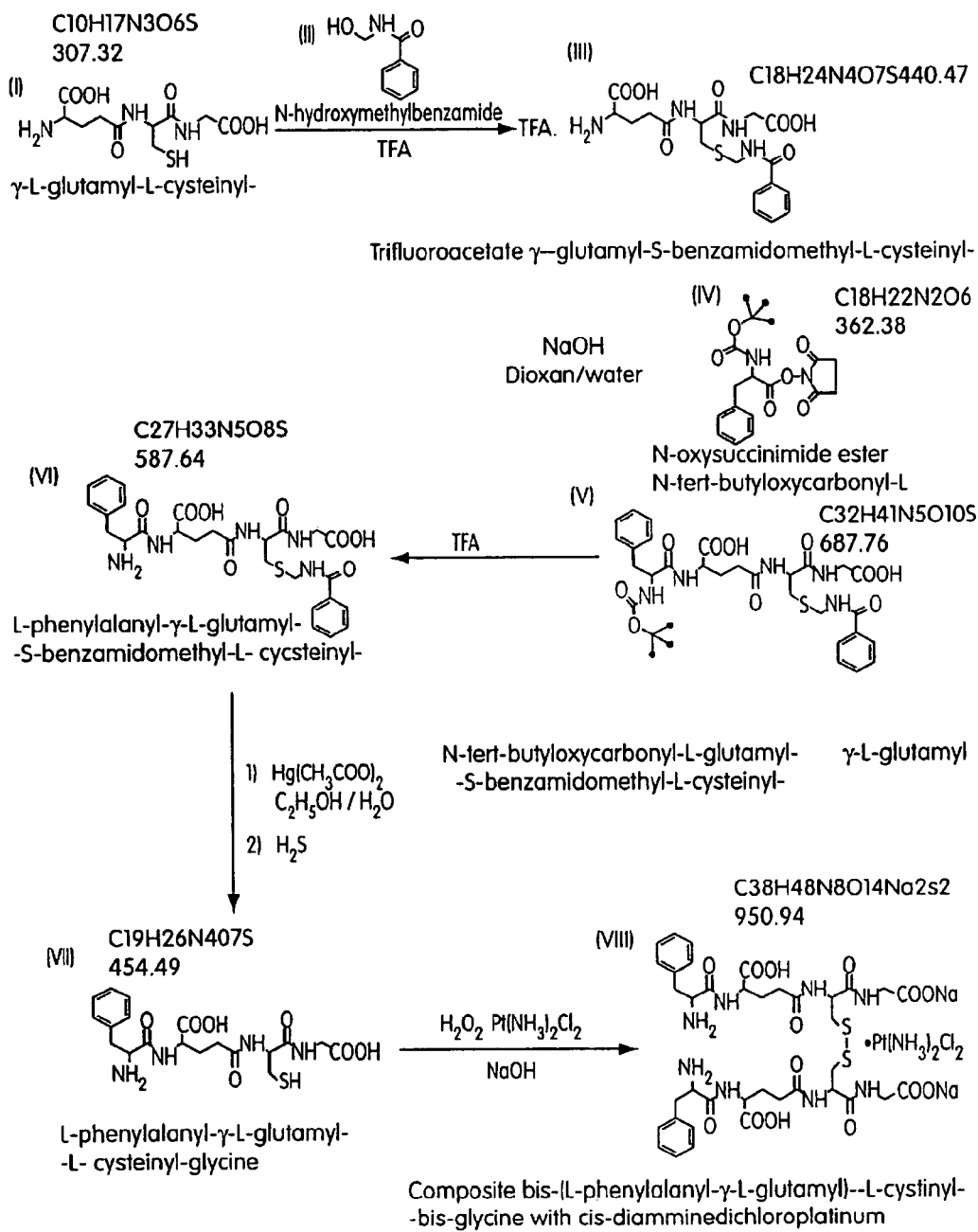
FIG. 8 shows the synthesis scheme for bis-(L-phenylalanyl-γ-L-glutamyl)-L-cysteinyl-bis-glycine with cis-diamminedichloroplatinum.
Figure 22:
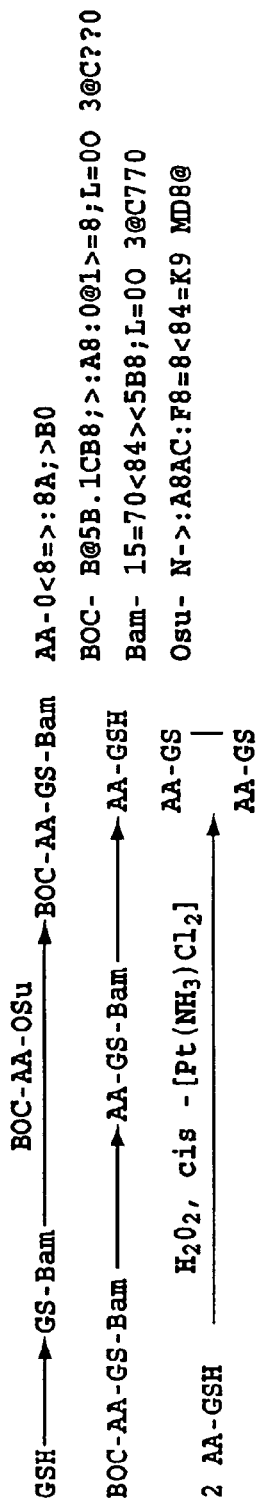
FIG. 22 shows a scheme for modifying a GSSG.Pt composite having phenylalanyl groups.

When the composite includes phenylalanyl groups, the compound is bis-phenylalanyl-GSSG.Pt (see FIG. 7). According to this basic scheme (as shown in FIG. 22), all other GSSG.Pt modifications based on the aminogroups acylation by the derivatives of the protected aminoacids, oxy-acids, carbonic acids and derivatives thereof are synthesized. Slight changes of the methods are possible due to a specific nature of modifying molecule. Protecting groups for the initial GSH compound include Bam (N-hydroxymethylbenzamide). The amino acid (AA) can be protected with groups such as BOC (butyl carbamate) or O-Su (N-oxysuccinimide ester; see FIG. 8 for specific details).

When the composite is bis-methionyl-GSSG.Pt, i.e., (Met)$_2$GSSG.Pt, incorporation of a methionine group may involve BOC-protective group deblocking after the condensation stage.

When the composite is bis-aspartyl-GSSG.Pt, an aspartic acid group can be introduced according to the general aforementioned scheme. A temporary protective group for the β-carboxyl group is preferably removed, if possible, with the BOC-protective group simultaneously if needed. A β-tert-butyl ester of N-BOC-aspartic acid, i.e., BOC-Asp (OBu$^t$)-OSu, can be applied at the condensation stage. The protective groups can be removed by trifluoroacetic acid (TFA).

When the composite is bis-histidyl-GSSG.Pt, a histidine imidazole ring can be protected via a di-tert-butyl-oxycarbonyl histidine derivative, i.e., BOC-His(BOC)-OSu, which can be used at the condensation stage. As in previous cases, the protective groups can be removed by trifluoroacetic acid.

When the composite is bis-3-iodine-tyrosyl-GSSG.Pt, a possible protecting group is an acid-labile protective group such as tert-butyl ester. The tyrosine derivative used at the concentration stage can be BOC-Tyr(OBu$^t$)-OSu.

When the composite is GABA-GSSG.Pt, (γ-aminobutanoyl-GSSG.Pt), an acid-labile protective tert-butyloxycarbonyl (BOC) group can be used at the condensation stage.

When the composite is GOBA-GSSG.Pt, (γ-hydroxybutanoyl-GSSG.Pt), an acid-labile group tert-butyl ester (which can be removed by a trifluoroacetic acid solution) can be used to protect a GOBA hydroxyl group. A derivative, used at the condensation stage, can be GABA(OBu$^t$)-OSu.

When the composite is bis-lipoyl-GSSG.Pt, it is believed that side functional groups of lipoic acid do not require special protection. At the condensation stage it is possible to apply an activated (hydroxysuccinimide) ester of lipoic acid. There may be no need for a TFA treatment.

When the composite is bis-3,4-dihydrooxyphenylalanyl-GSSG.Pt (bis-DOPA-GSSG.Pt), to introduce DOPA molecule, it may be necessary to previously protect two hydroxyl groups of 3,4-dihydroxyphenylalanine by tert-butyl esters and to protect the aminogroup by a BOC-protective group. For condensation with a composite precursor, an activated ester can be obtained (hydroxysuccinimide or pentafluorophenyl one) that is used in excessive mole amount. Removal of the protecting groups can occur simultaneously with a trifluoroacetic acid solution.

Figure 19A:
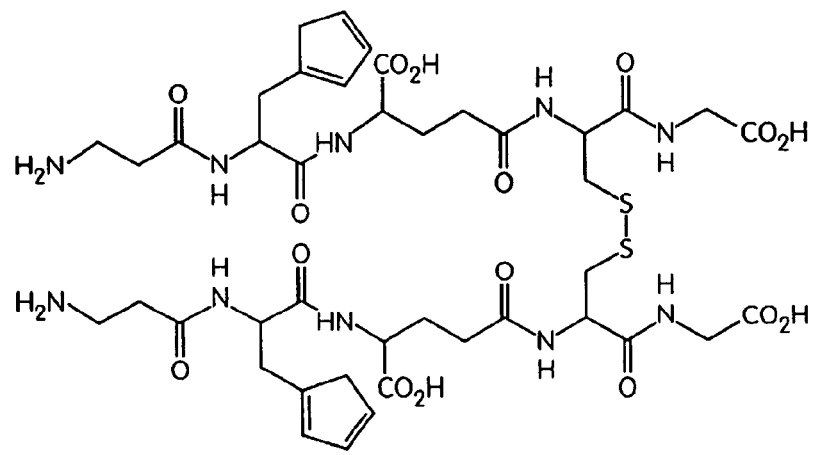
FIG. 19(a) shows the structure of bis-[carnosyl]-GSSG.

When the composite is bis-[carnosyl]-GSSG.Pt (bis-β-alanyl-L-histidyl-GSSG.Pt), carnosine can be protected as a di-BOC derivative of the β-alanine aminogroup and histidine imidazole group before condensation. Then condensation and following deblocking can be performed as previously described. A structure of bis-[carnosyl]-GSSG can be found in FIG. 19a.

Figure 17A:
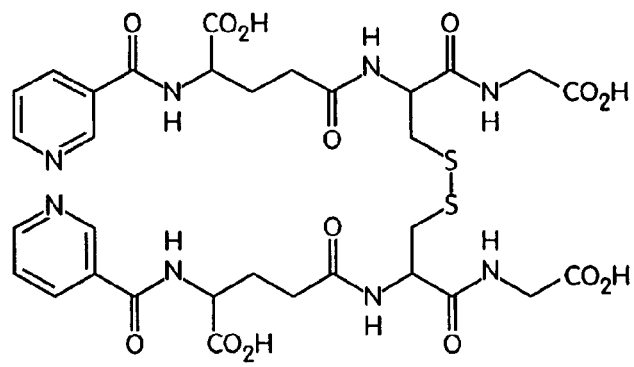
FIG. 17(a) shows the structure of bis-nicotinoyl-glutathione disulfide (bis-[pyridine-3-carbonyl].glutathione disulfide)
Figure 17B:
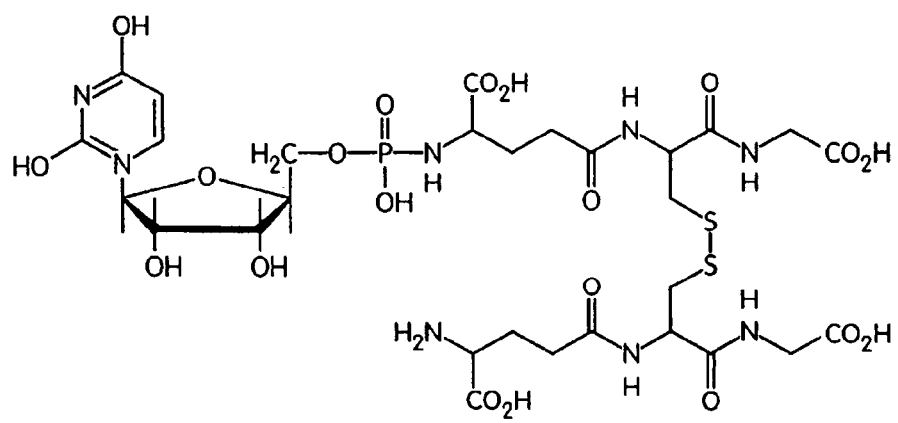
FIG. 17(b) shows the structure of uridine-5'-monophosphatoyl.glutathione disulfide.
Figure 17C:
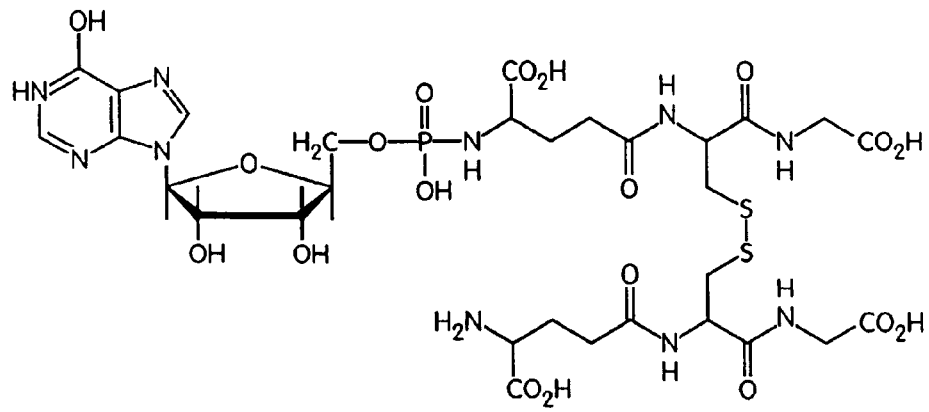
FIG. 17(c) shows the structure of inosine-5'-monophosphatoyl.glutathione disulfide.
Figure 17D:
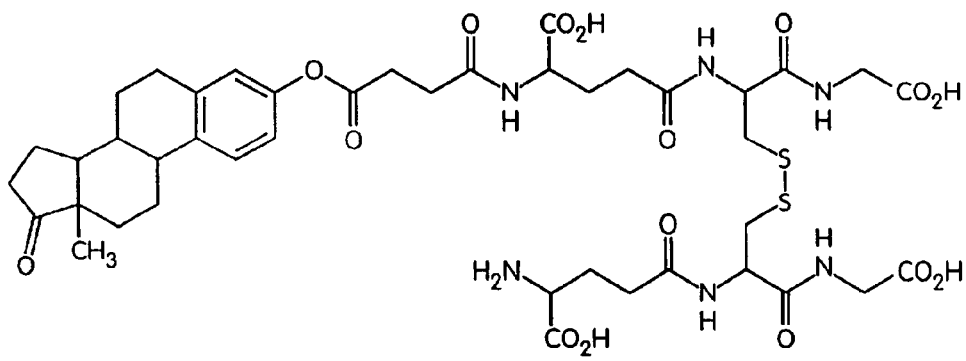
FIG. 17(d) shows the structure of folliculylsuccinyl.glutathione disulfide.
Figure 17E:
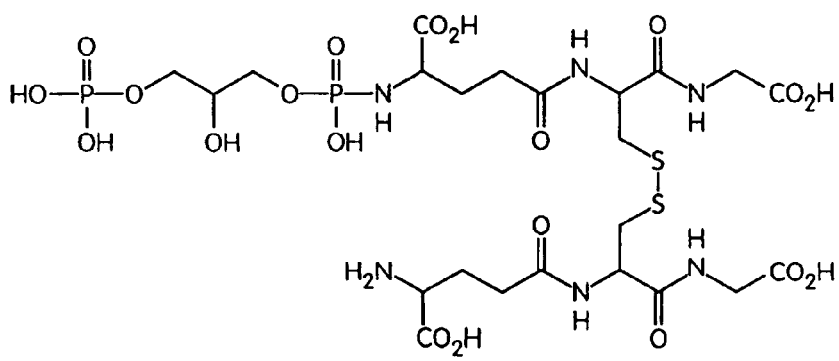
FIG. 17(e) shows the structure of glycerol-1,3-diphosphatyl.glutathione disulfide.

In another embodiment, the oxidized glutathione-based compound has an amide or phosphoramide bond to a unit selected from the group consisting of heterocyclic carbonic acids and nucleotides. In this embodiment, examples of the oxidized glutathione-based compound include bis-nicotinoyl-glutathione disulfide (bis-[pyridine-3-carbonyl].glutathione disulfide) (FIG. 17a), uridine-5'-monophosphatoyl.glutathione disulfide (FIG. 17b), inosine-5'-monophosphatoyl.glutathione disulfide (FIG. 17c), folliculylsuccinyl.glutathione disulfide (FIG. 17d) and glycerol-1,3-diphosphatyl.glutathione disulfide (FIG. 17e).

When the composite is bis-nicotinoyl-GSSG.Pt (bis-pyridine-3-carbonyl-GSSG.Pt), a nicotinic acid containing no side functional groups can be introduced into condensation with a composite precursor without obtaining protected derivatives as corresponding activated esters such as hydroxysuccinimide or pentafluorophenyl. TFA treatment for the removal of protecting groups may not be required.

When the composite is uridine-5'-monophosphatoyl-GSSG.Pt (UMP-5'-GSSG.Pt), uridine-5'-monophosphate in presence of N,N-dicyclohexyl-carbodiimide can form phosphoamide links in reactions with amides (Chambers R. W., J. Am. Chem. Soc., 80, 3752, 1958). The composite precursor can have protected carboxyl groups, such as tetratrimethylsilyl derivatives to be used as an aminocomponent. Deblocking can proceed in mild water-alcohol systems.

When the composite is ionosine-5'-monophosphatoyl-GSSG.Pt, IMP-5'-GSSG.Pt, the synthetic scheme would most likely be similar to that of the previous derivative (UMP-5'-GSSG).

When the composite is folliculylsuccinyl-GSSG.Pt, a link between GSSG.Pt and estrone can be made by amide and ester bonds through a succinyl residue. Estrone can be transformed into an activated derivative by reaction with succinanhydride with following condensation by N,N-dicyclohexylcarbodiimide with a protected or blocked composite precursor and with tetra-trimethylsilyl derivatives as well. Deblocking can be performed in a water-alcohol system.

When the composite is glycerol-1,3-diphosphatyl-GSSG.Pt, the modification can proceed by a carbodiimide method using a composite precursor protected, as a tetra-trimethylsilyl derivative as an amino component, the synthesis is similar to that in the synthesis of phosphoamide derivatives (See Examples 13 and 14).

Figure 18A:
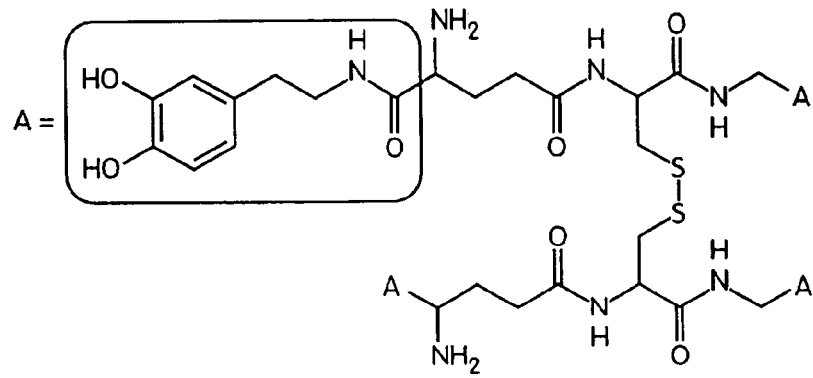
FIG. 18(a) shows the structure of tetra-dopamine.glutathione disulfide.
Figure 18B:
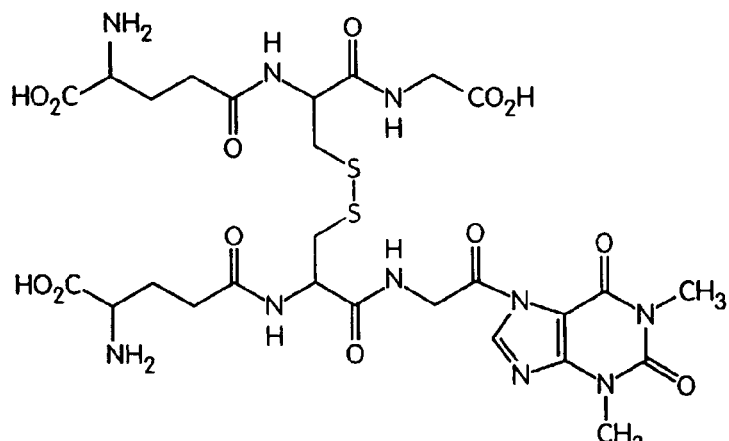
FIG. 18(b) shows the structure of theophylline.glutathione disulfide.

In another embodiment, the oxidized glutathione-based compound can be selected from the group consisting of tetra-dopamine.glutathione disulfide (FIG. 18a) and theophylline.glutathione disulfide (FIG. 18b). The formation of amide links can occur between composite carboxyl groups and amides. The reactivity of all four carboxyl groups is very similar and, therefore, a mixture of products can result.

When the composite is tetra-dopamine-GSSG.Pt, a 3,4-di-tert-butyl ester of dopamine can be used as an aminocomponent and di-tert-butyloxycarbonyl derivatives the composite can be used as a carboxyl component. Condensation can proceed by a N,N-dicyclohexyl-carbodiimide, and removal of the protective groups can be performed with a trifluoroacetic acid solution.

When the composite is GSSG.Pt-theophylline, theophylline can be used as an aminocomponent, a composite precursor can be used for a carboxyl component as a di-tert-butyloxicarbonyl derivative. Condensation can be performed with an "F" complex. The removal of protective group can be performed with a trifluoroacetic acid solution.

Figure 20A:
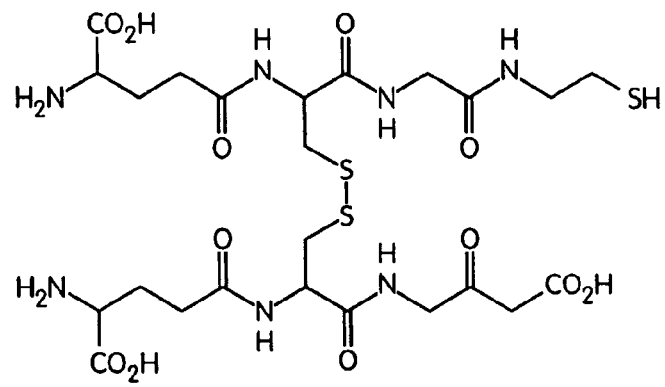
FIG. 20(a) shows the structure of a non-symmetric mixed disulfide compound.
Figure 20B:
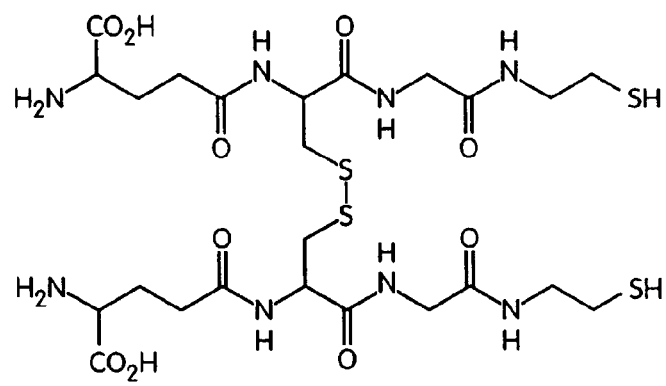
FIG. 20(b) shows the structure of a symmetric mixed disulfide compound.
Figure 20C:
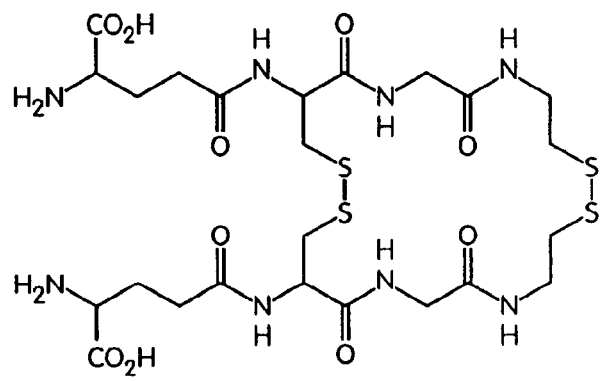
FIG. 20(c) shows the structure of a symmetric and doubly bridged mixed disulfide compound.

In another embodiment, the oxidized glutathione-based compound can include mixed disulfides. Possible combined structures can involve mixed disulfide formation (symmetric and non-symmetric). (See FIGS. 20a-20c) One structure (FIG. 20b) can be formed via mutual oxidation of mercaptogroups starting materials. There may be no need for additional protective groups and condensation methods.

Another compound (FIG. 20a) can be obtained by formation of an amide bond between the cyteamine aminogroup and one of the composite precursor carboxyl groups. It may be necessary to introduce N-protective groups and to activate the composite precursor carboxyl groups. Due to the presence of four carboxyl groups it may be necessary to manipulate the stoichiometry and/or perform chromatographic separation of the resulting products.

The synthesis conditions are different from the structure 20b by presence of the additional aminocomponent equivalent. At the chromatographic purification the structure 20b is used a witness.

It is obtained from the structure 20c through formation of an additional disulfide bond at the mercapto-group reaction. During the chromatographic separation of products, it may be necessary to have the structure 20c as a witness.

Figure 21A:
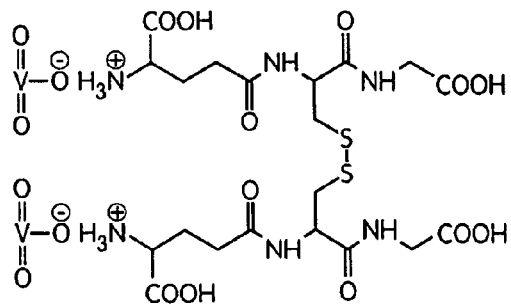
FIG. 21(a) shows the structure of divanadate salts.
Figure 21B:
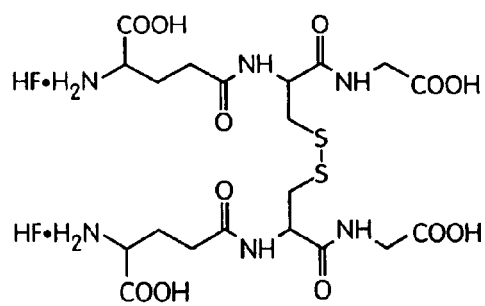
FIG. 21(b) shows the structure of dihydrofluoride salts.
Figure 21C:
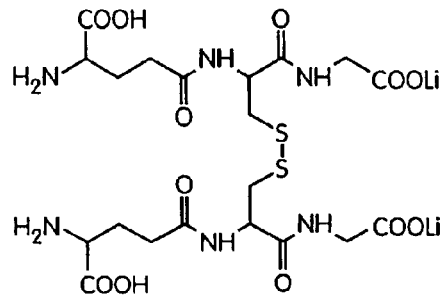
FIG. 21(c) shows the structure of dilithium salts.
Figure 21D:
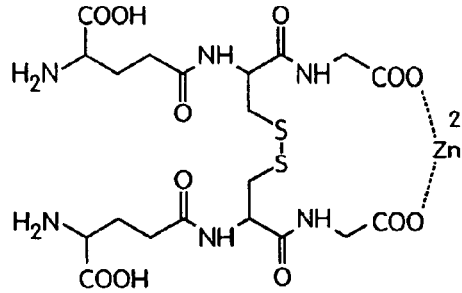
FIG. 21(d) shows the structure of dizinc salts.

In another embodiment, the oxidized glutathione-based compound can be a salt selected from the group consisting of alkali metal salts, alkaline earth metal salts, and transition metal salts. Examples of such salts include divanadate salts (FIG. 21a), dihydrofluoride salts (FIG. 21b), dilithium salts (FIG. 21c), didopammonium salts, and dizinc salts (FIG. 21d).

The salts can be obtained through addition of the corresponding amount of the salt-forming components, a base or an acid. Examples of salts with aminogroups includes a divanadate of GSSG.Pt($(HVO_3)_2$-GSSG.Pt) or a dihydrofluoride of GSSG.Pt ($(HF)_2$.GSSG.Pt). Examples of salts with carboxyl groups include a dilithium salt GSSG.Pt (see Example 2), a GSSG.Pt didopammonium salt or a GSSG.Pt zinc salt.

In another aspect of the invention, a drug comprising the composite is obtained according to the previously described method, such as the hexapeptide bis-(γ-L-glutamyl)-L-cysteinyl-bis-glycine disodium salt and cis-diamminedichloroplatin (cis-platin). Thus, the present invention provides a new class of medicinal substances "thiopoietins" that can be introduced into biological media, resulting in a new level of metabolism and cellular genetic activity.

An advantageous feature of the composite of the present invention is the biological activity, in particular:

Stimulation/modulation of the endogenous production for a significantly large range of the cytokine, growth and hemopoietic factors in conditions of radiation and chemical immunosuppression (IL-1α and β, IL-2, IL-3, IL-4, IL-6, IL-8, IL-10 and IL-12, TNF-α, IFN-α and IFN-γ, erythropoietin, colony-stimulating factors) (See Examples 5-7);

Reproduction of some cytokine effects (IL-2, IL-12, IFN-α and IFN-γ) due to the mechanism induction for the redox-sensitive expression of the immunologically significant genes and the key protein "critical" cysteine modification for the cellular signal-transducing systems (See Example 8);

Restoration of the depressed bone-marrow haemopoiesis including erythrocyte, leukocyte and platelet counts as well as levels of $CD3^+$, $CD4^+$, $CD8^+$, $CD16/56^+$, $CD19/20^+$, $CD25^+$, $CD34^+$, $CD95^+$ (See Examples 9-13) at patients receiving radiation and high-dose combined chemotherapy;

In conditions of an active antibacterial, antiviral and antitumor chemotherapy, hepatotropic effects as well as diminution of the cardio-, hephro- and neurotoxicity signs;

The differentiated impact with regard to normal cells (including the ones being under functional stress) and transformed ones, namely, the metabolism, proliferation and differentiation stimulation at the normal cells/tissues and, simultaneously, the apoptosis mechanism induction only in the tumor- and/or virus-transformed cells. The data appears to support the induction of p53-dependent and p53-independent, Bcl-2-intensive apoptosis pathway/types occurring (See Examples 14-16).

The method for the production of the composite makes possible synthesis of different composites as a basis for design of drugs possessing a range of new features, namely:

Increased biochemical drug stability, i.e., "non-assailability" by the GSSG metabolism enzymes (i.e., far less accessible for these enzyme action), first of all, by NADP.H$^+$-dependent glutathione reductase that basically increases the drug half-life time in the biological media exactly in the disulfide form;

New biophysical component with high level of the donor-acceptor potential;

Presence of new reactive sites within the said molecule and, therefore, entirely new capacity for chemical modification.

The composite properties allow it to function as a unique cellular "gyroscope" that in conditions of the extreme external environmental factors (physical, chemical and biological ones) provides restoration of a balance:

Within the cytokine profile, i.e., the cytokines regulating proliferation mainly; and the cytokines regulating mainly differentiation of the immunocompetent cells;

Ratio of the cellular redox potential including donor/acceptor balance of the electron dynamics due to restoration of the thiol-disulfide metabolism; NAD/NAD.H and NADP/NADP.H ratios;

cAMP/cGMP ratio, changes of the extra- and intracellular ionized calcium;

Relationship of the transcriptional differentiation factors (NFκB) and proliferation factors (AP-1); relationship of the functional activity manifestations of p53, p21 and ras-proteins, therefore, balance of cellular proliferation, differentiation and apoptosis taking into account basically different exhibitions of these effects in the normal and transformed cells.

In the applied invention, including examples of the preferred embodiments, the following terminology accepted is used.

"Subject in need thereof" as used in this application herein comprises a mammal, e.g., man, domestic animals and livestock including cats, dogs, cattle and horses, having one or more manifestations of a disease in which stimulation of endogenous cytokine or hemopoietic factor (or both) production as well as an apoptosis mechanism regulation would be considered beneficial by those skilled in the art with an up-to-date biomedical knowledge.

"Medicinal drug" as used in this application includes any drug form containing the composite of the present invention, e.g., GSSG.Pt and derivatives, which has a therapeutic effect on neoplastic, infectious, hematologic, immunologic, neurodegenerative or other diseases.

"Therapeutic effect" indicates any effect in man and other mammals which is beneficial, including curative, preventative, allowing maintenance at a beneficial level, or being in any way advantageous in regard to a body of man and other mammals.

"Pharmaceutically acceptable salt" as used in this application comprises any composite derivative in the form of a salt that is acceptable for use in the body without unwanted detrimental effect on the body, and including, for example, sodium, lithium, zinc or vanadium cations, or sodium, lithium, zinc or vanadium salt respectively.

"Pharmaceutically acceptable composition" as used in this application involves the composite, or derivative thereof, as a pharmaceutically acceptable substance and may include, in addition, a group of active metabolites or other chemical compounds. For example, the composite or derivative can include or can be covalently bound to phenylalanine or to cystamine.

"Metabolism" as used in this application involves the totality of all biochemical reactions taking place within the living organism responsible for vital function maintenance in the said organism (Robert C. Bohinski "Modern Concepts in Biochemistry", 4th edition, 1987).

"Proliferation" as used in this application involves reproduction or multiplication of similar forms (cells) due to constituting (cellular) elements (Stedman's Medical Dictionary, 26th edition, Moscow, 1995, p. 519; Miller-Keane "Encyclopedia & Dictionary of Medicine, Nursing, & Allied Health, 5th edition, W.B. Saunders Company, 1992, p. 1221).

"Differentiation" as used in this application involves cell changes including acquisition or possession of features distinguishing from an original with the cell conversion from relatively simple functions to more complex, specialized functions as is in morphological and/or functional heterogeneity incident to the given cellular type through the tissue-specific gene expression (A. Horst "Molecular Basis for Disease Pathogenesis", Moscow, 1982, p. 125; Brian W J Mahy "A Dictionary of Virology", 2-e Academic Press, 1997, c. 87; Stedman's Medical Dictionary, 26th edition, Moscow, 1995, p. 179; and Miller-Keane "Encyclopedia & Dictionary of Medicine, Nursing, & Allied Health", 5th edition, W.B Saunders Company, 1992, p. 424).

"Apoptosis" as used in this application involves morphologically distinguishable forms of genetically programmed, physiological cell death initiated by extra- or intracellular signals when there are activated enzymes (e.g., the caspases group) causing destruction (e.g., fragmentation) of nuclear DNA through intranucleosomic cuts and morphologically manifested by (1) cell shrinkage; (2) condensation, margination, and fragmentation of chromatin; and (3) retention of cytoplasmic organelle structure, but loss of positional interrelationships; further apoptotic cells or apoptotic bodies formed out of them are engulfed (incur phagocytosis) (Harrison's Principles of Internal Medicine, 14th edition, p. 511, 1998; Apoptosis: a role in neoplasia, C. D. Gregory, 1996; and The Molecular Biology of Apoptosis, D. L. Vaux, A. Strasser; Proc. Natl. Acad. Sci. USA 93 (1996)).

"Cytokines" as used in this application comprises peptide-origin regulatory compounds produced by the different cell types playing a key role in the immune response development, hemopoiesis and different disease pathogenesis, performing their effect through gene activation, participating in regulation for all immune system elements (proliferation and differentiation of immune competent cell precursors; antigen representation, antigen-sensitized lymphocyte proliferation, B-lymphocyte differentiation into antibody-producing cells, T-lymphocyte differentiation into functionally different T-lymphocytes; functions of macrophages, neutrophils, eosinophils, mast cells and basophils), as well as controlling growth, differentiation, apoptotic processes and functional activity for different tissue cells (including fibroblasts, chondrocytes, keratinocytes, endotheliocytes, nerve tissue cells and cardiomyocytes) (Harrison's Principles of Internal Medicine, 14th edition, p. 511, 1998; Apoptosis: a role in neoplasia, C. D. Gregory, 1996).

As used herein, the terms "neoplastic and infectious disease", "hemopoiesis and immunity depression of various origin", and "other diseases" mean any neoplastic or infectious disease, any conditions caused or accompanied by the erythroid or myeloid suppression, or a reduction in quantitative or functional immunity parameters, as well as any other disease or pathological condition, in which stimulation/modulation of the aforesaid cytokine and/or hemopoietic factor endogenous production as well as apoptosis mechanism induction would be considered advantageous by those skilled in the art. Thus, modulating the cytokine and hemopoietic factor endogenous production for a person in need thereof by using the composite with the stabilized disulfide bond (e.g., GSSG.cis-platin), which being introduced parenterally also has a new feature of influencing the cytokine profile allowing regulation of the normal cell metabolism, proliferation and differentiation processes.

One embodiment of the present invention provides a method for stimulating endogenous production of cytokines and hemopoietic factors. The method includes the step of introducing to a mammalian body in need of such stimulation an effective amount of a composite comprising the oxidized glutathione-based compound and a metal material for a period of time to stimulate the endogenous production to obtain a therapeutic effect. As described previously, the ratio of the oxidized glutathione-based compound to the metal material is between about 3000:1 to about 1:1 where the metal material comprises a metal selected from the group consisting of platinum and palladium.

Therapeutic effect includes alleviation, prevention or curing of an unwanted body condition and can comprise a process selected from the group consisting of regulating proliferation in normal cells, regulating differentiation in normal cells, and inducing apoptosis of transformed cells where the transformed cells can include diseased cells. The therapeutic effect includes preventative, alleviation and curing effects in various diseases.

"Disease" refers to any unwanted condition of the body including, but not limited to, selected oncological diseases, infectious diseases, immunological diseases, ischemic diseases, neurodegenerative diseases, metabolic diseases, endocrinal diseases, and any other unwanted medical condition.

The composite can be administered by various methods: orally or as a solution form selected from the group consisting of inhalation solutions, local instillations, eye drops, intranasal introductions, an ointment for epicutaneous applications, intravenous solutions, injection solutions, and suppositories. Preferably, the glutathione is introduced parenterally or topically. The method is carried out by introducing the composite, derivatives or salts thereof to enhance the regulatory influence on stimulating of the cytokine and hemopoietic factor endogenous production; or to induce apoptosis mechanisms in transformed tissues, which provides regulation of metabolism, proliferation and differentiation in tissues and achieving a corresponding therapeutic effect.

In one embodiment, the composite is administered in a dosage of between about 0.1 mg/kg to about 1.0 mg/kg by body weight. In another embodiment, the composite is administered in a dosage of between about 1 mg/m$^2$ to about 100 mg/m$^2$ by body surface. In another embodiment, the drugs can be applied one or more times a day, by one or more day pulses or continuous administration until a desired therapeutic effect is achieved.

In a preferred embodiment, the GSSG.Pt material pharmaceutically acceptable derivatives are introduced to the body at a dose from 0.01 to 1.0 mg of GSSG.Pt material per kg of body weight for the GSSG.Pt material or salt thereof; or at a dose from 1 to 100 mg per 1 m$^2$ of body surface and in case when applied epicutaneously/through instillations at a dose from 1 to 100 mg per 1 m$^2$ of body surface as well, at least, once during each 24 hour period. Also the drug can be continuously injected or otherwise introduced to the body to have a 24 hour total dosage from 0.01 to 1.0 mg per kg of body weight for GSSG.Pt base and salts thereof, and from 1 to 100 mg per 1 m$^2$ of body surface during each 24 hour period. Preferably, administration and introduction to the body should be carried out until a desired stimulating effect on the cytokine and hemopoietic factor production or the apoptosis induction and, thus, the cellular metabolism, proliferation and differentiation regulation and corresponding therapeutic effect is obtained.

Where the composite is administered as a solution, preferably the solution has a concentration of between about 1% to about 10% of the composite. Preferably, the pharmaceutically acceptable derivatives of the GSSG.Pt material for parenteral use is in a pharmaceutically acceptable solvent as, for example, an aqueous solution including water, glucose solution, isotonic solutions of sodium chloride, buffered salt solutions. Other physiological solvents or carriers can be used. Where the composite is administered as an injectable form, preferably the injectable form comprises the composite in a solution in a concentration of between about 0.01% to about 3.0%.

For topical application including application for different body cavities, organic solvents or carriers may be used in the form of ointments, pastes, creams or suppositories.

The examples of the invention embodiments given below demonstrate feasibility of the invention practical use and confirm its effectiveness, and also expediency of using these medicinal drugs as an injectable solution containing 0.01% to 3% of GSSG.Pt base or the salts thereof with the dosage range from 0.1 to 1.0 mg/kg by body weight or from 1 to 100 mg/m$^2$ of body surface. In cases when the GSSG.Pt drugs are administered like inhalation solutions, local instillations, eye drops, intranasal introduction, or an ointment for epicutaneous applications, or suppositories, the recommended concentration range is from 1% to 10% of GSSG.Pt base or the salts thereof.

The active principle, the composite of the hexapeptide with the stabilized disulfide bond—GSSG.Pt—capable of stimulating/beneficial modulating the endogenous cytokine and hemopoietic factor production as well as inducing of transformed cells apoptosis, may be obtained by original, developed by the authors the peptide synthesis technique provided herein. Thereby, the obtained hexapeptide composite (GSSG.Pt) with purpose for subsequent usage in animals and humans is applied as a pharmaceutically acceptable GSSG.Pt derivative in an injectable drug form prepared by dissolving of the bulk substance in sterile water for injections or in any pharmaceutically acceptable solvent with the resultant concentration 0.01-3.0%. For an in vitro use in experimental settings, GSSG.Pt or the derivatives thereof may be dissolved in solvents acceptable for performance of corresponding experiments such as culture media, isotonic saline solutions, glucose solutions and the like.

Injectable medicinal forms of the GSSG.Pt, salts and compositions thereof have been tested in animal studies and as well in wide clinical studies and pilot trials on sick persons. The drug form for human and animal use should be prepared under sterile and pyrogen-free conditions while exerting every effort to prevent chemical or bacterial contamination of the medicinal form.

Using the maximum achievable concentration of the GSSG.Pt material sodium salt solution (10.0%, 100 mg/ml) in water for injections (or in normal saline), and using the maximum tolerable volumes administered to mice intraperitoneally (IP, 2.0 ml), intravenously (IV, 0.5 ml), and intramuscularly (IM, 0.05 ml), there have been reached the GSSG.Pt dosage levels of 5000 mg/kg (IP), 1350 mg/kg (IV), and 135 mg/kg (IM), i.e. 1000, 270, and 27 times, respectively, have been obtained in mice, exceeding the maximum recommended human dose. In none of the cases either animal deaths or any toxic signs were observed, proving, in fact, the GSSG.Pt material in injectable drug form are essentially non-toxic.

Figure 6:
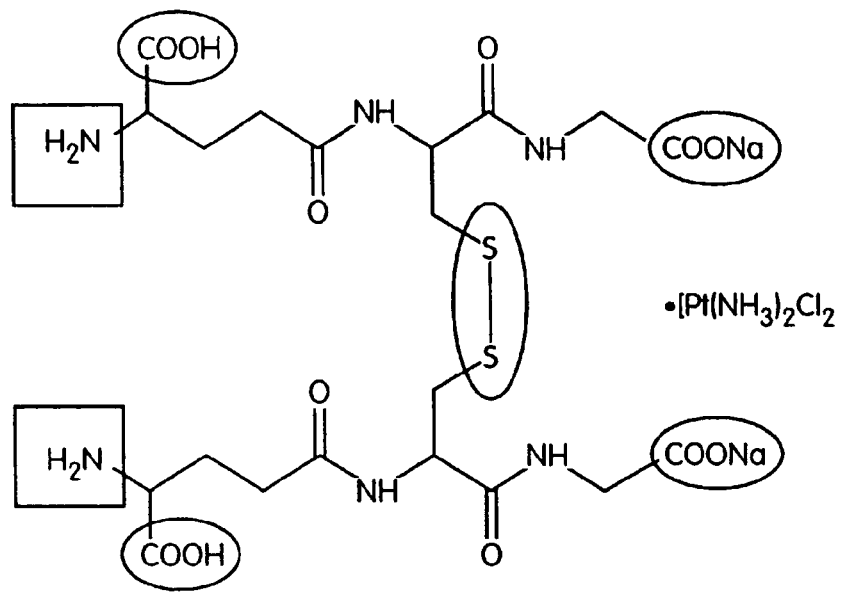
FIG. 6 shows the main sites (encircled) for the GSSG.Pt molecule chemical modification.

Through chemical modifications of the basic GSSG.Pt molecule, it is possible to create new drugs where, in molecules along with the basic structure that have already demonstrated high medical-biological activity based on the oxidized glutathione composite with cis-diamminedichloroplatinum, there are fragments of other covalently-bound biochemically active molecules. Usage of the covalently bound combinations allows enhancing of a range of important drug characteristics such as stability and standardized properties of composition. Foundation for the chemical modifications is the GSSG.Pt hexapeptide core with two primary glutamic acid aminogroups, cysteine disulfide bond and carboxyl groups of glycine and $\alpha$-carboxyl groups of glutamic acid (FIG. 6).

Purposely elected covalently-bound fragments of biochemically significant molecules can considerably improve medical-biological features of the basic GSSG.Pt material composite making them more selective for each particular therapeutic purpose, resulting in a sharp increase in a desirable treatment course. It might be conditioned with an additive effect of fragments in the biochemical activity mechanisms, sharp improvement of the basic molecule transport to a target-cell or a target-molecule, larger affinity for a receptor, necessary redistribution of oxidative-reductive (redox) potential and a range of other factors as well as combination thereof.

In one embodiment, the drug including the composite of the present invention can be useful for the treatment of a variety of oncological diseases. Included in these oncological diseases are solid tumors including those selected from the group consisting of lung cancer, melanoma, cerebral tumors, colorectal cancer, breast cancer, prostate cancer and ovarian cancer. The drug of the present invention can be effective for hematologic tumors (non-solid tumors) including acute lymphoblastic leukosis and acute myeloblastic leukosis.

For lung cancer treatment, application of GSSG.Pt is preferred for the first or fourth stages of the disease as a monoregime. The monthly course includes dosages from 10 to 100 mg/m$^2$ of the body surface of intravenous (IV) and intramuscular (IM) drug introduction. In the second or third stage, GSSG.Pt can be applied in combination with common chemotherapy by means of IV, subcutaneous and local (intrapleural) introduction of the drugs. The GSSG.Pt dosage is preferably from 30 to 50 mg/m$^2$ of the body surface.

For melanoma treatment, bis-[-iodine-tyrosyl]-GSSG.Pt can be particularly effective. The monthly course can comprise IV and IM drug introductions every day, with a dosage of about 30 to 100 mg/m$^2$ of the body surface. Maintenance therapy can occur over a period of up to six months-one year. It comprises subcutaneous (locally, close to the impaired zones) and IV drug introductions once a week, with a dosage of about 10-30 mg/m$^2$ of the body surface.

For treatment of cerebral tumors, bis-[dopamine]-GSSG.Pt is preferred and may be applied by means of IV injections and catheterization of the carotid artery. The dosage is preferably about 10 to 100 mg/m$^2$ of the body surface. The IV introduction can last three weeks, once every other day. For introduction through the carotid artery, application preferably occurs twice every day during six to seven days. The repeat course can be administered two weeks later, over a period of 21 days as well and comprise IV injections mainly.

For treatment of colorectal cancer, i.e., adenocarcinoma of stomach and pancreas, bis-[cystamine]-GSSG.Pt is preferred and can be applied by means of IV and subcutaneous injections with a dosage of about 10 to 30 mg/m$^2$ of the body surface. Two to three week administration can be used as a pre-surgery preparation and post-surgery patient management. In case of inoperable stomach cancer, applying the drug through a fibergastroscope is recommended, introducing the drug around the cancer infiltrate once every week with the single drug dose of 30-100 mg in this case. Preferably, the solution volume does not exceed 3 mL.

For breast cancer treatment, cystamine-GSSG.Pt is preferred by means of IV and subcutaneous injections with a dosage of about 10 to 100 mg/m$^2$ of the body surface as a pre-surgery preparation and post-surgery patient management. Maintenance therapy can take up to one year and can comprise application of cystamine-GSSG.Pt along with ordinary chemotherapy by courses lasting up to two weeks. There can be one-month intervals between courses.

For prostate cancer treatment, application of the zinc salt of GSSG.Pt is preferred through IV injections and through the drug introduction into lymphatic spaces with a dosage of about 10 to 100 mg/m$^2$ of the body surface. The approximate treatment course duration can occur over a period of three to seven weeks.

For ovarian cancer treatment, application of theophylline-GSSG.Pt is preferred as an anticancer medicine and as a remedy that restores the cancer susceptibility to cis-platin. There can be IV and endolumbal routes for the drug introduction with a dosage of about 10 to 100 mg/m$^2$ of the body surface over a period of three to seven weeks. It is possible to combine this treatment with antiestrogen therapy.

For treatment of acute lymphoblastic leukosis, lithium salt of GSSG.Pt is preferably applied intravenously as a month course with a dosage of about 10 to 50 mg/m$^2$ of the body surface along with ordinary chemotherapy.

For treatment of acute myeloblastic leukosis, the lithium salt of GSSG.Pt is preferably applied in combination with cystamine-GSSG.Pt through IV introduction with a dosage of about 10 to 100 mg/m$^2$ of the body surface. The duration of treatment can occur over a period of about three weeks. The maintenance treatment can be repeated after three-month periods during one year with a treatment course duration of about 14-17 days.

Infectious diseases that can be effectively treated with the drug of the present invention include tuberculosis, viral hepatitis B and C and mixed infections (HBV and HCV), herpes, meningitis (sepsis), peritonitis, acute pancreatis and supporative post-surgery sequalae.

The treatment of tuberculosis can involve a disseminated process with destructive pathologic changes (cavities +) and bacterial discharge (BK +). Preferably, bis-[histidyl]-GSSG.Pt is applied by means of IV and IM injections during one month with a dosage of about 3-10 mg/kg of the body weight. For the following two months, the dosage can be 1-5 mg/kg of the body weight. The drugs can be introduced intravenously twice a week or intramuscularly every other day.

For the treatment of viral hepatitis B and C and mixed-infections (HBV and HCV), GSSG.Pt and inosine-5-monophosphatyl-GSSG.Pt (IMP-5-GSSG.Pt) is preferably applied by means of IV and IM injections with daily dosage of 30 and 40-50 mg, respectively. In the case of hepatitis B (HBV), the treatment course duration can be up to one month. In the case of hepatitis C(HCV) and mixed infections, the treatment course duration is preferably not less than three months with 10-12 day intervals after each month of the treatment.

For the treatment of herpes, the course therapy preferably involves GSSG.Pt and IMP-5-GSSG.Pt in a manner similar to that for hepatitis C(HCV) patients.

For the treatment of meningitis, sepsis, tetra-dopamine-GSSG.Pt is preferably applied by means of IV and IM injections with a daily dosage of about 3-10 mg/kg of the body weight. In meningitis patients, applying intralumbal injections is recommended in dosage of 30-70 mg once every three to four days until the patient's clinical state, blood and liquor indices restore to normal.

For the treatment of peritonitis, GSSG.Pt and tetra-dopamine-GSSG.Pt is preferably applied by means of IV and IM injections with a daily dosage of about 30-70 mg over a period of 10-14 days until there is full restoration to norm of the patient's clinical state and objective indices (blood and urine analyses; "liver" biochemistry).

For the treatment of acute pancreatitis, GSSG.Pt and IMP-5-GSSG.Pt is preferably applied by means of IV and subcutaneous (along a left costal arch) injections with a daily dosage of about 3-10 mg/kg of the body weight, preferably every day during the first week and then three times a week during the following 14-17 days. This treatment can result in the restoration of the patient's clinical state to normal.

For the treatment of supportive post-surgery sequalae, preferably GSSG.Pt and IMP-5-GSSG.Pt is applied in a manner similar to that for peritonitis.

The drug of the present invention can be effective for various immunological diseases. Such diseases include immunosuppressive diseases such as AIDS and immuno-suppressions of infectious diseases of radiation or toxic origin. Autoimmune diseases include glomerulonephritis, rheumatoid arthritis, collagenosis, systemic lupus erythematosus, and diabetes types I and II. Other immunological diseases include atopic forms of allergic conditions which include allergic rhinitis, atopic dermatipis, bronchial asthma and urticaria.

For the treatment of AIDS, GSSG.Pt and uridine-[5-monophosphatyl]-GSSG.Pt (UMP-5-GSSG.Pt) are preferably applied by means of IV and IM injections alternated every other day with a daily dosage of about 1-3 mg/kg of the body weight during 30 days. The treatment course total duration can be up to six months with two to three week intervals after each month of the therapy application. This treatment can be combined with common antiviral therapy. In the case of such a combination, the antiviral remedies can be used as "impulse", i.e., short-term courses (7-10 days for each course). In case of the AIDS-associated encephalopathy, using GSSG.Pt and UMP-5-GSSG.Pt is recommended in single doses of about 30 to 70 mg, respectively, once every week, during one month.

For treatment of immunosuppressions of infectious diseases of radiation or toxic (chemical) origin, GSSG.Pt and UMP-5-GSSG.Pt is preferably applied by means of IV and IM injections with a dosage of about 1-3 mg/kg of the body weight, every day, during 10-12 days until hemopoiesis is corrected to normal and the immune system is restored.

For the treatment of glomerulonephritis, GSSG.Pt and lithium salt of GSSG.Pt is preferably applied by means of IV and IM injections with a daily dosage of about 10-30 mg, 1-2 times every day during first two weeks. Subsequent treatments preferably involve applying IM injections only with a dosage of about 30 mg, once every day during one month. The full course duration can be up to three months with two week intervals after each month.

For the treatment of rheumatoid arthritis, GSSG.Pt and lithium salt of GSSG.Pt is preferably applied by means of IV and subcutaneous injections close to impaired joints with a dosage of about 10 mg, two times every day during three weeks. Preferably, subsequent treatments involve applying subcutaneous injections only, one injection two to three times a week during three months.

For the treatment of collagenosis, the treatment course preferably involves GSSG.Pt and lithium salt of GSSG.Pt in a manner similar to that of rheumatoid arthritis. The treatment can also involve the addition of no greater than 500 mg of vitamin C per day.

For the treatment of systemic lupus erythematosus, the treatment course preferably involves GSSG.Pt and lithium salt of GSSG.Pt in a manner similar to that of collagenosis.

For the treatment of atopic forms of allergic conditions (allergic rhinitis, atopic dermatitis, bronchial asthma, urticaria), GSSG.Pt and dihydrofluoride-GSSG.Pt [$(HF)_2$.GSSG.Pt] is preferably applied by means of IM, subcutaneous injections and nasal drops with a dosage of about 0.1-1 mg/kg of the body weight, two times every day during three weeks. No less than two or three treatment courses is preferred, usually in spring and late fall.

For the treatment of diabetes-type I, vanadium salt of GSSG.Pt (divanadate-GSSG.Pt) is preferably applied by means of IV and IM injections with a dosage of about 1-2 mg/kg of the body weight, along with bis-[nicotinoyl]-GSSG.Pt with a dosage of about 1-3 mg/kg of the body weight. Preferably, three to four week treatment courses are performed every three months.

For the treatment of diabetes-type II, bis-[lipoyl]-GSSG.Pt is preferably applied by means of IV and IM injections with a dosage of about 3-7 mg/kg of the body weight, along with bis-[nicotinoyl]-GSSG.Pt, dosage—1-3 mg/kg of the body weight (mainly within the dropper composition based on a 0.5% solution of glutamic acid). The treatment courses can occur over a period of one month, two to three times a year.

The drug of the present invention can be effective for the treatment of ischemic diseases such as ischemic cerebral conditions including post-insult conditions (e.g., infantile cerebral paralysis) and ischemic heart diseases such as those manifested mainly as a syndrome of conduction impairment and arrythmias (tachyarrythmia, bradyarrythmia, and impairment of ventricular conduction due to blockage of the His bundle or branches) and diseases manifested mainly as a syndrome of functional myocardial failure (cardiomyopathies of different origin, metabolic myocardio dysfunctions, and post-infarction conditions).

For the treatment of ischemic cerebral conditions including post-insult ones (e.g., infantile cerebral paralysis), bis-[phenylalanyl]-GSSG.Pt is preferably applied by means of IV and IM injections with a dosage of about 1-7 mg/kg of the body weight, as treatment courses last three to four weeks and intervals after each course up to one month. The total treatment duration can take up to two years.

For the treatment of ischemic heart disease (IHD) manifested mainly as a syndrome of conduction impairment and arrhythmias (tachyrhythmia, bradyrhythmia, impairment of ventricular conduction due to block of the His's bundle or branches), bis-[carnosyl]-GSSG.Pt (bis-β-alanyl-L-histidyl-GSSG.Pt) is preferably applied by means of IV and IM injections with a dosage of about 2-5 mg/kg of the body weight as treatment courses lasting three to four weeks.

For the treatment of IHD manifested mainly as a syndrome of functional myocardial failure (cardiomyopathies of different origin; metabolic myocardial dysfunctions, post-infarction conditions), glycerol-[1,3-diphosphatyl]-GSSG.Pt is preferably applied by means of IV and IM injections with a dosage of about 3-7 mg/kg of the body weight, mainly within the dropper composition containing a 5% glucose solution. The treatment courses duration can occur over a period of two to three weeks, two to three times a year.

The drug of the present invention can be effective for the treatment of neurodegenerative diseases such as Alzheimer's disease, hereditiary (Huntington's) chorea, amyotrophic lateral sclerosis, neuro-AIDS and demyelinating diseases such as multiple sclerosis. Neurodegenerative disease can also include neurobehavioral diseases such as diseases caused by drug (narcotic) abstinence and behavioral diseases created with psychotropic and nootropic drugs, such as cerebral hypoxia (post-ischemic conditions), manic-depressive psychosis and schizephrenia.

For the treatment of neurodegenerative diseases, such as Alzheimer disease, hereditary (Huntington's) chorea, amyotrophic lateral sclerosis, neuro-AIDS, bis-[3,4-dihydroxyphenylalanyl]-GSSG.Pt is preferably applied by means of IV, subcutaneous (along cervical-thoracic spine) and IM injections with a dosage of about 1-5 mg/kg of the body weight, as treatment courses lasting up to one month during one year. Intervals between courses can be two or three weeks.

For the treatment of demyelinating diseases, such as multiple sclerosis, bis-[3,4-dihydroxyphenylalanyl]-GSSG.Pt is preferably applied by means of IV and subcutaneous (along the spine and endolumbal route) injections with a dosage of about 1-10 mg/kg of the body weight, as treatment courses lasting up to one month. The total treatment duration can last up to one to two years. The drug can be introduced through endolumbal route one to two times a month.

Psychotropic and nootropic drugs can be used for treatment of neurodegenerative diseases such as cerebral hypoxia (post-ischemic conditions), γ-hydroxy-[butanoyl]-GSSG.Pt can be applied by means of IV and IM injections with a dosage of about 1-4 mg/kg of the body weight as two to four week treatment courses. Introduction of the drug endolumbally is recommended once a week, with a dosage of about 1 mg/kg of the body weight.

For the treatment of manic-depressive psychosis, such as schizophrenia, γ-amino-[butanoyl]-GSSG.Pt is preferably applied by means of IV and IM injections with a dosage of about 3-5 mg/kg of the body weight as four to six week treatment courses two to three times a year.

The drugs of the present invention can be effective in diminishing the contents of pre-β- and β-lipoproteins in blood for the treatment of atherosclerosis and other metabolic diseases. Bis-[nicotinoyl]-GSSG.Pt (bis-pyridine-3-carbanoyl-GSSG.Pt) can be applied by means of IV and IM injections with a dosage of about 1-3 mg/kg of the body weight as treatment courses lasting two to three weeks three times a year.

The drugs of the present invention can be effective for the treatment of endocrinal diseases such as hypothalamic-hypophysial-ovarian associated functional link impairments that can produce hormonal abnormalities and cause sterility. Folliculyl-[succinyl]-GSSG.Pt can be applied by means of IM and subcutaneous injections with a dosage of about 3-10 mg/kg of the body weight, as monthly treatment courses three to four times a year.

Other preferable derivatives include the GSSG.Pt material derivatives in the form of its sodium, lithium, potassium, calcium, zinc, molybdenum, vanadium and other salts, as well as the GSSG.Pt derivatives obtained through covalent binding to phenylalanine, or to methionine and some other aminoacids including D and L forms of the aminoacids herein; or to cystamine, lipoic acid, or to inosine.

In one embodiment, manifestation of the immunological, biochemical and molecular-biological effects of the GSSG.Pt therapeutical impact can be obtained in the case when a combination comprising 50% of GSSG.Pt with all aminoacids in L-form and 50% of GSSG.Pt with two chemically equal aminoacids being represented in D-form and others being represented in L-form is used.

The present invention presents the advantageous feature that the drug comprising the composite or derivatives thereof has a regulating effect on the endogenous cytokine production processes and, thus, on the proliferation and differentiation processes of the T- and B-lymphocyte subpopulations ($CD^+$-cells). Drug induction can result in production of a wide cytokine and hemopoietic factor range and $CD^+$-lymphocytes. Therefore, in this range, from the point of view of cytokine interaction, there are both agonist-cytokines and antagonist-cytokines regarding the effects they stimulate (e.g., "relationship" of IL-1α and β and IL-4). In connection with that, depending on the initial patient's immunogenesis system state, hyper- or hypoactivity, the drugs of the present invention can restore a disturbed balance in the system.

The given provision is illustrated in Examples 9-13 which show that patients with depressed immunity (oncological patients receiving radiation or combined chemotherapy) the cytokine synthesis induction (IL-1α and β, IL-2, IL-3, IL-4, IL-6, IL-10 and IL-12, IFN-α and IFN-γ) can be accompanied by restoration of $CD3^+$, $CD4^+$, $CD8^+$, $CD16/56^+$, $CD25^+$, $CD34^+$ counts; and patients with the immunoautoagression signs—at the clones of cytotoxic lymphocytes or fibroblasts in case of viral hepatitis C the Fas-Ag ($CD95^+$) is expressed that promotes the apoptosis mechanism induction and elimination of the virus-transformed and/or "aggressive" cells.

Another advantageous feature of the present invention involves the finding of the composite impact on the isolated human lymphocytes 10 minutes (a peak is observed at the $30^{th}$ minute (the maximal level of phosphorilating of the cytosol proteins obtained from the lymphocytes)) after parenteral introduction of GSSG.Pt material, a significant increase of the phosphorylating level on tyrosine for lymphocyte cytosole proteins that is an integrative characteristic for the cellular signal-transducing system activity. These changes in state for key factors of cAMP, cGMP, inositol-phosphate-dependent signal systems owing to the GSSG.Pt material influence (See Example 8) calls forth the redox-sensitive gene expression, first of all, for the immunologically significant genes responsible for the cytokine and hemopoietic factor synthesis. Therefore, the GSSG.Pt material application in the treatment purposes not only stimulates the cytokine and hemopoietic factor endogenous production but also provides reproduction of the biochemical and physiological cytokine effects, in particular, in the case of sensitivity loss of receptors to cytokines that is observed at oncological and retroviral pathology.

In the tumor- and/or virus-transformed cells the apoptosis mechanisms are induced through the GSSG.Pt material multicytokine-activating impact, its influence on p53-dependent and p53-independent apoptosis induction mechanisms as well as through changing of the donor/acceptor π-electron balance in malignant (cancer) cells (see Examples 14-16).

Depending on the initial patient's biological status including his immunity condition: immunodeficiency, i.e., hyporeactivity; or immunoautoaggression, i.e., hyperreactivity; presence of the tumor- or virus-transformed cells—the composite and/or pharmaceutically acceptable derivatives thereof are able to act as the endogenous cytokine production stimulators/modifiers and/or as the apoptosis mechanism inducers, respectively.

These compounds and the drug forms thereof obtained which include the GSSG.Pt material composite are applied as medicinal drugs capable in the therapeutic purposes depending on the initial subject's biological status of the subject in need thereof to stimulate/modulate the wide range cytokine and hemopoietic factor endogenous production and/or to reproduce the cytokine effects as well as to perform the differentiated effect regarding the normal (the metabolism, proliferation and differentiation regulation) and the transformed cells (the apoptosis mechanism induction). "Transformed cells" refers to tumor- and/or virus-transformed cells.

Performed experimental and clinical investigations show that therapeutic effects of the drugs obtained from the GSSG.Pt material and derivatives thereof are based on the multicytokineactivating action and capacity to reproduce cytokine and hemopoietic factor effects. At the same time, the data was obtained indicating the GSSG.Pt material has a direct antitumor effect, especially regarding GSSG.Pt material salts administered in pharmaceutically acceptable drug forms. Moreover, the GSSG.Pt material effect has revealed to be different for normal and tumor cells. The research with use of the normal and tumor cells demonstrated that the GSSG.Pt material or the GSSG.Pt material in pharmaceutically acceptable compositions initiated tumor cell death through apoptosis mechanism. In case of normal cells, they did not undergo destruction (See Examples 14-16).

Also high effectiveness of the applied medicinal drugs based on the GSSG.Pt material in regard to apoptosis mechanism induction in the virus-transformed cells, for example, in case of viral hepatitis B and C, should be noted as exemplified in Examples 11-13.

Therapeutic effects of GSSG.Pt material and pharmaceutically acceptable derivatives thereof, particularly, salts thereof for the treating of oncological, infectious (viral) diseases can be explained as a stimulation of the wide-ranged endogenous cytokine production with a unique ability to activate apoptotic death of the transformed cells exclusively. Moreover, the majority of the GSSG.Pt therapeutical effects and the pharmaceutically acceptable derivatives thereof in the experimental and clinical conditions can be applied to be connected with revealed properties of the GSSG.Pt material and the drug forms thereof to stimulate/beneficially modulate the endogenous cytokine production or to reproduce their effects in regard to stimulation of the normal cell proliferation and differentiation and, at the same time, to activate apoptotic death of the transformed cells exclusively.

Another advantageous feature of the drugs of the present invention is a correcting influence of the GSSG.Pt material and the salts thereof on the metabolic abnormalities, particularly, on the impairment of carbohydrate metabolism at diabetes, type II. In this case (See Example 7) restoration of the normal cAMP/cGMP ratio as well as the thiol-disulfide ratio in tissues due to the GSSG.Pt material impact (vanadium salt thereof) provided stable setting to normal values for the glucose content in the patient blood, which is a considerable therapeutic effect.

Resuming the results of performed experimental, preclinical and clinical studies of the medicinal remedies group developed on the GSSG.Pt material one should emphasize that the parenteral (intravenous, intramuscular, subcutaneous, instillations into urinary bladder or per rectum, etc.) introduction of the indicated medicinal remedies provides: a) stimulation/beneficial modulation of the endogenous production of IL-1$\alpha$ and $\beta$, IL-2, IL-3, IL-4, IL-6, IL-8, IL-10 and IL-12, TNF-$\alpha$, IFN-$\alpha$ and IFN-$\gamma$, erythropoietin, G-CSF, M-CSF and GM-CSF; and, thereupon, wide range of biochemical and immunological effects; b) reproduction of the effects of the said cytokines and hemopoietic factors in case of cytokine receptor desensitization; as well as—c) induction of apoptosis mechanism in tumor- or virus-transformed cells only, calling forth in the organism of the subject in need thereof the corresponding therapeutic effect.

Figure 25:
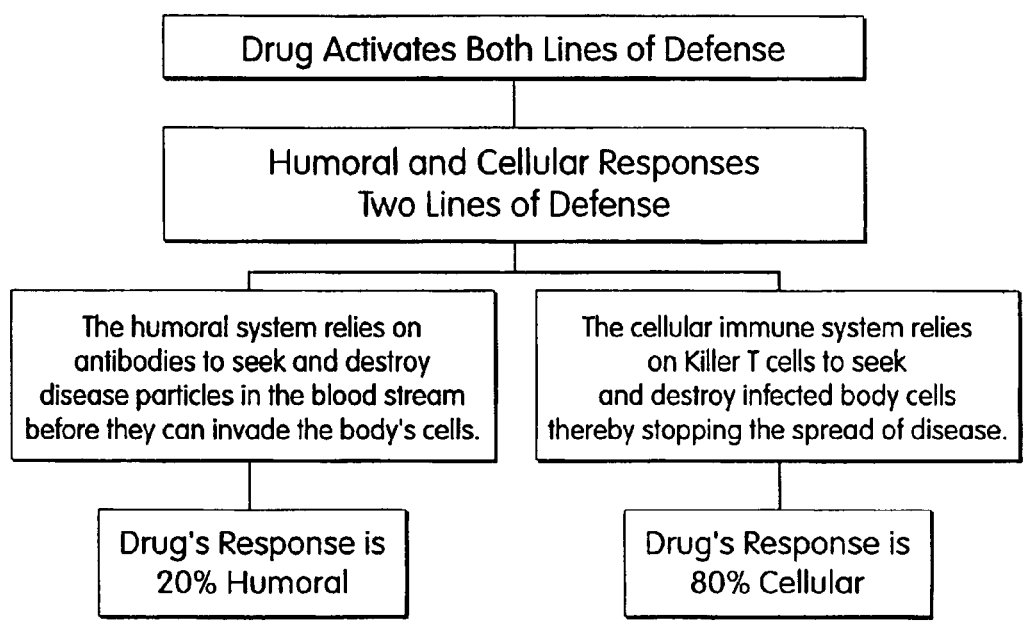
FIG. 25 shows a chart of immune system response to cancers and diseases.

The beneficial effects of the drug of the present invention can be illustrated in FIGS. 25-27. FIG. 25 delineates the humoral and cellular responses to the drugs comprising the composites of the present invention. FIG. 26 depicts the components of the immune system activated by the drugs of the present invention, the components including platelets, white blood cells, red blood cells, cytokines, erythropoietines, T-lymphocytes, neutrophils, monocytes, macrophages, natural killer cells, and $\beta$-lymphocytes. FIG. 27 depicts the types of cytokines stimulated by the drugs of the present invention, the cytokines including IL-1, IL-2, IL-4, IL-6, IL-8, IL-10, IL-12, alpha and gamma interferons, TNF-alpha and GM-CSF. Thus, the novel method for obtaining the composite comprising the GSSG.Pt material the new medicinal substance (thiopoietins) class is applied and proved, in that therapeutical effects are determined by firstly found and previously unknown properties of performing stimulation of cytokine and hemopoietic factor endogenous production and their effect reproduction, thereby, performing stimulation and/or modulation of the normal cell proliferation and differentiation as well as inducing apoptosis mechanisms in virus- and tumor-transformed cells.

The presence of a chemical interaction between the disulfide bond of the oxidized glutathione-based compound and the platinum material may play a biophysical role in the electron balance of biological systems. While not wishing to be bound by any theory, the chemical interaction can be loosely thought of as a donor/acceptor pair where the lone electron pairs on the sulfur atoms can potentially interact with an electron-deficient material, such as the platinum material. Again, while not wishing to be limited by any mechanism, if cellular activity and cellular physical state are determined, at least in part, by donor/acceptor interactions throughout a biological system, then a balance among electron donors and acceptors having equal biopotentials can be a life parameter. Such balance alteration can be used for regulation of different cell functions and physical properties (Szent-Gyorgyi A., Proc. Natl. Acad. Sci. U.S., 58, 2012 (1967); Introduction to a Submolecular Biology, Academic Press, New York (1960)). Sources of mobile electrons can include $\pi$-electrons such as lone-pair electrons of nitrogen, oxygen, and sulfur. There are few acceptor groups (e.g., —C═O-groups) in a normal cell which can be balanced via donor/acceptor dynamics of donor electrons such as $\pi$-electrons.

Continuing along with this non-limiting theory, the malignant cell can be characterized as having dramatic disturbances of the donor/acceptor balance towards an excess of donors electrons. Acceptor molecules are almost absent in cancer cells. A possible solution to this imbalance in this situation is the presence of molecules that possess donor/ acceptor features within the same molecule, such as a GSSG.Pt material. Introducing GSSG.Pt into biological media can cause a restoration of the electronic balance in the biological media. This restoration can involve a catalysis by the platinum atom in a reaction involving the formation of an active oxygen form, e.g., superoxide anion radicals, singlet oxygen.

Another non-limiting theory involving cellular electronic balance is an interaction of GSSG.Pt material with cell GSH generating oxidative-reductive, i.e. donor/acceptor pair. If there is a high GSH level in cells that is characteristic for tumor-transformed cells with a high proliferative impulse, the pro-oxidative, i.e. oxidative, properties of GSSG.Pt material exhibit in the most evident way. In the case the oxidative stress forms in the tumor cells only causing alteration of the tumor cells mitochondria functions forming intracellular signal for the apoptosis mechanisms induction.

For the normal but "tired", "exhausted" cells, there may be an oxidative-reductive potential optimization, bioenergetic supply for the metabolic transformations, redox-sensitive adequate expression of the genome functional sites, in particular, the immunologically significant genes and transcription factors.

For the transformed cells GSSG.Pt, there may be an incompatibility with vital functions involving chain transfer reaction of π-electrons, disturbance of the mitochondrial oxidative-reductive reactions of electron/protons transfer reactions along the respiratory chain and dislocation of the $NADP.H^+/NADP.H$ ratio, i.e., forming the intracellular signal for the apoptosis mechanism induction.

The new GSSG.Pt pharmacokinetics (comparing to GSSG by itself) in blood and tissues (organs) being introduced into biological media indicates that the GSSG.Pt molecule is much less available for the GSSG metabolism enzymes and, first of all, for the $NADP.H^+$-dependent reductase, the main enzyme for the GSSG into GSH reduction. Thereupon, the GSSG.Pt half-life time in the disulfide form in biological media increases significantly (See Examples 3 and 4).

Basically novel pharmacokinetics of the hexapeptide with the stabilized disulfide bond (GSSG.Pt) compared to the structural analog, i.e., the oxidized glutathione (GSSG), provided an optimal manifestation for the newly determined biological-pharmacological effects.

EXAMPLES OF THE INVENTION EMBODIMENTS

SYNTHESIS METHOD. 170 g (0.55 mole) of the reduced glutathione are suspended in 200 ml of water and, along with stirring, 139 ml (0.55 mole) of the 4N NaOH solution and 170 ml of 0.05% cis-diamminedichloroplatinum cis-$[Pt(NH_3)_2Cl_2]$ water solution are added.

The obtained transparent, slightly yellow solution is cooled to 18-20° C. and 283 ml of the 3% hydrogen peroxide solution ($H_2O_2$ solution) is added in little portions over a time period of five minutes with such a speed rate that the reaction mixture temperature will not exceed 22-25° C.

Thirty minutes after addition of the hydrogen peroxide solution ($H_2O_2$) the pH is measured, and then the 4N caustic soda solution is added drop-by-drop to reach pH=5.6-5.8 along with simultaneous temperature control, which should be within 22-25° C. Then the cooling is taken away and stirring continued at indoor (room) ° C. temperature for 30 minutes more.

Control of the oxidation reaction completeness is performed by the HPLC assay. A liquid chromatograph for HPLC, type Beckman, Sol. Module 126, Det. 168, with a column Luna Phenomenex ODS 4.6×250 mm, or an identical one, is prepared. To prepare the HPLC mobile phase 20 $cm^3$ of acetonitrile and 1 $cm^3$ of freshly distilled trifluoroacetic acid is introduced into a 1000-$cm^3$ graduated flask, and the volume is increased up to the mark by the deionized water. The solution is mixed and degassed by shaking in vacuum.

Thirty minutes after addition of the entire hydrogen peroxide solution amount one will check the oxidation reaction completeness by means of the highly productive liquid chromatography (HPLC). Thereto with a microsyringe one will take 10 μl of the reaction mixture and dissolve them in 1 ml of the mobile phase (0.1% trifluoroacetic acid:acetonitril, 98:2). 20 μl of the obtained solution is introduced into the chromatograph Beckman 126 Solvent Module, Diod Array Detector Module 168, the column Luna Phenomenex ODS 4.6×250 mm, or the identical. Elution is performed in isocratic regime, 30 min., in the system 0.1% trifluoroacetic acid:acetonitrile, 98:2; the flow-speed rate 1 ml/min, detection at 220 nm, scanning 190-600 nm.

The retention time in the aforesaid conditions is 5.0+0.5 min for reduced glutathione, 11.0±0.5 min for oxidized glutathione.

In case if, according to the HPLC data after the standard chromatogram integration, the oxidized glutathione content is less than 97%, the stirring is continued in the same regime 30 minutes more and the HPLC control is repeated.

In case when the result is equal or exceeds 97%, the reaction is considered as completed and one will pass to the reaction solution filtration. Thereto, there is used a filter having pore size not larger than 0.7 μm.

Weight loss at drying will not exceed 5% at drying to the constant weight at 100° C. in vacuum (1 mm Hg) above $CaCl_2$ and $P_2O_5$.

The main material content in the ready product by the HPLC data will not be lower than 98%.

Thus, the oxidized glutathione as a composite with cis-diamminedichloroplatinum is obtained.

Appearance: white odorless powder.

Solubility: soluble in water, 0.9% isotonic solution of sodium chloride for injections; insoluble in 95% alcohol, chloroform, ether and other organic dissolvents.

Solution transparency and color: 0.05 g of the drug solution in 10 ml of water is transparent and colorless solution.

PH of 1% solution: 5.0-6.0 potentiometrically, the device is pH/mV/°C. meter Cole Parmer, model 59003-15 or identical.

Authenticity:

a) amino-acid analysis (6 n HCl, 110° C., 20 hrs.), glycine—2.0±15%; glutamic acid—2.0±15%; cysteine—2.0±40%; amino-acid analyzer AAA T-339 M Prague or identical.

b) HPLC—at the outlet time it corresponds to the standard of bis-(γ-L-glutamyl)-L-cysteinyl-bis-glycine disodium salt.

Chromatography conditions: device—BECKMAN "Gold Nouveau Chromatography Data System" Version 6.0, Diod Array Detector Module 126 or identical.

Assay—20 μl of 0.1% drug solution in the mobile phase, chromatography on the column ULTRASPERE ODS 250× 4.6 mm with the converted $C_{18}$ phase in the isocratic conditions acetonitrile—0.1% trifluorideacetic acid (2:98); flow rate 1 ml/min., detecting at 220 nm, scanning 190-600 nm.

Purity (Main Substance Content):
  a) at HPLC not less than 98%:
  b) at the amino-acid analysis: not less than 85% (analysis according to Section "Authenticity", Item "a" with an exact weight).
  c) Sodium (Na) content according to the emission spectral method is 7.0±0.5%.
  d) Platinum (Pt) content according to the mass spectrometric analysis is 0.032±0.01%

Method for Element Content Determination:

The exact assay weight (about 50 mg) is dissolved in 50 ml of bidistilled water and the solution is used for the analysis.

The platinum content is determined quantifiably by the method of mass spectrometric analysis with inductively bound plasma at the device of the PQe model made by VG Elemental, England. The analysis relative precision is 5%.

The other element content is determined quantifiably by the method of the atomic-emission spectroscopy with inductive bound plasma on the device of the model TRACE 61E made by Thermo Jarell Ash, USA. The analysis relative precision is 5%.

| Element content, µg/g: | |
|---|---|
| Silver (Ag) | <1.0 (less than 0.0001%) |
| Aluminum (Al) | 2.0 |
| Arsenic (As) | <1.0 |
| Barium (Ba) | <0.50 |
| Beryllium (Be) | <0.05 |
| Calcium (Ca) | 7.0 |
| Cadmium (Cd) | <0.05 |
| Cobalt (Co) | <0.5 |
| Chromium (Cr) | 1.7 |
| Copper (Cu) | <0.5 |
| Iron (Fe) | <1.0 |
| Potassium (K) | <2.5 |
| Selenium (Se) | <2.0 |
| Magnesium (Mg) | <2.5 |
| Manganese (Mn) | <0.2 |
| Molybdenum (Mn) | <0.2 |
| Nickel (Ni) | <0.5 |
| Lead (Pb) | <0.40 |
| Strontium (Sr) | 1.9 |
| Titanium (Ti) | <0.5 |
| Vanadium (V) | <0.5 |
| Zinc (Zn) | 0.65 |
| Antimony (Sb) | <0.5 |

Example 1

Synthesis of bis-(L-phenylalanyl-γ-L-glutamyl)-L-cysteinyl-bis-glycine Disodium Salt (I.) General Drug Characteristics.

1. Name: bis-(L-phenylalanyl-γ-L-glutamyl)-L-cysteinyl-bis-glycine disodium salt, composite with cis-diamminedichlorplatinum.

2. Structural formula—see FIG. 8.

3. Gross-formula: $C_{38}H_{48}N_8O_{14}Na_2S_2 \cdot [Pt(NH_3)_2Cl_2]$

4. Molecular weight: 950.94 on $C_{38}H_{48}N_8O_{14}Na_2S_2$ with Pt content 0.033%.

5. Appearance: white odorless powder.

6. Solubility: soluble in water, 0.9% isotonic solution of sodium chloride for injections; insoluble in 95% alcohol, chloroform, ether and other organic dissolvents.

7. Solution transparency and color: 0.05 g of the drug solution in 10 ml of water is transparent and colorless.
8. pH of 0.1% solution: 5.75 (potentiometry).
9. Authenticity:
  a) amino-acid analysis (6 n HCl, 110° C., 20 hrs.), (error margin 20%, for cysteine—35%), in correspondence: glycine—2.00; glutamic acid—1.92; cysteine—1.81; phenylalanine—2.04.
  b) NMR($^1$H)-spectroscopy, according to—"BRUKER" AM 500, 500 MHz, $D_2O$.

| δ | | Amino-acid |
|---|---|---|
| 7.20 | —$C_{ar}$—H | Phe |
| 4.70 | —$C_\alpha$H— | Cys |
| 3.75 | —$C_\alpha$H— | Glu |
| 3.27 | —$CH_2$— | Gly |
| 2.95 | —$CH_2$— | Cys |
| 2.52 | —$CH_2$— | Glu |
| 2.15 | —$CH_2$— | Glu |

10. Purity (main substance content):
  a) At HPLC not less than 97%:
  Device: BECKMAN "Gold Nouveau Chromatography Data System" Version 6.0, Diod Array Detector Module 126. Assay—20 µl of 0.1% drug solution in the mobile phase, chromatography on the column ULTRASPERE ODS 250× 4.6 mm with a converted $C_{18}$ phase in isocratic conditions acetonitrile—0.1% trifluorideacetic acid (2:98); flow rate 1 ml/min., detecting at 220 nm, scanning 190-600 nm, PDA functions—Contour Plot, 3D.
  b) At the amino-acid analysis: not less than 85% (analysis according to Item 9a with an exact weight);
  c) Thin-layer chromatography is homogenous, analysis is performed at introduction of 5 µl of the 1% drug solution in the band. There are plates Kieselgel $60_F$ (Merck) 10×5 cm, system: n.butanol-acetic acid-water (4:1:1). Development is performed according to the standard methods—ninhydrine and chlorine\benzidine. $R_f$=0.15;
  d) Sodium (Na) content according to the emission spectral method is: 4.8%;
  e) Platinum (Pt) content according to the mass spectrometric analysis is 0.033%.

| 11. Elements detected content, µg/g: | |
|---|---|
| Silver (Ag) | <1.0 (less than 0.0001%) |
| Aluminum (Al) | 2.0 |
| Arsenic (As) | <1.0 |
| Barium (Ba) | <0.50 |
| Beryllium (Be) | <0.05 |
| Calcium (Ca) | 7.0 |
| Cadmium (Cd) | <0.05 |
| Cobalt (Co) | <0.5 |
| Chromium (Cr) | 1.7 |
| Copper (Cu) | <0.5 |
| Iron (Fe) | <1.0 |
| Potassium (K) | <2.5 |
| Selenium (Se) | <2.0 |
| Magnesium (Mg) | <2.5 |
| Manganese (Mn) | <0.2 |
| Molybdenum(Mo) | <0.2 |
| Sodium (Na) | 48 mg/g |

-continued

| 11. Elements detected content, µg/g: | |
|---|---|
| Nickel (Ni) | <0.5 |
| Lead (Pb) | <0.40 |
| Platinum (Pt) | 330 µg/g |
| Strontium (Sr) | 1.9 |
| Titanium (Ti) | <0.5 |
| Vanadium (V) | <0.5 |
| Zinc (Zn) | 0.65 |
| Antimony (Sb) | <0.5 |

Determination Method:

The exact assay weight (about 50 mg) is dissolved in 50 ml of double-distilled water and the solution is used for the analysis.

The platinum content is determined quantifiably by the method of mass spectrometric analysis with inductively bound plasma at a PQe device made by VG Elemental, England.

The analysis relative precision is 5%.

The content of other elements is determined quantifiably by the method of the atomic-emission spectroscopy with inductive bound plasma on a TRACE 61E device made by Thermo Jarell Ash, USA. The analysis relative precision is 5%.

12. Weight loss at drying: 10% at drying till the constant weight at 100° C. in vacuum (1 mm Hg) above $CaCl_2$ and $P_2O_5$.

(II.) Synthesis Method Description.
  1. Process chemical scheme—see FIG. 8.
  2. Method description (III). Product (I) γ-L-glutamyl-L-cysteinyl-glycine in amount of 3.07 g (10 mmol) and N-hydroximethylbenzamide (II) in amount of 5.89 g (13 mmol) is dissolved in 30 ml of anhydrous trifluoroacetic acid (TFA) mix at the room temperature during one hr. Then the solvent is distilled off in vacuum at 40° C., 30 ml of anhydrous ethyl alcohol is added to the remainder; the solvent is again distilled off in vacuum and the procedure is repeated two times more. The product is crystallized through grinding in 50 ml of anhydrous diethyl ether, filtered, washed on the filter with 2×20 ml of anhydrous ether and further it is dried in vacuum above KOH and $P_2O_5$. Recrystallization is done from 90% ethanol. Yield—5.50 g (80%). $R_f$=0.43, Kieselgel 60$_f$ (Merck) 10×5 cm, system: n.butanol-acetic acid-water (4:1:1).

(V). Product (III) in amount of 4.40 g (10 mmol) is stirred in the mixture of 15 ml of distilled water and 25 ml of dioxane; then along with mixing, 10 ml (20 mmol) of 2 N NaOH solution is added.

Then 3.62 g (10 mmol) of phenylalanine N-hydroxysuccinimide ester (IV) is introduced in the reaction mixture and the stirring is continued during 12 hrs at room temperature. Then the mixture is evaporated in vacuum at 40° C. to dryness. The residue is dissolved in 200 ml of ethyl acetate and washed by 2×20 ml of 1 N sulphuric acid, water, sodium bicarbonate (2×50), water and the organic layer is above the anhydrous chloride calcium. Then ethyl acetate sis distilled in vacuum at 40° C. to dryness and the product is crystallized from ethyl acetate/ether.

The crystals are separated by filtration and dried in vacuum above phosphorus pentoxide to constant weight. The product yield (V)—4.88 g (70%). $R_f$=0.80, Kieselgel 60$_f$ (Merck) 10×5 cm, system: n.butanol-acetic acid-water (4:1:1).

(VI). Product (V) in amount of 6.87 g (10 mmol) is dissolved in 20 ml of distilled trifluoroacetic acid and the solution is kept at room temperature during two hrs. Then the product is precipitated by absolute ether (about 200 ml), filtered and dried in vacuum above KOH to the constant weight. The product yield—(V) 5.28 g (90%). $R_f$=0.48, Kieselgel 60$_f$ (Merck) 10×5 cm, system: n.butanol-acetic acid-water (4:1:1).

(VII). Product (IV) in amount of 5.87 g (10 mmol) is dissolved in 100 ml of a mixture methanol-water (1:1), then 200 ml (10 mmol) of mercury acetate solution are added and the mixture is stirred at room temperature during one hr. Then the hydrogen sulphur flow is sparged through the solution during 20 min. controlling precipitation efficiency at the assay. The mercury sulphide precipitate is filtered; the filtrate is evaporated in vacuum up to volume of 10 ml; then 200 ml of isopropyl alcohol is added and the product is crystallized at cooling to 0-4° C. The crystals are filtered, washed with isopropyl alcohol, acetone and dried in vacuum above $P_2O_5$. The product yield (VII)—3.72 g (82%). $R_f$=0.30, Kieselgel 60$_f$ (Merck) 10×5 cm, system: n.butanol-acetic acid-water (4:1:1).

(VIII). Product (VII) in amount of 4.54 g (10 mmol) is suspended in 20 ml of water and along with stirring, 5 ml (10 mmol) of 2 N NaOH solution and then 4.8 ml of 0.05% water solution of cis-diamminedichloroplatinum (cis-[Pt$(NH_3)_2Cl_2$]) is added. The solution is cooled to 18-20° C. and in little portions during about two min., 5.1 ml of 3% solution is added at such a rate so that the temperature will not exceed 22-25° C. Thirty minutes after introduction of the whole hydrogen peroxide amount, the solution pH is measured and its value is brought to 5.6-5.8 by adding of the necessary amount of 4N NaOH solution, while the solution temperature is monitored (it is within 22-25° C.). Then the stirring is continued without external cooling for 30 min. and then the control analysis of the reaction mixture is performed by HPLC. With that purpose 10 µl is taken out of the reaction solution and dissolved in 1 ml of the mobile phase. If, according to the HPLC data, the oxidized form content is equal or exceeds 95%, the reaction is deemed as finished. Otherwise, the stirring at the room temperature is continued 30 min. more and the HPLC assay is repeated.

Then the reaction solution is filtered through the filter with pore size not larger than 0.7 µm and the filtrate is lyophilized. The obtained dry product is dried out in vacuum at 40° C. above anhydrous calcium chloride to the constant weight. Yield—4.51 g (95%).

The ready substance is analyzed according to see Example 2.

Example 2

Figure 9:
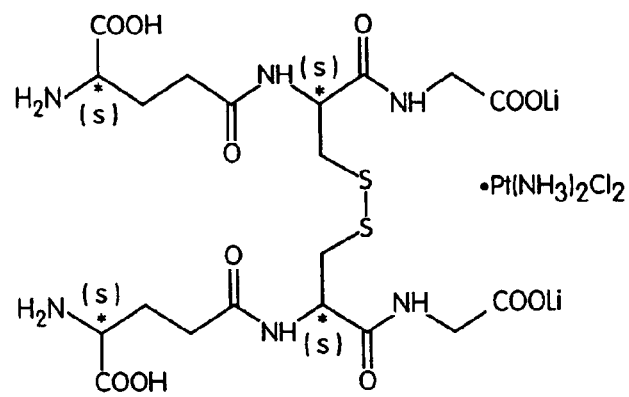
FIG. 9 shows the structure of lithium salt of bis-(γ-L-glutamyl)-L-cysteinyl-bis-glycine.

Synthesis of bis-(γ-L-glutamyl)-L-cysteinyl-bis-glycine lithium salt (I.) General Drug Characteristics.
  1. Name: bis-(γ-L-glutamyl)-L-cystinyl-bis-glycine dilithium salt with cis-diamminedichloroplatinum.
  2. Structural formula—see FIG. 9.
  3. Gross-formula: $C_{20}H_{30}N_6O_{12}Li_2S_2\cdot[Pt(NH_3)_2Cl_2]$
  4. Molecular weight: 624.49 on $C_{20}H_{30}N_6O_{12}Li_2S_2$ with Pt content 0.032%

5. Appearance: white odorless powder.
6. Solubility: soluble in water, 0.9% isotonic solution of sodium chloride for injections; insoluble in 95% alcohol, chloroform, ether and other organic dissolvents.
7. Solution transparency and color: 0.05 g of the drug solution in 10 ml of water is transparent and colorless.
8. pH of 0.1% solution: 5.0-6.0 (potentiometry).
9. Authenticity:
   a) amino-acid analysis (6n HCl, 110° C., 20 hrs.) in correspondence: glycine—2.0 (2.0); glutamic acid—1.9 (2.0); cysteine—1.7 (2.0).
   b) NMR($^1$H)-spectroscopy, in correspondence: $CH_2$ (δ 2.05, 2.40, 3.00, 3.80); CH (δ 3.72, 4.65).
   c) HPLC corresponds with the standard according to the yield time.
10. Purity (main substance content):
    a) at HPLC>95%;
    b) at the amino-acid analysis >85%;
    c) Thin-layer chromatography (TLC) homogenous;
    d) Lithium (Li) content according to the emission spectral method is 2.2±0.1%
    e) Platinum (Pt) content according to the mass spectrometric analysis is 0.01-0.02%

(II.) Staged Scheme for the Product Synthesis (A→B→C)

A. Oxidation of Reduced Glutathione (γ-L-glutamyl-L-cysteinyl-glycine)

Figure 10:
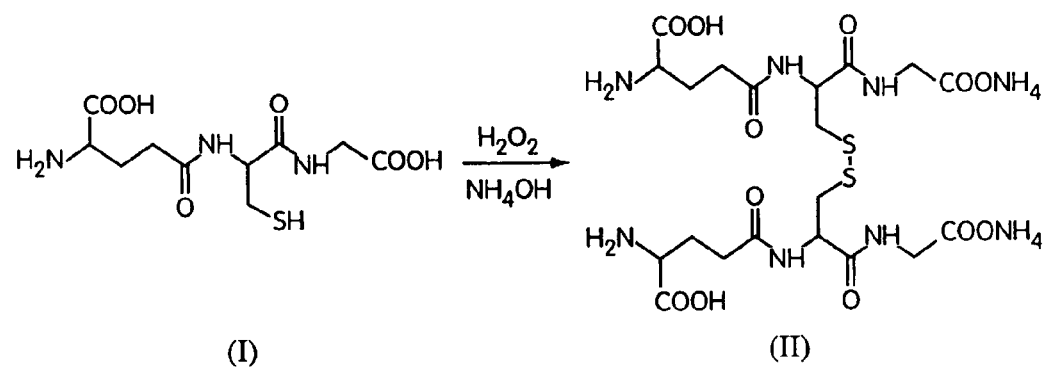
FIG. 10 shows the stage of processing of the source reduced glutathione with hydrogen peroxide at pH=8 (stage of the synthesis scheme for the GSSG.Pt lithium salt)

$A_1$—stage for the source reduced glutathione processing by hydrogen peroxide at pH=8—see FIG. 10.

Source compound (I): γ-L-glutamyl-L-cysteinyl-glycine (GSH)

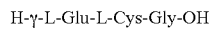

Reagents:
1) hydrogen peroxide (35%) Fluka
2) ammonia solution (25%)

Reaction conditions: stirring of the water solution (I) and the reagents at 20° C. (pH=8.0) during 20 min.

Figure 11:
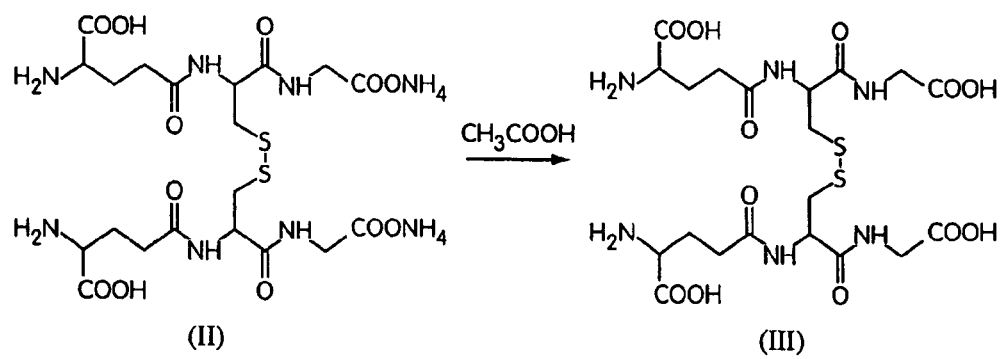
FIG. 11 shows the extraction of the free hexapeptide bis-(γ-L-glutamyl)-L-cysteinyl-bis-glycine (III, stage of the synthesis scheme for the GSSG.Pt lithium salt)

$A_2$—separation of free hexapeptide bis-(γ-L-glutamyl)-L-cysteinyl-bis-glycine (see FIG. 11)

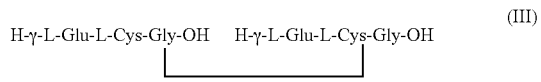 (III)

Source compound: reaction mixture of the A1 stage.
Reagents: glacial acetic acid
Reaction conditions: acidification of the $A_1$ reaction mixture by glacial acetic acid up to pH=5.0, the solution filtration and lyophilic drying of the product.

Control for the A oxidation stage processing: by HPLC at the Delta Pack C18 column (0.1% TFA-MeCN, 0-25%); one will check presence of the peak (>97%) for the compound (III) (7.4±0.4 min) and the peak absence for the compound (I) (3.0±0.3 min).

Figure 12:
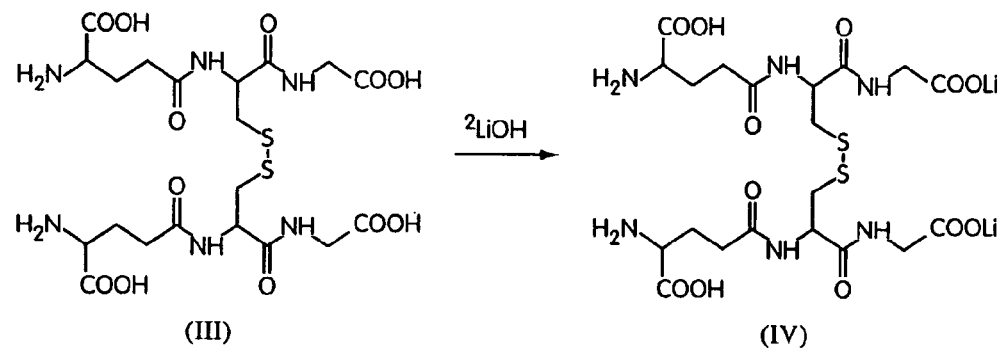
FIG. 12 shows the transfer of the oxidized GSSG (III) form in the lithium salt of the GSSG.Pt.

B. Conversion of the Oxidized Form (III) into the Lithium Salt (IV)—see FIG. 12.
Source compound: free hexapeptide (III).
Reagents: 1 N LiOH solution.
Reaction conditions:
  a) titration of the compound (III) water solution by two LiOH equivalents;
  b) water evaporation in vacuum at 35-40° C.;
  c) the product precipitation by isopropyl alcohol;
  d) precipitate filtration;
  e) precipitate washing by acetone;
  f) the product drying in vacuum (1 mm Hg) at 35-40° C.

Control of the B stage processing: the reagents quantities and technological conditions at drying is inspected.

C. Finished Product Quality Control.
1. The main material content according to HPLC: >97%.
   The analysis is performed using 20 μl of 0.1% drug solution in the mobile phase, on the column 250×4.6 mm with a converted $C_{18}$ phase in isocratic conditions acetonitrile—0.1% trifluorideacetic acid (2:98); flow rate 1 ml/min., detecting at 220 nm. The comparison is made with the standard peak obtained in the same conditions.
2. The main material content according to the spectrophotometric analysis data on the non-oxidized thiol groups content: >95%.
   Analysis: 0.12 ml of 0.5% drug solution is placed into a 25-ml measuring flask, 1 ml of 0.1% Tris-HCl buffer with pH=8, 0.01 M EDTA and 1 ml of 2% $NaBH_4$ solution. The reaction mixture is incubated at 20° C. during 30 min. The reaction is terminated through introduction of 0.6 ml of 1 M HCl during two min. in portions of 0.05 ml along with agitation and following introduction of 2 ml of acetone during three min. with stirring. Then 0.25 ml of the Elman reagent is added and the volume is brought to the mark by 0.1 M the phosphate buffer solution (pH 8.0). An optical density is measured at 412 nm, water is a comparison solution. Simultaneously, the procedure with the drug standard is conducted and the obtained data is compared.
3. Presence of foreign admixtures: according to TLC data the drug is homogenous.
   Analysis is performed at introduction of 5 μl of the 0.1% drug solution in the band. The plates are Kieselgel $60_f$ (Merck) 10×5 cm, system: n.butanol—pyridine—acetic acid—water (150:100:30:120). Development is performed according to the standard methods—ninhydrine and chlorine\benzidine.
4. Lithium (Li) content according to the emission spectral method is 2.2±0.1%.

Example 3

Pharmacokinetics and Metabolism of GSSG.Pt and GSSG in Blood Serum and Tissues After Intravenous Introduction The time-concentration GSSG curves and activity changes for enzymes participating at the GSSG metabolism after the GSSG.Pt and GSSG intravenous introduction in different doses were studied. The variation of the oxidized glutathione concentration was evaluated in animal blood serum, liver, kidneys, spleen and lymphocytes during 60 min. after the single GSSG.Pt and GSSG intravenous introduction in doses 2 mg/kg and 20 mg/kg of body weight. In addition, the activity variation of the enzymes participating in GSSG metabolism was evaluated (glutathione reductase, glutathione-peroxidase, glutathione-S-transferase,γ-glutamyl-transpeptidase).

The study was performed at male CBA mice (standard body weight—180 to 200 g). Five groups of animals (with no less than 15 mice in each) were formed. The group description is represented below.

Control Groups:
  #1—intact animals receiving a single injection of the tested article vehicle (normal saline—(NS)) instead of the drug;

Test Groups:

2—animals receiving the GSSG injection (GSSG dissolved in normal saline) in a dose of 2 mg/kg;

3—animals receiving the GSSG injection (GSSG dissolved in normal saline) in a dose of 20 mg/kg;

4—animals receiving the GSSG.Pt injection (GSSG.Pt dissolved in normal saline) in a dose of 2 mg/kg;

5—animals receiving the GSSG.Pt injection (GSSG.Pt dissolved in normal saline) in a dose of 20 mg/kg.

The blood samples were taken at 1, 2, 5, 10, 20, 40 and 60 min., the serum was separated and the concentration analysis was performed according to a standard method where the main stages are protein precipitation, removal from the sample of non-polar and medium-polar compounds and the following chromatographic analysis with spectrophotometric detection in conditions of isocratic and linear gradient elution.

The GSSG content variation in the blood serum, different organs and the lymphocytes at the drug intravenous introduction are given in the Tables 1-4.

Activity of the enzymes participating in the GSSG metabolism (glutathione reductase: EC. 1.6.4.2; glutathione-peroxidase: EC. 1.11.1.9; glutathione-S-transferase: EC.2.5.1.18; g-glutamyl-transpeptidase: EC.2.3.2.2) were determined by the standard reagent kits produced by Boehringer Mannheim GmbH. The enzyme activity variation values after the GSSG.Pt and GSSG intravenous introduction in dose of 2 mg/kg are given at the Tables 5, 6, 7.

Comparing the drug dynamic distribution of the drugs in the blood serum, liver, kidneys, spleen and lymphocytes a clear advantage for the GSSG.Pt pharmacokinetics regarding GSSG is evident. The GSSG concentration to the $10^{th}$ minute is almost equal to the initial one whereas, at the same time, the GSSG.Pt concentration exceeds 50 times the initial parameters and remains at the given high level till the end of the studied period. Besides, the maximal GSSG.Pt concentration in the blood serum and in the tissues exceeds 3 times the maximal GSSG concentration. These features determine higher effective duration of impact for GSSG.Pt comparing to GSSG.

As it follows out of the Tables 5, 6, 7 materials the GSSG drug increases approximately two times the activity for the enzymes participating in the thiol metabolism with large number of proved indices whereas the GSSG.Pt drug does not significantly alter the enzymes activity and the proved indices number is insignificant. It indicates the greater GSSG.Pt drug stability as a substrate in regard to main enzymes participating in the glutathione metabolism and, therefore, calls out longer presence of the glutathione oxidized form in the blood serum and different organs.

Thus, the obtained data analysis demonstrated the higher GSSG.Pt stability to selective impact of the main glutathione metabolism enzymes (first of all, glutathione-reductase) that determines new dynamics for the drug pharmacokinetics. It facilitates manifestation of new biological-pharmacological effects and, thereupon, new GSSG.Pt therapeutic effects.

Example 4

Table A: GSSG Pharmacokinetics (Initial Data)

Figure 23:
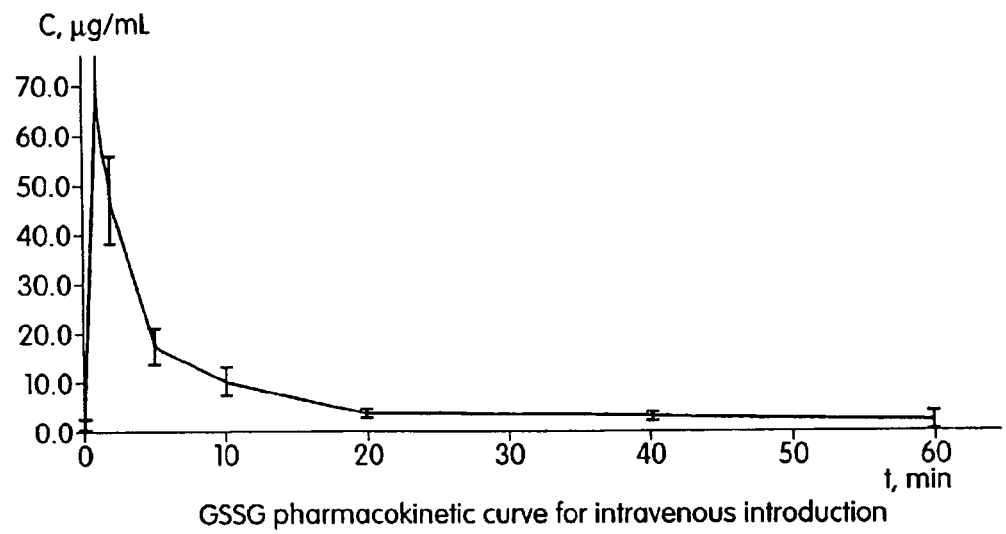
FIG. 23 shows a GSSG pharmokinetic curve for intravenous introduction.

A graph on mean values is presented in FIG. 23, showing a GSSG pharmacokinetic curve for intravenous introduction.

Table B: Pharmacokinetic Parameters

Table C: GSSG.Pt Pharmacokinetics

Figure 24:
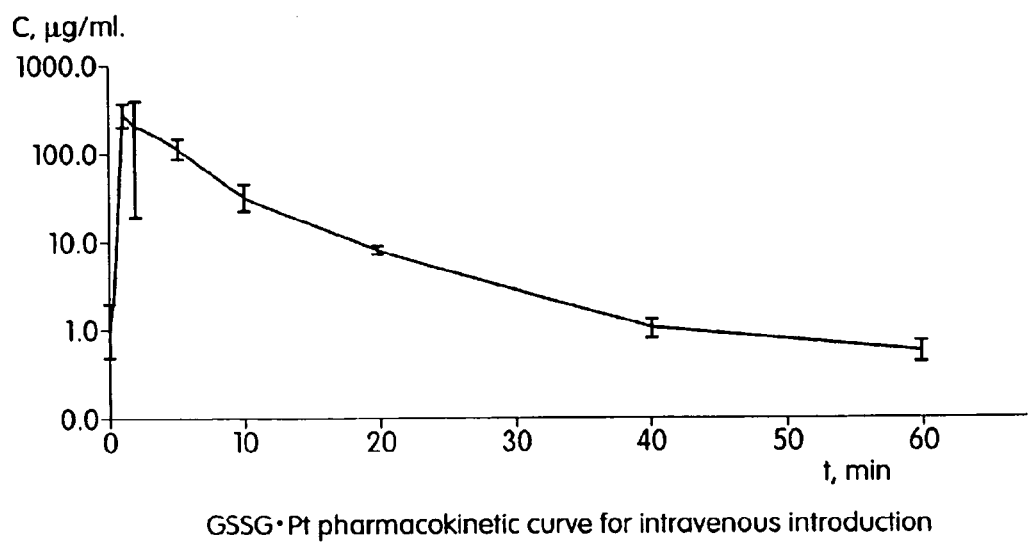
FIG. 24 shows a GSSG pharmokinetic curve for intravenous introduction.

A graph on mean drug concentration values is presented in FIG. 24, showing a GSSG.Pt pharmacokinetic curve for intravenous introduction.

Table D: Pharmacokinetic Parameters.

Example 5

Effect of GSSG.Pt and GSSG on Cytokine Production by Human Peripheral Blood Mononuclear Leukocytes In Vitro Oxidized glutathione (GSSG) as well as a structural analog thereof, which is a hexapeptide with a stabilized disulfide bond, were evaluated for their effect on cytokine production by human peripheral blood mononuclear leukocytes in vitro.

The leukocytic cytokine production was triggered by adding a mitogen, concanavalin A (ConA) to the cell culture immediately after introducing the test substances. In 24 hours of the cellular exposure to ConA and the test articles, the culture supernatants were sampled and stored until cytokine determination at −70° C.

With the aim of evaluating the functional status of the cells and their capacity of responding to the mitogen in the presence of the test articles at each concentration level, the control cell cultures, containing the test articles in identical concentrations, were incubated for 72 hours following the initial concomitant introduction of ConA and the test substances. Sixteen hours prior to the incubation completion, $^3$H-thymidine was added, and the label rate of incorporation into DNA was interpreted as the criterion of the cellular test system functional state.

Venous blood from male healthy volunteers was collected into plastic heparinized tubes (endotoxin tested). PMNL fraction was isolated by centrifugation in density gradient of Ficoll and sodium diatrizoate (Histopaque-1077; Sigma).

Cell concentration was adjusted to $2 \times 10^6$ per 1 mL of culture medium (RPMI 1640, Sigma) containing: HEPES (20 mM); L-glutamine (2 mM); Gentamicin (50 mg/mL); fetal calf serum (10%). All the reagents used were of cell culture tested grade, Sigma. Cell viability was estimated by the Trypan blue exclusion method and 100 mL of cell suspension (200,000 cells) were placed into each well of flat bottom 96-well sterile microtiter plates for tissue cultures. Cells from each subject were placed into no less than 39 wells.

The five following final concentrations of the test articles (GSSG, as well as GSSG.Pt) were evaluated: 5000 mg/mL; 500 mg/mL; 50 mg/mL; 5 mg/mL; and 0.5 mg/mL. Each concentration was established in no less than six wells by adding 50 mL of medium containing the appropriate quantity of the previously dissolved test articles. Another six wells were used for control cultures: only 50 mL of medium was added.

Immediately after the test articles had been introduced into the cultures, 50 mL of medium containing ConA (Sigma, cell culture tested) in a quantity required for a final concentration of 4.0 mg/mL, was added to all the wells excepting three additional ones which served for evaluation of spontaneous $^3$H-thymidine uptake (without ConA).

After a 24-hour incubation at 37° C. and 5% of $CO_2$, contents of three wells (from each sextuplet of identical wells) were taken out, centrifuged, and the supernatants were frozen and kept at −70° C. until the cytokine assay was to be performed. Cultures in the other three wells (of each sextuplet) were incubated further under the conditions described above.

Fifty-six hours after the incubation had begun, 1.0 mCi of $^3$H-thymidine was added into all the remaining cultures, the plates were incubated for another 16 hours, and then the contents of the wells were harvested and transferred onto glass-fiber filters which were consequently treated with 5% trichloroacetic acid and ethanol. The filters were dried and their radioactivity (counts per minute, cpm) was determined using liquid scintillation counter, Betaplate 1205 (LKB).

Mean radioactivity values for triplicates of identical cultures were used to calculate the index of mitogenic stimulation: the ratio of averaged cpm values for ConA stimulated cultures to averaged cpm values for unstimulated ones (three wells without ConA). This stimulation index for wells, where the test articles were present in various concentrations, served as a criterion of cellular functional status, and ability of the cells to respond to mitogenic stimulation.

Supernatants of 24-hour culture triplicates were subsequently assayed for cytokine content only if their 72-hour matched control culture triplicates developed mitogenic response to ConA with value of the stimulation index in the range from 15 to 50.

Concentrations of interleukin-1b (IL-1b), interleukin-2 (IL-2); interleukin-3 (IL-3); interleukin-4 (IL-44); interleukin-6 (IL-6), interleukin-8 (IL-8); interleukin-10 (IL-10); interleukin-12 (IL-12); tumor necrosis factor-α, g (TNF-α, g), and interferon-α, g (IFN-α, g) were determined by ELISA using commercial reagent kits (Medgenix, Belgium) and were expressed in pg/mL of culture supernatants.

The salient findings given in Tables 8, 9. As one can see from Tables 8 and 9, the adding of GSSG and GSSG.Pt into the culture media resulted in statistically significant and dose-dependent stimulation of the cytokine production by human mononuclear leukocytes. However, GSSG.Pt stimulating influence was more significant (1.5-2 times as much) on the studied cytokine production with stimulation and regulation for production of the wider cytokine range in comparison with the GSSG effect. One can clearly see correlation of the interrelated cytokine changes (increasing of IL-1b, IL-2, TNF-α, g along with decreasing of IL-4, IL-10) in the Tables 8 and 9.

Thus, the GSSG.Pt impact on the human peripheral mononuclear leukocytes in vitro was manifested with considerable stimulation of the wider cytokine range release into culture media considering their reciprocal regulative effect, and, thereby, it confirmed the GSSG.Pt stimulatory and regulatory effect on the natural cytokine-producing capacity of the human blood cells.

Example 6

Effect of GSSG and GSSG.Pt on Cytokine and Hemopoietic Factor Production as Well as on Hemopoiesis and Immunity Parameters in Cyclophosphamide-induced Hemo- and Immunodepression 1. The oxidized (GSSG) glutathione as well as the structural analog thereof, which is the hexapeptide with the stabilized disulfide bond, were evaluated in a murine model of hemo- and immunodepression induced by a single administration of cytostatic agent Cyclophosphamide (CP).

The study was designed to evaluate the effect of a five-day long administration of the test articles on the capability of the CP-treated murine splenocytes to produce interleukin-1 (IL-1 α,b); interleukin-2 (IL-2); interleukin-3 (IL-3); interleukin-4 (IL-4); interleukin-6 (IL-6), interleukin-8 (IL-8); interleukin-10 (IL-10); interleukin-12 (IL-12); tumor necrosis factor-α, g (TNF-α, g), interferon-α, g (IFN-α, g) and G-CSF, M-CSF, GM-CSF in vitro. In addition, the blood leukocyte and lymphocyte count and the bone marrow cellularity (karyocyte count) were determined at eight days after CP administration. Some animals receiving CP were then challenged with sheep red blood cells (SRBC), and the humoral immune response to the antigen was evaluated.

Male CBA mice (180 to 200 g body weight) were given a single introperitoneal injection of CP in a dose of 50 mg/kg. Four groups of animals (with no less than 15 mice in each) were formed. The group description is represented below.

Control Groups:

1—intact animals receiving a single injection of normal saline (NS) instead of CP injection, which further were treated with test article vehicle (normal saline);

2—animals receiving a single CP injection, which further were treated with test article vehicle (normal saline);

Test Groups:

3—animals receiving a single CP injection, which further were treated with the test article (GSSG dissolved in normal saline) in a dose of 5 mg/kg;

4—animals receiving a single CP injection, which further were treated with a GSSG.Pt (dissolved in normal saline) in a dose of 5 mg/kg.

Twenty-four hours after the CP injection, five animals in each group were immunized with SRBC ($10^7$ cells in 0.5 mL of NS, intra-peritoneally).

On day 3 after the CP injection (24 hours after the immunization) the intraperitoneal injections of the test or reference articles were started (as it has been described above). Injections were performed during five days: once a day, daily.

Twenty-four hours after the completion of five-day treatment course (on the $8^{th}$ day after the CP injection), mice were euthanized and splenocyte cultures were aseptically prepared for assessment of spontaneous cytokine and hemopoietic factor production by the spleen lymphocytes in vitro.

Simultaneously, blood and marrow samples were collected for blood leukocyte, lymphocyte, and marrow nucleated cell counts.

Serum samples from immunized animals were tested on level of SRBC agglutinins (day 8 after the CP injection, and day 7 after the immunization).

Table 10 shows the parameters of cytokine and hemopoietic factor production by splenocytes, bone marrow and blood count indices, and the immune response to sheep red blood cells in mice receiving the test articles against the background of cyclophosphamide induced hemo- and immunodepression.

According to the Table 10 data, the GSSG.Pt administration set to norm the cytokine and hemopoietic factor production while GSSG performed only exiguous stimulating effect. Besides, GSSG.Pt stimulated production for the wider cytokine and hemopoietic factor range as well as had significant regulatory influence on shift with respect of the cytokine status that was confirmed with the positive correlation of the interrelated cytokine changes at the corresponding pathologic process.

Thus, the GSSG.Pt use in CP-induced hemo- and immunocompromised animals results in a prominent stimulation and regulation on the cytokine and hemopoietic factor endogenous production along with restoration of the bone marrow and blood cellular indices as well as immune response development to sheep red blood cells.

2. The purpose of the present study was to explore the GSSG_Pt efficacy on the cyclophosphamide-induced cytopenia (myelopenia) model.

The study was conducted on the white male rats weighing 160.0 gr. Cyclophosphamide was introduced once subcutaneously at the back in doses 50 mg/kg (a vehicle was water for injections).

Four groups of animals (with no less than 15 mice in each) were formed. Group description is represented below.

Control Groups:
1—intact animals receiving a single injection of normal saline (NS) instead of CP injection, which further were treated with test article vehicle (normal saline);
2—animals receiving a single CP injection, which further were treated with test article vehicle (normal saline).

Test Group:
3—animals receiving a single CP injection, which further were treated with GSSG.Pt (dissolved in normal saline) in a dose of 5 mg/kg.

On day 2 after the CP injection the intraperitoneal injections of the test or reference articles were started (once a day, during 10-15 days).

At the end of each series (10 and 15 days) the experimental groups were euthanized through ether overdose and peripheral blood (tail veins) and bone marrow (femora) were taken for the analysis. The hematological studies were conducted with the unitized standard methods. The peripheral blood analysis results are represented in the Table 11; myelogram analysis results are given in the Table 12.

Analyzing Table 11 results one can note that cyclophosphamide in the dose 50 mg/kg was found to perform the marked cytopenic effect at all of the formed blood elements with absolute and relative lymphopenia depending on the observation terms (maximally exhibited at the day 15).

It should be noted that four animals died: on the $9^{th}$, $10^{th}$, $12^{th}$, and $14^{th}$ days. In fact, all these animals demonstrated flabbiness, hypodynamia, weight loss.

The GSSG.Pt introduction provided the significant stimulating effect. The general state improvement, positive weight changes were observed, and the immature cell form appearing in blood indicated the bone-marrow hemopoiesis activation. The death of the animals was not noted.

Analysis of the myelogram revealed that cyclophosphamide in the dose 50 mg/kg was found to perform the significant myelotoxic effect. Erythro-, trombocyto- and lymphopoiesis are especially suppressed. Myelosuppression is the most marked at the $15^{th}$ day.

The GSSG.Pt administration had the considerable myelostimulating effect.

The drug GSSG.Pt in the dose 15 mg/kg being introduced as the daily course during 10-15 days exerts the marked myelostimulating effect at the cyclophosphamide-induced cyto- and myelopenia. The drug administration improves the general state, it positively influences at the body weight changes and lowers mortality by about 30%.

Example 7

Effect of GSSG and (Lie GSSG.Pt) on Cytokine and Hemopoietic Factor Production as Well as on Hemopoiesis and Immunity Parameters in Radiation-induced Hemo- and Immunodepression Both oxidized (GSSG) and the structural analog thereof, which is the lithium salt of the hexapeptide with the stabilized disulfide bond (Li.GSSG.Pt), were evaluated in a murine model of hemo- and immunodepression induced by a single irradiation in a total dose of 1 Gy.

The study was designed to evaluate efficacy of seven-day daily administration of the test articles (with the dosing started two hours post-exposure) on the capability of the splenocytes from mice exposed to radiation to produce interleukin-1 (IL-1 α,b); interleukin-2 (IL-2); interleukin-3 (IL-3); interleukin-4 (IL-4); interleukin-6 (IL-6), interleukin-8 (IL-8); interleukin-10 (IL-10); interleukin-12 (IL-12); tumor necrosis factor-α, g (TNF-α, g), interferon-α, g (IFN-α,) and G-CSF, M-CSF, GM-CSF in vitro. In addition, the blood leukocyte and lymphocyte counts and the spleen and bone marrow cellularity (karyocyte count), as we well as splenic and medullary colony-stimulating capacity, were determined at the $8^{th}$ day post-exposure.

Male CBA mice (18 to 20 g body weight) were irradiated with single dose of 180 kV X-rays filtered with 0.5 mm Cu (at 15 mA, distance—70 cm, duration two min. and 28 sec.). The total absorbed dose comprised approximately 1 Gy.

Four groups of animals (with no less than 12 mice in each) were formed. Group description is represented below.

Control Groups:
1—intact animals receiving a sham irradiation procedure to reproduce a stress impact, which further were treated with the test article vehicle (normal saline);
2—control animals irradiated in a dose of 1 Gy, which further were treated with test article vehicle (normal saline).

Test Groups:
3—animals irradiated in a dose of 1 Gy, which further were treated with the test article (GSSG dissolved in normal saline) in a dose of 5 mg/kg;
4—animals irradiated in a dose of 1 Gy, which further were treated with the test article (Li.GSSG.Pt dissolved in normal saline) in a dose of 5 mg/kg.

Two hours after the irradiation the intraperitoneal injections of the test or reference articles were started (as it has been described above). Injections were performed during seven days: once a day, daily.

Twenty-four hours after the completion of seven-day treatment course (on the $8^{th}$ day after the irradiation), mice were euthanized and splenocyte cultures were aseptically prepared for assessment of spontaneous cytokine and hemopoietic factor production (interleukin-1 (IL-1 α,b); interleukin-2 (IL-2); interleukin-3 (IL-3); interleukin-4 (IL-4); interleukin-6 (IL-6), interleukin-8 (IL-8); interleukin-10 (IL-10); interleukin-12 (IL-12); tumor necrosis factor-α, g (TNF-α, g), interferon-α, g (IFN-α, g) and G-CSF, M-CSF, GM-CSF) by the spleen lymphocytes in vitro.

Simultaneously, blood, spleen and marrow samples were collected for blood leukocyte and lymphocyte, and spleen and marrow nucleated cell counting.

Additionally, hemopoietic colony-formation ability of spleen and bone marrow cells was assessed by the method of colony-forming unit (CFU) direct count in the spleens of irradiated singenic CBA mice receiving intravenously spleen or bone marrow cells obtained from animals of control or test groups.

Splenocytic levels for the cytokine and hemopoietic factor production, blood, bone marrow, and spleen cellular indices as well as the colony-forming parameters (colony-forming units, CFU) at the bone marrow and spleen of the irradiated animals at the $8^{th}$ day post-exposure, are summarized in Table 13.

As is evident from the table data, the Li.GSSG.Pt administration results in statistically significant recovery of the cytokine and hemopoietic factor production by splenocytes, whereas GSSG produces less significant effect. However, Li.GSSG.Pt influences endogenous production for the wider cytokine and hemopoietic factor range as well as regulates the cytokine status alterations with respect of the corresponding pathologic process.

Thus, the Li.GSSG.Pt usage as an applied method in animals with developed radiation-induced hemo- and immunodepression results in pronounced stimulation-regulation of the endogenous cytokine and hemopoietic factor production, and also leads to an effective recovery for the cellular compositions of the blood, lymphoid and hemopoietic organs as well as the bone marrow and spleen colony-forming activity.

Example 8

Effect of the GSSG.Pt Composite and Salts thereof on Processes of Phosphate Modification as Well as on Content of Lymphocytes Bearing IL-2 Receptors The molecular mechanisms of the reproduction of the immuno-biochemical effects of the cytokines with the GSSG.Pt composite and the salts thereof were studied.

At the study action of the GSSG.Pt composite and the salts thereof—sodium (Na), lithium (Li) and magnesium (Mg)—was evaluated at the murine model of hemo- and immunodepression induced by single administration of cytostatic cyclophosphamide (CF).

At this study the effect of a five-day long administration of the test articles on the capability of the phosphorylating level of the lymphocyte cytosol proteins on tyrosine and content of the "active" lymphocytes-carriers of IL-2-receptors were evaluated.

Male CBA mice (18 to 20 g body weight) were given a single intraperitoneal injection of CP in a dose of 50 mg/kg. After the CF injection the animals were introduced with the tested articles in dose of 5 mg/kg 24 hours later. The tested articles were introduced during five days (daily, once a day). Twenty-four hours after completion of the tested article introduction the mice were euthanized and blood samples were collected to conduct the study.

A fraction of mononuclear leukocyte was obtained by centrifugation in gradient of ficoll-metrizoat (Histopaque, Sigma). Cell concentration was adjusted to $2 \times 10^6$ cells per 1 ml of cell culture medium (RPMI 1640), containing 20 mM HEPES, 2 mM glutamine, 50 mg/mL gentamicin and 10% fetal calf. Cell viability was estimated by the Trypan blue exclusion method, then the cell suspension was placed into wells of 96-well microliter plates—200,000 cells per well.

Content of the lymphocytes-carriers of the IL-2-receptors was determined according to Horgan A. F. (1994) on smears of mononuclear slip. Mononuclear antibodies to chains p55 and p75 of the IL-2-receptor were used as the first antibodies. To reveal the first antibodies the polyclonal rabbit antibodies against murine immunoglobulins marked with were used. Count of the lymphocytes-carriers of the IL-2-receptors was made in percentage to the number of total lymphocytes.

For metabolical marking lymphocytes were cultivated in the Igla medium with addition of 10% cattle serum. The metabolical marking with [32P]ortho-phosphoric acid was performed by cell incubation during 10-12 hrs. in the phosphorusless medium DME containing 100 μCi/ml of [32P]ortho-phosphate. On each sample 0.2 ml of the medium with isotope were added. After incubation cells were destroyed by pipetting and centrifuged at 6000 g for 30 min. The obtained supernatant was used for immunoprecipitation with polyclonal antibodies to phosphotyrosine at Fu method (1992). Protein A-sefarose was used for the precipitation of immune complex. The precipitate was washed three times and the precipitate activity was counted on "Gamma" counter.

According to the results of the conducted study (Table 14), it was found that action of the GSSG.Pt composite on the isolated lymphocytes causes (see Table 14) at 10 minute a significant increase of the phosphorylating level on tyrosine of the lymphocyte cytosol proteins, which is the integral indication of the activity of the signal-transducing systems. These changes due to the GSSG.Pt composite action, largely due to the GSSG.Pt composite derivative action determine the modulation of the redox-sensitive gene expression, first of all, immunologically important genes, responsible for the synthesis of the cytokines and hemopoietic factors.

In Table 15 the data is given on phosphorylating level on tyrosine of the lymphocyte cytosol proteins and percentage of the lymphocytes-carriers of IL-2-receptors in CBA-line mice received the tested articles having cyclophosphamide induced hemo- and immunodepression.

Application of the GSSG.Pt composite salts results in the increase of the percentage of the lymphocytes-carriers of IL-2-receptors and almost normalizing their quantity (normal one is 18.3±1.6%). The similar regularity was found when phosphorylating level on tyrosine of the lymphocyte cytosol proteins was studied.

Application of the GSSG.Pt composite salts results in restoration of the percentage of the lymphocytes-carriers of IL-2-receptors in immunodeficiency conditions modeled by cyclophosphamide. There is the increase of the phosphorylating level on tyrosine of the lymphocyte cytosol proteins of the signal-transducing systems that can be one of the factors of the described immunostimulating actions of the articles tested.

Thus, the example provides evidence of GSSG.Pt to reproduce (imitate) the regulatory effects of the range of cytokines, first of all, IL-2. We are intending to mean the induction by the GSSG.Pt composite of the intracellular mechanisms performing regulatory cytokine signals on the system of immunocompetent and hemopoietic cells as the IL-2 effect reproduction. The conducted studies have shown that changing of the phosphorylating level on tyrosine of the lymphocyte cytosol proteins of the signal-transducing systems of the cells of the organs immunogenesis and hemopoiesis in conditions of cyclophosphamide modeled immunodeficiency causes the effect of the dynamic normalization of the active lymphocyte content.

Therefore, application of the GSSG.Pt composite and derivatives thereof in the form of therapeutically purposed medicinal drugs not only stimulates the cytokine and hemopoietic factor endogenous production but also provides the reproduction of the immune-biochemical cytokine effects, especially in case of receptors desensitization observed mainly in oncological and retro-virus pathology.

Example 9

Stimulation of Endogenous Cytokine Production and the Therapeutic Effect of the GSSG.Pt Application in a Patient with a Stomach Cancer, Peritoneal Metastases, Ascites, Splenomegaly and Cholestatic Hepatitis A 33-year old patient was diagnosed as having stomach neoplasm for more than two years (adenocarcinoma of moderate differentiation degree). In 1993 the patient was operated for malignant stomach ulcer and numerous dense lymph nodes were found in the Porte hepatis which were considered to be metastases.

In January 1994 the course of chemotherapy (5-FU) was complicated by the severe cholestasis and percutaneous drainage of the left and right liver ducts was undertaken, that six months later was followed by the choledochoejunostomy with changeable transliver drains with Brown's anastomosis.

In November 1995 the patient's state worsened. According to the examinations the patient experienced an active secondary hepatitis. The liver was enlarged and painful and protruded from the costal arch up to 5-6 cm. Blood chemistry indices proved to be persistently abnormal and hardly corrected by the performed treatment: bilirubin—40.0 due to indirect (up to 31.0); activity of amino-transferases—approximately six times higher than upper normal limit, hypoalbunemia was up to 26%; and there was also hypergammaglobulinemia; hypercholesterolemia was up to 10.2 mmol/l.

During fibrogastrocopy (November, 1995) a stomach cancer located in the middle area of the stomach body and extended about 8 cm was confirmed. The tumor was solid-like type. Stomach walls were rigid. Histology examination defined the tumor as adenocarcinoma of moderate degree differentiation. In December, 1995, the patient had an explorative laparotomy. Ascites was found with plural metastases all over the peritoneum, splenomegaly. The patient's case was identified as inoperable.

A decision was taken to apply GSSG drug form. The drug was injected parenterally (intramuscularly and intravenously), and additionally, the drug form was used via local injections around the tumor tissue through an endoscope. An average doses which were used for intramuscular and intravenous injections—0.1-0.5 mg/kg, and for local injections—up to 50 mg in situ. Parenteral injections of the drug were applied every other day, b.i.d. (intravenous injections at the morning, and intramuscular ones at the evening), during three weeks, and after that, two times a week during four weeks. The drug introduction through the endoscope was performed once in seven days. Two months after the beginning of the treatment with the drug form used the fibrogastroduodenoscopy showed: esophagus was passable, mucous membrane was pink, cardia rosette was partly closed. On empty stomach moderate amount of foamy secretion was in the stomach, which was intensively colored with bile. The tumor extent was 4.8 cm. At the same time, substantial improvement of hematology and blood chemistry indices was found and the liver size decreased up to 3 cm (below the costal arch).

Six months after the treatment completion (July, 1996) the patient's state worsened significantly. According to the examination the secondary hepatitis relapsed. The liver was increased in size and tender, protruded 4 cm beyond the costal arch. Blood chemistry indices were abnormal and hardly corrected by the performed treatment: bilirubin—360 due to indirect (up to 28.0); activity of amino-transferases—approximately four times higher than upper normal limit, hypoalbunemia was up to 21%; and there was also hypergammaglobulinemia; hypercholesterolemia was up to 9.42 mmol/l.

At the fibrogastrocopy (July, 1996) a stomach cancer located in the middle area of the stomach body and extended about 6 cm was confirmed. The tumor was solid-like type. Stomach walls were rigid. Histology examination defined the tumor as a moderate degree differentiation adenocarcinoma. In August, 1996, the patient had an explorative laparotomy. Ascites was found with plural metastases all over the peritoneum, splenomegaly. Considering the previously conducted therapy the decision was taken to apply the new drug GSSG.Pt that is the structural analog of the former administered GSSG drug. The drug was introduced according to the identical regime: parenterally (intramuscularly and intravenously), and additionally, the drug form was introduced via local injections around the tumor tissue through an endoscope. An average doses which were used for intramuscular and intravenous injections—0.1-0.5 mg/kg, and for local injections—up to 50 mg in situ. Parenteral injections of the drug were applied every other day, b.i.d. (intravenous injections at the morning, and intramuscular ones at the evening), during three weeks, and after that, two times in a week during four weeks. The drug introduction through the endoscope was performed once in seven days.

Two months after the treatment initiation with the applied drug: the liver protruded 1 cm beyond the costal arch, tenderless at palpation. According to the ultrasound examination data: there is fibrous tissue at the place of previously determined cancer sites. At the fibrogastrocopy: the esophagus was passable, mucous membrane was pink, cardia rosette was partly closed. The gastric walls are elastic. There was moderate amount of foamy secretion in the stomach with saliva in empty stomach. The tumor extent was 1.5 cm. The duodenum was freely passable. At the same time, substantial improvement of hematology and blood chemistry indices was indicated.

Comparing the therapeutical efficacy of the drugs GSSG.Pt and GSSG using of the former one was found to be advantageous that was manifested by the positive changes at the clinical, biochemical, hematological and immunological indices, fibrogastrocopy data (the tumor size decrease at 75% while applying GSSG.Pt comparing to the 40% decrease after the GSSG administration) (Tables 16, 17). Moreover, at the Table 17 one can see that GSSG.Pt stimulates production of the wider cytokine and hemopoietic factor range having a regulatory influence on their content change.

Thus, the treatment according to the present invention resulted in considerable regress of tumor process with simultaneous obvious beneficial changes in hematology, blood chemistry and immunology parameters, and significant improvement of the life quality.

Example 10

Therapeutical Efficacy the GSSG.Pt Application for Treatment of Lung Cancer

No. 1

Year of birth: 1938.

Diagnosis: Cancer of the right lung upper lobe.

Histological diagnosis: No. 45760 (State Research Center on Pulmonology)—small cell cancer.

Case-history: No. 4024.

Complaints on admission: coughing with hard discharged mucous sputum, dyspnea on little exertion.

Objective examination: The patient's state is satisfactory. Peripheral lymph nodes are not enlarged. There are coarse breath sounds weakened at the upper and medium regions of the right lung. There are rare dry rales, dyspnea on the slightest exertion.

Roentgenography (initial data): The upper mediastinum shadow is broadened due to enlarged right paratracheal lymph nodes. The indistinct shadow of the upper right root part is broadened. There is an additional shadow in the peripheral $S_3$ region of the right lung against the background of marked interstitial changes in both lungs. The right interlobar borders are thickened. Conclusion: there are signs of metastases into lymph nodes of the root and the mediastinum with lymphangoitis sings.

Treatment course: there were applied three immunochemotherapy courses using GSSG.Pt drug.

After the treatment: the patient's state has improved significantly: the mild weakness is still present, there is no dyspnea.

Objective examination: The state is satisfactory. The peripheral lymph nodes are not enlarged. There is a weakened breath sounds in the medium departments of the right lung. The breath sounds in other departments are vesicular. There are no rales.

Roentgenography (after the treatment performed): The lung fields are particularly clear. There are mild infiltrative signs at the $S_3$ department of the right lung. The roots are not enlarged. There are no additional formations at the right root projections. The upper mediastinum shadow is not enlarged. The solitary paratracheal lymph nodes can be determined.

No. 2

Year of birth: 1945.

Diagnosis: Right lung cancer, hepatic metastases.

Histologic diagnosis: No. 45998, small cell cancer

Case-history: No. 4076

Complaints on admission: coughing with hard discharged mucous sputum, dyspnea on mild exertion, weakness, constant pains in the lumbar region extending to stomach. During last six months the patient lost 6 kg.

Objective examination: The state is medium severe. Scleras are icteric. The breathing sounds are coarse, weakened in the right lung upper and medium departments. In the right supraclavicular zone one can palpate enlarged lymph nodes (solid consistency, hardly movable, size—3.0 and 1.0 cm, painless). At auscultation there are coarse breathing sounds, weakened in the medium departments in the right. There are solitary dry rales, dyspnea on the slightest exertion. The liver protruded 3.5 cm over the costal arch.

At examination there were found: middle-lobe bronchus cancer, middle lobe hypoventilation, pneumonitis. At ultrasound examination there are sings of metastatic liver impairment.

Roentgenography (initial data): The right lung middle lobe is decreased in size (state of hypoventilation). Against the background of the increased lung pattern there is intensive, almost homogenous infiltration with distinct margin along the horizontal interlobar pleura. The right root cannot be determined. The upper and lower lobes of the right lung and the left lung are without any particular features. The mediastinal organs are not noticeably displaced.

Treatment course: there were applied three immunochemotherapy courses using GSSG.Pt drug.

After the treatment: The patient's state has improved significantly: there are no weakness and dyspnea, appetite has appeared, he gained 5 kg. The blood indices have restored.

Objective examination: The state is satisfactory. The peripheral lymph nodes are not enlarged. There is a weakened breath sounds in the medium departments of the right lung. The breath sounds in other departments are vesicular. There are no rales.

According to the liver ultrasonography and CAT scan data: there is full mass process regression.

Roentgenography (after the treatment performed): There is the insignificant atelectasis of the middle lobe at the thoracic X-rays picture. The roots are structural and not enlarged, the right one is slightly displaced downward. The heart is not enlarged in size.

Comparing to the initial data there is considerable positive development: at the right the pulmonary tissue has become more transparent (reduction of the hypoventilation signs), there are no infiltrative shadows.

Conclusion:

Evaluating therapeutical effectiveness of the GSSG.Pt drug the following was found:

1. Clinical restoration of indices (general state improvement, pathologic absence of symptoms, body weight gaining);

2. Roentgenologic picture changes (pulmonary tissue transparency increase, infiltrative absence of shadows, disappearing of atelectasis and hypoventilation);

3. Hematologic restoration of indices(increase of the erythrocyte count and hemoglobin content, restoration of white blood count);

4. Changes of the ultrasound and CAT scan data (full tumor process regression);

5. Immune indices restoration and increase of the $CD16^+$, $CD25^+$ counts indicating restitution of the antitumor surveillance system.

6. Induction of the wide cytokine range synthesis as well as modulation of their content mutual regulation (correlation of the content changes of IL-1b, IL-4, TNF-$\alpha$).

Thus, in the given clinical Examples it has been demonstrated that the GSSG.Pt drug application has provided faster restoration of clinical, roentgenologic, hematologic and immune indices ensuring more effective restitution of the immunity and hemopoiesis systems. The aforementioned indicates the tumor process regression that, eventually, calls out significant increase of the patient's quality of life.

Example 11

Therapeutical Efficacy the GSSG.Pt Application for Treatment of Chronic Viral Hepatitis B (CHBV)

No. 3

Date of birth: 1945

Diagnosis: CHBV, replicative phase (PCR HBV+) with moderate activity grade.

Case-history: No. 1068.

Complaints at admission: weakness, discomfort under the right costal arch, nausea, no appetite.

Anamnesis morbi: during last six years the patient noted periodically appeared dull pains under the right costal arch, weakness, urine color changes. At examination there was found: hyperbilirubinemia up to 34 mmol/L, ALT increase to 5.4 mmol/hr.L. CHBV serologic markers and PCR HBV(+) were determined at the hospital examination.

Objective examination: The patient's state is satisfactory. The liver protruded 2 cm beyond the costal arch. The liver margin is firm and tender.

Previous treatment was not performed.

Treatment course: There was performed the treatment course with administration of the GSSG drugs according to the regime.

State after the performed treatment course: There were noted the following positive changes—significant general state improvement, no weakness and nausea, diminution of the discomfort sensation. The liver protruded 0.5 cm beyond the costal arch. The liver margin is soft and tenderless.

No. 4

Year of birth: 1964

Diagnosis: CHBV, replicative phase (PCR HBV+), moderate activity degree.

Case-history: No. 1043.

Complaints on admission: considerable weakness, no appetite, sweating, urine darkening.

Anamnesis morbi: The patient feels sick beginning from January 1996 when for the first time there appeared dull pains under the right costal arch, temperature increase up to 38.7° C., vomiting, urine darkening. Acute viral hepatitis B was diagnosed and confirmed serologically. The patient was administered with detoxicating and antibacterial therapy. However, afterwards there were observed increased Hbs Ag and ALT values, persistent viral replicative activity. Being examined at the last time there were found: hyperbilirubinemia to 78 mmol/L, ALT increase to 6.2 mmol/hr.L. CHBV serological markers and PCR HBV(+) were determined at the hospital examination.

Objective examination: The general state is satisfactory. Skin and scleras are icteric. The liver protruded 2.5 cm beyond the costal arch. The liver margin is firm and tender.

Previous treatment: from 17 Sep. 1997 the patient was administered with acyclovir during 21 days. After the course completion there were increased ALT—up to 2.1 mmol/hr.L, bilirubin to 32 mmoVL. The Hbs Ag degree did not change. The patient's state was defined by the significant asthenic-vegetative syndrome.

Treatment course: There was performed the treatment course with administration of the GSSG.Pt drugs according to the regime.

State after the performed treatment course: There were noted the vivid following positive changes—significant general state improvement, no weakness, sweating and nausea. The skin and scleras were not icteric. The urine color became normal, diminution of the discomfort sensation. The liver protruded 0.5 cm beyond the costal arch. The liver margin became softer and tenderless.

Comparison (Tables 20, 21):

At the comparative analysis on the therapeutical efficacy of the GSSG.Pt and GSSG drugs the former was shown to be advantageous that was manifested by the following:

1. Biochemical indices normalization (ALT and bilirubin decrease);
2. Significant HBs Ag decrease and replication termination;
3. Immune indices normalization and increase of the CD95+ content indicating the apoptosis process activation in the virus-transformed cells;
4. Considerable regulation for the wider cytokine range.

Example 12

Therapeutical Efficacy the GSSG.Pt Application for Treatment of Acute Viral Hepatitis B (AHBV)

No. 5
Sex: female.
Age: 20.
In-patient card: 678
Diagnosis: Acute viral hepatitis B (HBs Ag "+"), replicative phase (PCR HBV "+"), prolonged form; chronic viral hepatitis D, replicative phase (PCR HDV "+").

Complaints during examination: weakness, appetite decrease.

Anamnesis morbi: The patient felt sick in August 1997, when she noticed sharp weakness, malaise, back bone aching, temperature raising up to 38.8° C. Dark urine and sclera icterus appeared 10 days later. The patient was admitted to the viral infectious clinic, where she received course of the detoxicating, spasmolytic, antibacterial therapy. However, replicative viral activity and increased GPT level were still present. The prolonged cytolytic syndrome gave foundation for administration of the drug GSSG.Pt.

Previous treatment was not performed.

Treatment with GSSG.Pt drugs: from 30 Oct. 1997 to 23 Nov. 1997.

Patient's state after the treatment course completion:

The patient's state is satisfactory. She noted the appetite increase, weakness reduction.

Conclusion (Tables 22-24):

The immunomodulating course with the GSSG_Pt drugs has provided the following positive changes: biochemical indices normalization; termination of HBV and HDV replication; termination of HBs Ag persistency; virus-infected cell apoptosis induction; general state improvement; stable therapeutic effect.

Example 13

Therapeutical Efficacy the GSSG.Pt Application for Treatment of Chronic Viral Hepatitis C (CHCV)

No. 6
Sex: male.
Age: 18.
Patient's case: No. 1043
Diagnosis: Chronic viral hepatitis C, replicative phase (PCR HCV "+"), moderately manifested activity; chronic viral hepatitis B, integrative phase (PCR HBV "−"); narcotic intoxication, narcomania.

Complaints during examination: weakness, pains at the right under the ribs, at knee-joints, the backbone and wrist joints.

Anamnesis morbi: The patient noticed pains in the knee-joints and the backbone at the beginning of August, 1997. On blood test an increase of the bilirubin level up to 34 mmol/L and GPT level up to 2.1 mmol/hr.L. were found. During examination in the hospital from Aug. 15, 1997, anti-HCV IgG and the replicative activity of the hepatitis C virus were found.

Anamnesis vitae: The patient started using drugs at 14. To the examination time he uses up to 2 g of heroin per day. He is at the state of the narcotic abstinence.

Previous treatment was not conducted.

Immunomodulating therapy course with GSSG.Pt drugs: from Aug. 15, 1997, to Sep. 7, 1997.

Patient's state after the treatment course completion: The patient's state is satisfactory. He noticed significant reduction of weakness, no pains in the right under the ribs and in the joints. As patient said the narcotic abstinence state diminished almost without pain and in less time. Biochemical indices normalization and absence of the viral replicative activity was marked.

Conclusion: The immunomodulating therapy course with the GSSG.Pt drug provided positive changes, which were indicated by: biochemical and serologic indices normalization; termination of HCV replication. Immune indices and cytokine status parameters correlate to the infectious process controlling and viral replication absence. Examination of the patient's peripheral blood lymphocytes by liquid chromatography with monoclonal antibodies to FasAg (CD95$^+$) after the treatment revealed the CD95$^+$ cell increase indicating activation of the programmed cell death process in virus-infected cells. At supervision at one and three months after the treatment stabilization of this state was noted.

Concomitant drug intoxication and an abstinence state at application of the GSSG.Pt drugs were corrected faster and were less excruciating for the patient.

The immunomodulating course with the GSSG.Pt drugs for chronic hepatitis C with replicative activity and concomitant drug intoxication has provided the following results:
- biochemical indices normalization in blood;
- hematological indices normalization;
- termination of HCV replication;
- normalization of the immune blood indices and cytokine status;
- apoptosis process induction in the peripheral blood lymphocytes;
- rapid correction for the drug abstinence state;
- stable therapeutic effect Example 14

Comparative Analysis of the GSSG and GSSG.Pt Effects on Growth Development and Apoptotic DNA Degradation at Normal and Transformed Cells The GSSG and GSSG.Pt effects on growth development and apoptotic DNA degradation at normal and transformed (HL-60) cells were comparatively analyzed. To that end, GSSG and GSSG.Pt were incubated for 24 hours with HL-60 myeloid line cells and normal human lymphocytes obtained from healthy volunteers' blood.

Venous blood of healthy volunteers was collected into heparinized test-tubes, which had been tested for endotoxin. A mononuclear fraction of blood leukocytes was obtained by centrifugation in ficoll-metrizoat gradient (Histopaque, Sigma). Cell concentration was adjusted to $2 \times 10^6$ cells per 1 ml of cell culture medium (RPMI 1640), containing 20 mM HEPES, 2 mM glutamine, 50 mg/mL gentamicin and 10% fetal calf serum. Cell viability was estimated by the Trypan blue exclusion method, then the cell suspension was placed into wells of 24- and 96-well microliter plates—250,000 cells per well.

The HL-60 myeloid line cells were grown in RPMI-1640 medium with addition of 10% fetal calf serum. Cultivation was carried out in closed flasks, the medium volume was 12 mL, it was replaced every four days. Directly before testing the cell suspension in the fresh medium was brought into 24-well microliter plates (cell concentration for each well was 250,000 cells per well) and the tested articles—GSSG and GSSG.Pt—were added into the corresponding wells up to final concentration 100 mg/mL.

The effect testing for the testing articles was performed 24, 48 hours after addition into the culture.

The analysis procedure involved the following: after 24-48 hour incubation there were calculated the total cell count and the dead cell count by the Trypan blue exclusion method; afterwards the cell suspension was centrifuged (at 12.000 g, in Eppendorf test-tubes during 10 min). The cell pellet was frozen and kept at −70° C. before the DNA separation. The DNA separation was conducted by Kirbi-Georgiyev phenol method. To the cell pellet there were added 0.5 ml of 10% SDS and 0.5 ml of TE-buffer containing 0.1M EDTA and 0.01 M Tris-HCl with pH 8.0 ("A" buffer), and the pellet was resuspended by the tube shaking during 15 min. Then the equal phenol amount was added adjusted by 0.01 M Tris-HCl with pH 8.0, the product was mixed during two min. and centrifuged in the Eppendorf test-tubes at 12.000 g during 15 min. After the centrifugation completion the upper water phase was phenol-treated one more time. After the phenol treatment the upper water phase was twice treated with phenol-chloroform mixture (1:1) that was mixed with the water phase in equal amount. The water phase was separated by centrifugation at 12.000 g during 10 min., pumped out and once mixed with the equal chloroform amount. Afterwards it was centrifuged at 12.000 g, the upper phase was separated, mixed with double amount of distilled ethyl alcohol frozen to −20° C. and kept for one night at −20° C. The DNA pellet was gathered by centrifugation at 12.000 g during 10 min., the supernatant was removed and the pellet was washed by 200 mL of 70% ethyl alcohol frozen to −20° C. during five min., centrifuged one more time at the same conditions and afterwards the pellet was air-dried during one hour. Then it was diluted in 10 mL of the A buffer; the DNA amount was determined by Dishe method and electrophoresis was performed in 2% agarose gel (agarose with NA grade made by "Pharmacia LKB, Biotechnology Inc" (Austria) was used). The DNA electrophoretic separation was made in a block of 2% agarose gel in a device made by "Pharmacia LKB, Biotechnology Inc" (Austria). As a buffer solution 0.04 M tris-HCl buffer, pH 7, containing 0.02 M of sodium acetate and 0.02 M EDTA was applied. Agarose (2%) was prepared at an electrode buffer. The DNA samples (2-5 mg) were placed into the gel slots. The electrophoresis was conducted with an electrical field intensity of 6 W/cm during three hours. The sample propulsion was observed due to bromine-phenol blue motion. On the electrophoresis completion the gel block was taken out of the device and introduced into a tray with etidium bromide solution (3 mg/mL H2O) for 30 minutes in dark place. After the incubation completion the gel was rinsed with water and examined in the transmitted ultraviolet radiation with the wave-length 254 nm at a transilluminator made by "Pharmacia LKB, Biotechnology Inc" (Austria). The gel was photographed by Zenit E camera with a red colour filter.

Figure 13:
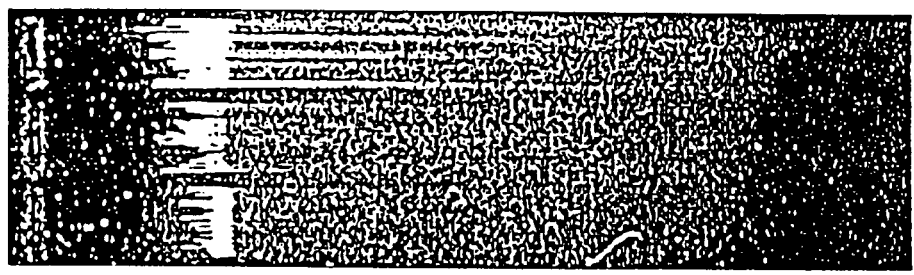
FIG. 13 shows the DNA degradation character of the normal cells at the control group (1), after treatment with: GSSG (2), GSSG.Pt (3) incubation time—48 hrs.
Figure 14:
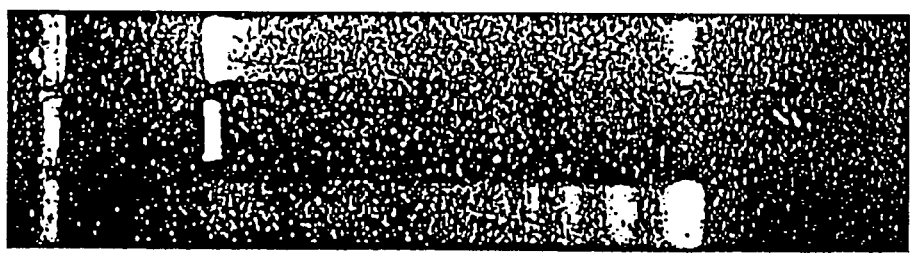
FIG. 14 shows the DNA degradation character of the HL-60 cells at the control group (2), after treatment with: GSSG (1), GSSG.Pt (3) incubation time—48 hrs.

The study results are given in the Tables 28 and 29 and FIGS. 13 and 14. As one can see in the Tables 28 and 29 data, the GSSG and GSSG.Pt influence on normal and transformed cells is of an alternative character. GSSG and GSSG.Pt stimulated the normal cell proliferation (Table 28). The electrophoresis of DNA obtained from the normal cells (Table 28) revealed presence of only traceable quantities for apoptotic fragments at the background of homogenous high-molecular fraction hcaracteristic for the viable cells.

In the contrary, in the myeloid origin (HL-60) cancer cell culture, the apoptosis activation and the cell division inhibition were observed due to the influence of both drugs (Table 29, FIG. 14). The diversities of the effects were of the quantitative nature.

Thus, the dead HL-60 cell quantity after the GSSG impact was reliably lower than the one after the GSSG.Pt effect (Table 29). An evident indication for stronger impact efficacy (GSSG.Pt comparing to GSSG) on the HL-60 cells is the apoptotic fragment's character obtained after the electrophoretic analysis. The DNA electrophoresis of the HL-60 cells non-incubated with the drugs demonstrated presence of highly-molecular, practically homogenous DNA characteristic for the viable cells (FIG. 14, band #2). The DNA electrophoresis of the cells incubated during 24 and 48 hours with the GSSG.Pt and GSSG drugs revealed the DNA oligonucleosomic degradation (FIG. 14, bands 1 and 3, respectively), i.e., an apoptotic ladder, that is indisputable sign for the programmed cell death. However, the apoptotic ladder for the HL-60 cells treated with GSSG contained considerable amount of the high molecular DNA characteristic for the viable HL-60 cells (FIG. 14, band #1), whereas the high molecular DNA for the cells treated with GSSG.Pt was virtually absent (FIG. 14, band #3).

The HL-60 cells are defective in the p53 gene (p53 gene deletion) and apoptosis induction through the GSSG and GSSG.Pt treatment can occur only without involving the p53 product. Therefore, one can state that the GSSG and GSSG.Pt drugs activate an inner contour of the programmed cell death irrespectively of the p53 gene product. The p53 defect is present approximately at half of cancer pathology cases. The experimental results appeared to denote efficacy of GSSG and, especially, GSSG.Pt for these tumor chemotherapy.

Conclusion: The performed studies allowed to obtain data indicating capacity of the GSSG and GSSG.Pt drugs to increase normal cell (lymphocytes) viability and, contrariwise, to induce apoptosis in ransformed cells, i.e., exercise an antitumor activity. Besides, the GSSG.Pt activity regarding to the transformed cell apoptosis induction excelled significantly the one for the GSSG drug according to the objective viability criterion, i.e., presence of the high molecular DNA that appeared considerably after the GSSG treatment and was almost absent after the GSSG.Pt treatment. Thus, the data obtained on cells of the myeloid line HL-60 defective in the p53 gene that is the crucial agent in apoptosis induction allows us to state that:

The GSSG and GSSG.Pt drugs induce the inner contour of the apoptosis development regardless of the p53 gene product;

The GSSG.Pt drug based on composite possesses higher chemotherapeutic activity (due to the apoptotic induction in the transformed cells) versus the first generation drug GSSG.

Example 15

Analysis of the GSSG.Pt Effects on Growth Development and Apoptotic DNA Degradation at Normal and Transformed Cells Defective in the p53 Antioncogene with Increased Ras-gene Expression The GSSG.Pt effects on growth development and apoptotic DNA degradation of different lineage of transformed cells (HL-60, C-8, A-4) were comparatively analyzed depending on the p53 defect that is the key factor for the apoptosis development and the ras-gene that is a multipotent factor for cell reaction. The HL-60 cell culture is human cells of myeloluekosis origin defective in the p53 gene. Cell cultures C-8 and A-4 are transformed murine fibroblasts having a plasmid with the ras gene and a gene of the E1a expression enhancement factor that is an adenovirus antigen fragment. At that, the A-4 cells are defective at the p53 gene and the C-8 ones contained the intact p53 gene. A donor blood lymphocyte slip was used as a control of the human cells with the intact p53 gene.

The HL-60 (p53--) myeloid line cells were grown in RPMI-1640 medium with addition of 10% fetal calf serum. The cell suspension cultivation was carried out in closed flasks, the medium volume was 12 mL, it was changed every four days. Directly before testing the cell suspension in the fresh medium was brought into 24-well microliter plates (cell concentration for each well was 250.000 cells per well) and the tested article—GSSG.Pt—was added into the corresponding wells up to final concentrations 10-100 mg/mL.

Venous blood of healthy volunteers was collected into heparinized test-tubes, which had been tested for endotoxin. A blood leukocyte mononuclear fraction was obtained by centrifugation in ficoll-metrizoat gradient (Histopaque, Sigma). Cell concentration was adjusted to $2\times10^6$ cells per 1 ml of cell culture medium (RPMI 1640), containing 20 mM HEPES, 2 mM glutamine, 50 mg/mL gentamicin and 10% fetal calf serum. Cell viability was estimated by the Trypan blue exclusion method, then the cell suspension was placed into wells of 24- and 96-well microliter plates—250,000 cells per well.

The murine transformed fibroblasts were grown in DMEM medium with addition of 10% fetal calf serum. The cell suspension cultivation was carried out in closed flasks, the medium volume was 12 mL, it was changed every four days. Directly before testing the cell suspension in the fresh medium was brought into 24-well microliter plates (cell concentration for each well was 50.000 cells per well) and the tested article—GSSG.Pt—was added into the corresponding wells up to final concentrations 10-100 mg/mL.

The effects testing for the testing articles was performed 24, 48 hours after introduction into the culture.

The analysis procedure involved the following: after 24-48 hour incubation, the total cell count and the dead cell count were calculated by the Trypan blue exclusion method; afterwards the cell suspension was centrifuged (at 3.000 g, in Eppendorf test-tubes during 10 min). The cell pellet was frozen and kept at $-70°$ C. before the DNA separation. The DNA separation was conducted by Kirbi-Georgiyev phenol method. To the cell pellet there were added 0.5 ml of 10% SDS and 0.5 ml of TE-buffer containing 0.1M EDTA and 0.01 M Tris-HCl with pH 8.0 ("A" buffer), and the pellet was resuspended by the tube shaking during 15 min. Then the equal phenol amount was added adjusted by 0.01 M Tris-HCl with pH 8.0, the product was mixed during two min. and centrifuged in the Eppendorf's test-tubes at 12.000 g during 15 min. After the centrifugation completion the upper water phase was phenol-treated one more time. After the phenol treatment the upper water phase was twice treated with phenol-chloroform mixture (1:1) that was mixed with the water phase in equal amount. The water phase was separated by centrifugation at 12.000 g during 10 min., pumped out and once mixed with the equal chloroform amount. Afterwards it was centrifuged at 12.000 g, the upper phase was separated, mixed with double amount of distilled ethyl alcohol frozen to $-20°$ C. and kept for one night at $-20°$ C. The DNA pellet was gathered by centrifugation at 12.000 g during 10 min., the supernatant was removed and the pellet was washed by 200 mL of 70% ethyl alcohol frozen to $-20°$ C. during five min., centrifuged one more time at the same conditions and afterwards the sediment was air-dried during one hour. Then it was diluted in 10 mL of the A buffer; the DNA amount was determined by Dishe method and electrophoresis was performed in 2% agarose gel (agarose with NA grade made by "Pharmacia LKB, Biotechnology Inc" (Austria) was used). The DNA electrophoretic separation was made in a block of 2% agarose gel in a device made by "Pharmacia LKB, Biotechnology Inc" (Austria). As a buffer solution 0.04 M tris-HCl buffer, pH 7, containing 0.02 M of sodium acetate and 0.02 M EDTA was applied. Agarose (2%) was prepared at an electrode buffer. The DNA samples (2-5 mg) were placed into the gel slots. The electrophoresis was conducted with an electrical field intensity of 6 W/cm during three hours. The sample propulsion was observed due to bromine-phenol blue indicator motion. On the electrophoresis completion the gel block was taken out of the device and introduced into a tray with etidium bromide solution (3 mg/mL H$_2$O) for 30 minutes in dark place. After the incubation completion the gel was rinsed with water and examined in the transmitted ultraviolet radiation with the wave-length 254 nm at a transilluminator made by "Pharmacia LKB, Biotechnology Inc" (Austria). The gel was photographed by Zenit E camera with a red color filter.

The study results are given in the Tables 30, 31, 32, 33. As is evident from the Table 31, GSSG.Pt induces apoptosis in the HL-60 cell culture defective at the p53 gene. The effect was rather developed at the concentration of 10, however, it was more evident at 100 mg/mL. Also there were observed conglomeration of DNA apoptotic fragments multiple of DNA nucleosome size that is the indisputable sign of programmed cell death.

In contrary, GSSG.Pt made stimulating effect on normal cells, i.e., there was certain proliferation observed (Table 30). Electrophoresis of DNA obtained from normal cells exhibited that it was represented by a homogenous high-molecular fraction characteristic for viable cells.

Thus, differences of the drug action on normal and transformed cells were basically divergent. Mechanism for the GSSG.Pt divergent action might be conditioned by activation of the p53-independent apoptotic pathway through the ras-signal-transducing system. The ras-system is capable to stimulate cell proliferation and differentiation through the mitogenic factor cascade and induce apoptosis (programmed cell death) through another cell signal cascade.

To check it there were compared the GSSG.Pt effects on murine fibroblasts with enhanced ras-gene expression but different in the intact p53 gene (wild type) presence—cells C-8 (p53++), or the p53 gene absence (a genetic defect)— (cells A-4 (p53−−)). As one can see from the Tables 32 and 33, the GSSG.Pt effect appeared in both cell lineages. The apoptosis induction was significantly exhibited. It indicates activation of the p53-independent apoptotic pathway. Presence of the activated ras gene in both of the cell lineages can be an explanation for the apoptotic exhibition that was even more marked in the transformed fibroblasts than in the HL-60 cells. It confirmed the apoptosis induction through the ras-signal-transducing system. The GSSG.Pt effect on the A-4 and C-8 cells was not different at concentration of 10 mg/mL. The significantly superior GSSG.Pt effect on the A-4 cells comparing to the C-8 cells was noted at the concentration 100 mg/mL. The p53-protein absence appeared even to enhance the ras-signal-transducing pathway for apoptosis induction in tumor cells.

The p53 gene defect occurs in approximately half of the cancer disease cases. The results of these experiments can imply the GSSG.Pt effectiveness for chemotherapy of these tumors.

Conclusion: The data from these studies indicate the capacity of the GSSG.Pt drug to increase normal cell (lymphocytes) viability and, contrariwise, to induce apoptosis in transformed cells, i.e., exercise an antitumor activity. Besides, the GSSG.Pt activity regarding to the transformed cell (defective at the p53 gene) apoptosis induction even excelled the one for the cells with the intact p53 gene at the high drug concentration. According to the objective viability criterion, i.e., presence of the high molecular DNA that appeared in considerable amounts after the GSSG.Pt treatment of the normal donor cells (take from the lymphocyte slip), the cell death was practically absent whereas in case of the GSSG.Pt impact on transformed cells there was observed the DNA apoptotic degradation, i.e., the sign of the irreversible apoptotic death induction even in the cells defective at the p53 gene (with the stimulation especially). Previously, in the Example 9 there was shown activation of the cytokine range after the GSSG.Pt treatment. Considering that the cytokine action may be determined with the ras-signal-transducing pathway activation the cytokine stimulation can also cause the antitumor effect through an interaction with the ras-protein.

Example 16

Analysis of the GSSG.Pt Effects on Growth Development and Apoptotic DNA Degradation at Murine Transformed Cells Cultures Defective at Antioncogenes The GSSG.Pt effects on growth development and apoptotic DNA degradation of transformed fibroblasts of a cell lineage with activated ras-gene but an intact p21 gene (p21++-C-8 cells) and murine cell lineage with knockout p21 gene (p21−−).

The p21++ lineage cells are murine transformed fibroblasts having a plasmid with the ras gene and a gene of the E1a expression enhancement factor that is an adenovirus antigens fragment but have intact p53 and p21 genes. The p21 (−−) lineage has the intact p53 and ras genes but it is defective at the p21 gene. It allows evaluating the GSSG.Pt impact on the apoptosis induction in conditions of impaired regulation for the cell division G1 phase. The cell cultures were grown in DMEM medium with addition of 10% fetal calf serum. The cell suspension cultivation was carried out in closed flasks, the medium volume was 12 mL, it was changed every four days. Directly before testing, the cell suspension in the fresh medium was brought into 24-well microliter plates (cell concentration for each well was 50.000 cells per well) and the tested article—GSSG.Pt—was added into the corresponding wells up to final concentrations 100 mg/mL.

The effect testing for the testing articles was performed 24, 48 hours after introduction into the culture.

The analysis procedure involved the following: after 24-48 hour incubation, the total cell count and the dead cell count were calculated by the Trypan blue exclusion method; afterwards the cell suspension was centrifuged (at 3.000 g, in Eppendorf test-tubes during 10 min). The cell pellet was frozen and kept at −70° C. before the DNA separation. The DNA separation was conducted by Kirbi-Georgiyev phenol method. The cell lysis was performed by addition of 0.5 ml of 10% SDS. The equal phenol amount was added there adjusted by 0.01 M Tris-HCl with pH 8.0, the product was mixed during two min. and centrifuged in the Eppendorf test-tubes at 13.000 g during 15 min. The phenol deproteinization was repeated twice. Afterwards the water phase was twice treated with phenol-chloroform mixture (1:1) and once with chloroform. Nucleic acids were precipitated by the addition of two volumes of 96% ethyl alcohol at 20° C. overnight. The DNA was gathered by centrifugation at 13.000 g during 30 min., decanted, washed with 70% ethyl alcohol and air-dried. After the drying the precipitate was dissolved in TE buffer. The DNA concentration was determined in the obtained solution (by Dishe method). Fractional content of the nucleic acids was determined by electrophoresis in 2% agarose gel (agarose with NA grade made by "Pharmacia LKB, Biotechnology Inc" (Austria) was used). The DNA electrophoretic separation was made in a block of 2% agarose gel in a device made by "Pharmacia LKB, Biotechnology Inc" (Austria). The electrophoresis was performed in TAE buffer pH 7.4 (0.04 M tris, 0.02 M of sodium acetate, 0.02 M of EDTA) at an electrical field intensity of 6 W/cm during three hours. The sample propulsion was observed due to bromine-phenol blue indicator motion. The electrophoresis results were examined in the transmitted ultraviolet radiation ($\gamma$=254 nm) at a transilluminator made by "Pharmacia LKB, Biotechnology Inc" (Austria) after the gel dying with etidium bromide solution (5 mg/ml).

The study results are given in the Tables 34, 35. As it is evident from the Table 34, GSSG.Pt induces apoptosis in the p21++ cell culture with activated ras-gene manifested by conglomeration of DNA apoptotic fragments multiple of DNA nucleosome size.

In the p21 (--) cells having non-active ras-signal-transducing system but defective at the control of the cell cycle delay in the G1 phase GSSG.Pt induced apoptosis to less extent that in p21++ cells (Tables 34, 35). It might be implicated by the fact that the ras-system is capable of stimulatin cell proliferation and differentiation through the mitogenic factors' cascade and inducing apoptosis (programmed cell death) through another cell signals' cascade. Absence of the p21 gene expression can cause changes in interrelations of specific cascades of the ras-signal-transducing pathway and, thereupon, lessen the apoptotic stimulation by the drug in cases of p21 gene defects.

The p21 gene defect does not often occur in oncological diseases that considering the performed experiments' issues can imply the GSSG.Pt effectiveness for chemotherapy of these tumors except cases with lower effectiveness at tumors with mutations in p21 gene.

Conclusion: The performed studies allowed obtaining data indicating capacity of the GSSG.Pt drug to induce apoptosis actively in transformed cells, i.e., exercise an antitumor activity. The enhanced ras-gene expression facilitates the apoptosis induction in the transformed cells C-8 indicating implementation of the GSSG.Pt antitumor activity through the ras-signal-transducing system. The lesser drug effect in case of p21 gene expression absence can be determined by the redistribution of factors in mitogenic and apoptotic cascades of the ras-signal-transducing pathway.

Nevertheless, presence of the DNA apoptotic degradation, i.e., the sign of the irreversible apoptotic death induction, is found after the GSSG.Pt action even in p21-defective cells.

The aforesaid allows us to state that the GSSG.Pt composite-based drug:

Realizes chemotherapeutic activity regarding the tumor-transformed cells through induction of the ras-dependent apoptotic pathway;

Induces the apoptosis' development in the tumor-transformed cells including p21-defective cells.

Example 17

Therapeutical Effect of the GSSG.Pt Vanadium Salt in Patient with Diabetes Mellitus No. 7
Gender: female
Age: 37
Out-patient card: No. 63
Diagnosis: Diabetes mellitus. Insulin-independent type—type II. Diabetic angiopathy, grade IV.

Anamnesis morbi: Firstly the high blood sugar was revealed in the age of 31. In October 1994, the patient was admitted into the Endocrinologic Department of the Hospital # 16. There were diabetes cases in the patient's hereditary history on the mother's side. The disease developed gradually, the blood glucose level fluctuated from 12.1 to 15.7 mmol/L, glucosuria to 7%.

Previous treatment: At the onset of the disease, the patient was frequently admitted to hospitals; in 1994 during six months she was administered with Insulin-lente S.N.C.-32 IU and peroral hypoglycemic agents of the sulfonylureas group; then Insulin was cancelled and the patient used antidiabetic agents—Bucarban, Diabeton. The blood glucose changed from 10.7 to 15.4 mmol/L, glucosuria 3-7%.

In Janurary 1998 the patient was taken to the hospital and the following treatment regime was administered: Diabeton 0.08 g-2 tab twice a day, Glucobay 0.1×3 times per day.

| The blood glucose content: | |
|---|---|
| 9 | 12.6 mmol/L |
| 12 | 12.0 mmol/L |
| 14 | 15.3 mmol/L |
| 17 | 19.1 mmol/L |
| 6 | 11.5 mmol/L |

Glucosuria—to 3%

Because of the previous treatment inefficacy, it was decided to use the drug of the GGSG.Pt vanadium salt.

Hospital treatment regime for the GGSG.Pt vanadium salt: from 17 Jan. 1998.

During 10 days once a day—intravenous injections of the GSSG.Pt vanadium salt (daily dose—0.01-0.5 mg/kg).

During the following 10 days—intravenous injections of the GSSG.Pt vanadium salt every other day (daily dose—0.01-0.5 mg/kg).

During the following 10 days (the third decade)—intramuscular injections of the GSSG.Pt vanadium salt once a day (daily dose—0.01-0.5 mg/kg).

The GSSG.Pt vanadium salt treatment was performed along with changed treatment regime by Diabeton and Glucobay. Diabeton was administered 0.08 twice a day, Glucobay 0.05×3 times a day.

The blood glucose restored to normal values and did not exceed 8.2-10.6 mmol/L after meals. After the discharge the patient received the GSSG.Pt vanadium salt treatment as an out-patient during one month.

Ambulant treatment regime for the GSSG.Pt vanadium salt:

For one month there were administered intramuscular injections of the GSSG.Pt vanadium salt once a day (daily dose—0.01-0.5 mg/kg).

During two sequential months of treatment with the GSSG.Pt vanadium salt drug there were noted two episodes of the glucose content decrease to 1.5-2.5 mmol/L, thereat the antidiabetic drugs dosages were lowered. After two months of the treatment, Glucobay was cancelled.

Patient's state after the treatment course completion: After four months of the treatment with administration of the GSSG.Pt vanadium salt drug as a support for the basic therapy, the patient's general state improved significantly and was evaluated as satisfactory. Development of hematologic, biochemical, immunologic blood indices is provided in the Tables 36, 37.

Comments to the indices development of glucose, cAMP/cGMP, thiol-disulfide ratio and other analyzed parameters.

The glucose content development is an integrative criterion for the impact effectiveness of the antidiabetic drugs. The combined therapy by the peroral antidiabetic drugs (Diabeton and Glucobay) along with the GSSG.Pt vanadium salt drug called forth the blood glucose normalization, decrease of the Diabeton therapeutic dosage and the Glucobay cancellation. Character of the hematologic, biochemical and immune parameter changes indicated restoration of the metabolism and the systemic reactions in general that does not allow to determine the antidiabetic constituent for the GSSG.Pt vanadium salt drug. The following indices were used—cAMP/cGMP and thiol-disulfide ratio (TDR)—that allowed to characterize basically a molecular mechanism of the GSSG.Pt vanadium salt drug action on cellular reaction complex stabilizing the blood glucose level. In particular, the key intracellular messengers—cAMP and cGMP—determine intensity of the glucose flow into intracellular metabolic processes. At that, cGMP-dependent enzymatic cellular systems determine the cellular glucose intake intensity. In its turn, the cGMP level is determined by the cellular oxidative potential. In particular, oxidants increase the cGMP level, in the contrary, antioxidants perform depressive action on its content. Thus, the intracellular thiol-disulfide ratio (TDR) reflecting the balance of the anti- and pro-oxidants determines value of the intracellular cAMP/cGMP index. Taking into account an organism as a whole we can analyze these indices in blood as integrative internal medium interrelated with the glucose level fluctuations, because the glucose metabolism is an indefeasible constituent for functioning of all cell types at our organism along with thiol-disulfide metabolism and cyclic nucleotide systems.

The results obtained indicated the glucose-lowering influence of the GSSG.Pt vanadium salt drug. Besides, this effect follows the cGMP content increase development (lowering of the cAMP/cGMP index) and the TDR value decrease (increase of the thiol oxidized forms). Considering regulatory possibilities of the thiol oxidized forms and the cGMP in blood glucose regulation, one can state the basic mechanism of the regulatory hypoglycemic effect of the GSSG.Pt vanadium salt drug. Inter alia, the regulatory impact of the GSSG.Pt vanadium salt drug on the cellular redox contour, provides an increase of the oxidant constituent level that, in its turn, redistributes balance in the cyclic nucleotide system in favor of cGMP (guanylat-cyclase induction and inhibition of phosphodiesterase, cGMP synthesis and destruction enzymes, respectively). The cGMP regulatory impact stimulates the glucose transport processes into insulin-dependent tissues calling forth the blood glucose decrease.

Conclusion: Application of the GSSG.Pt vanadium salt drug in the scheme for the combined diabetes treatment allowed to obtain the following therapeutic effects:
the quality of life improvement and the blood glucose level stabilization;
dosage decrease for the administered glucose-lowering drugs;
restoration to normal values of the hematologic, biochemical and immunologic indices.

Those skilled in the art would readily appreciate that all parameters listed herein are meant to be examples and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

The invention claimed is:

1. A composition, comprising:
an oxidized glutathione-based compound formed from two monomers, each monomer comprising a glutamic acid bonded to a cysteine bonded to a glycine, the two monomers being linked through a disulfide bond bridging the sulfur atoms of each respective cysteine of each monomer, the composition comprising a metal material comprising a metal selected from the group consisting of platinum and palladium, wherein the metal material stabilizes the oxidized glutathione-based compound.

2. The composition of claim 1, wherein the metal is platinum.

3. The composition of claim 2, wherein the platinum material is selected from the group consisting of a platinum salt, a coordination compound, and an organometallic compound.

4. The composition of claim 3, wherein the platinum material is a platinum coordination compound.

5. The composition of claim 4, wherein the coordination compound is cis-platin.

6. The composition of claim 2, wherein the platinum is present in an amount of between about 0.0003 molar equivalent to about 1 molar equivalent relative to the oxidized glutathione-based compound.

7. The composition of claim 6, wherein the platinum is present in an amount of between about 0.001 molar equivalent to about 0.01 molar equivalent relative to the oxidized glutathione-based compound.

8. The composition of claim 1, wherein the oxidized glutathione-based compound is a salt selected from the group consisting of alkali metal salts, alkaline earth metal salts, and transition metal salts.

9. The composition of claim 1, wherein the oxidized glutathione-based compound is a salt selected from the group consisting of lithium salts, sodium salts, potassium salts, magnesium salts, calcium salts, vanadium salts, manganese salts, iron salts, molybdenum salts, and zinc salts.

10. The composition of claim 1, wherein the composite is present in a dosage form for composition use.

11. The composition of claim 10, wherein the dosage is between about 0.10 mg/kg to about 1.0 mg/kg by body weight.

12. The composition of claim 11, wherein the dosage is between about 1 mg/m$^2$ to about 100 mg/m$^2$ by body surface.

13. The composition of claim 11, wherein the composite is capable of being introduced in injectable form in a concentration between about 1% to about 10% by weight/volume.

14. The composition of claim 13, wherein the composite is capable of being introduced in injectable form in a concentration between about 0.01% to about 3.0% by weight/volume.

15. A method of stimulating endogenous production of cytokines and hemopoietic factors comprising introducing to a mammalian body in need of stimulation of cytokines or hemopoietic factors or both, an effective amount of a composition comprising an oxidized glutathione-based compound formed from two monomers, each monomer comprising a glutamic acid bonded to a cysteine bonded to a glycine, the two monomers being linked through a disulfide bond bridging the sulfur atoms of each respective cysteine of each monomer, the compound being stabilized with a metal material comprising a metal selected from the group consisting of platinum and palladium.

16. The method of claim 15, wherein the metal is platinum.

17. The method of claim 16, wherein the material is cis-platin.

18. The method of claim 15, wherein the composition is administered orally.

19. The method of claim 15, wherein the disease is selected from the group consisting of oncological, infectious, immunological, ischemic, neurodegenerative, metabolic, endocrinal, and other diseases.

20. The method of claim 15, wherein the composition is administered as a solution form selected from the group consisting of inhalation solutions, local instillations, eye drops, intranasal introductions, ointment for epicutaneous applications, intravenous solutions, injection solutions, and suppositories.

* * * * *